(12) United States Patent
Talalay et al.

(10) Patent No.: US 8,937,050 B2
(45) Date of Patent: Jan. 20, 2015

(54) METHODS AND COMPOSITIONS FOR TREATMENT OF AUTISM

(71) Applicants: Paul Talalay, Baltimore, MD (US); Andrew W. Zimmerman, Baltimore, MD (US); Kirby D. Smith, Baltimore, MD (US)

(72) Inventors: Paul Talalay, Baltimore, MD (US); Andrew W. Zimmerman, Baltimore, MD (US); Kirby D. Smith, Baltimore, MD (US)

(73) Assignees: The Johns Hopkins University, Baltimore, MD (US); Kennedy Krieger Institute, Inc., Baltimore, MD (US)

( * ) Notice: Subject to any disclaimer, the term of this patent is extended or adjusted under 35 U.S.C. 154(b) by 163 days.

(21) Appl. No.: 13/665,679

(22) Filed: Oct. 31, 2012

(65) Prior Publication Data

US 2013/0123203 A1   May 16, 2013

Related U.S. Application Data

(60) Provisional application No. 61/558,486, filed on Nov. 11, 2011, provisional application No. 61/558,094, filed on Nov. 10, 2011, provisional application No. 61/553,509, filed on Oct. 31, 2011.

(51) Int. Cl.
| | |
|---|---|
| *A61K 31/145* | (2006.01) |
| *A61K 31/17* | (2006.01) |
| *A61K 31/70* | (2006.01) |
| *A61K 31/165* | (2006.01) |
| *A61K 31/18* | (2006.01) |
| *A61K 31/19* | (2006.01) |
| *A61K 31/192* | (2006.01) |
| *A61K 31/26* | (2006.01) |
| *A61K 31/343* | (2006.01) |
| *A61K 31/4045* | (2006.01) |
| *A61K 31/4184* | (2006.01) |
| *A61K 31/506* | (2006.01) |
| *A61K 31/517* | (2006.01) |
| *A61K 31/167* | (2006.01) |

(52) U.S. Cl.
CPC ............... *A61K 31/70* (2013.01); *A61K 31/145* (2013.01); *A61K 31/165* (2013.01); *A61K 31/17* (2013.01); *A61K 31/18* (2013.01); *A61K 31/19* (2013.01); *A61K 31/192* (2013.01); *A61K 31/26* (2013.01); *A61K 31/343* (2013.01); *A61K 31/4045* (2013.01); *A61K 31/4184* (2013.01); *A61K 31/506* (2013.01); *A61K 31/517* (2013.01); *A61K 31/167* (2013.01); *G01N 2800/52* (2013.01); *G01N 2800/2814* (2013.01)
USPC .............................. 514/24; 514/514; 514/665

(58) Field of Classification Search
CPC ...... A61K 31/145; A61K 31/17; A61K 31/18; A61K 31/19; A61K 31/192; A61K 31/26; G01N 2800/2814; G01N 2800/52
USPC ............................................ 514/24, 514, 665
See application file for complete search history.

(56) References Cited

U.S. PATENT DOCUMENTS

| | | | |
|---|---|---|---|
| 6,362,226 B2 * | 3/2002 | Phillips et al. ................. | 514/568 |
| 2005/0063965 A1 | 3/2005 | Guo ................................ | 514/514 |
| 2006/0188505 A1 | 8/2006 | Skurkovich .................... | 424/9.1 |
| 2008/0254017 A1 | 10/2008 | Kane ................................ | 514/78 |
| 2010/0016328 A1 | 1/2010 | Kakkis ............................ | 436/98 |
| 2010/0022495 A1 | 1/2010 | Hotamisligil ................. | 514/183 |
| 2010/0160372 A1 | 6/2010 | Lansbury ...................... | 514/312 |
| 2011/0229883 A1 | 9/2011 | Spur ................................ | 435/6 |
| 2011/0237669 A1 | 9/2011 | Stein ............................. | 514/560 |

FOREIGN PATENT DOCUMENTS

WO   WO 2013/067040   5/2013

OTHER PUBLICATIONS

Abel T and Zukin RS. Epigenetic targets of HDAC inhibition in neurodegenerative and psychiatric disorders. Curr Opin Pharmacol 8:57-64, 2008.*
Hanessian et al. Exploring alternative Zn-binding groups in the design of HDAC inhibitors: Squaric acid, N-hydroxyurea, and oxazoline analogues of SAHA. Bioorg Med Chem Lett 16:4784-4787, 2006.*
Akerfelt M, et al. 2010. Heat shock factors: integrators of cell stress, development and lifespan. Nat Rev Mol Cell Biol. 11(8): 545-555.
Qi X, et al. 2004. Sodium 4-phenylbutyrate protects against cerebral ischemic injury. Mol Pharmacol. 66: 899-908.
Baird L, et al. 2011. The cytoprotective role of the Keap1-Nrf2 pathway. Arch Toxicol. 85:241-272.
Bennett BL, et al. 2001. SP600125, an anthrapyrazolone inhibitor of Jun N-terminal kinase. Proc Natl Acad Sci USA. 98: 13681-13686.
Bergen AW, et al. 1999. An Asian-Native American paternal lineage identified by RPS4Y resequencing and by microsatellite haplotyping. Ann Hum Genet. 63: 63-80.
Calabrese V, et al. 2010. Cellular stress responses, the hormesis paradigm, and vitagenes: novel targets for therapeutic intervention in neurodegenerative disorders. Antioxid Redox Signal. 13: 1763-1811.
Chiurazzi P, et al. 1999. Synergistic effect of histone hyperacetylation and DNA demethylation in the reactivation of the FMR1 gene. Hum Mol Genet. 8: 2317-2323.
Choo-Kang LR, et al. 2001. Induction of HSP70 promotes DeltaF508 CFTR trafficking. Am J Physiol Lung Cell Mol Physiol. 281: L58-68.
Clark MS, et al. 2009. Triggers of the HSP70 stress response: environmental responses and laboratory manipulation in an Antarctic marine invertebrate (*Nacella concinna*). Cell Stress Chaperones. 14: 649-660.
Clarke JD, et al. 2011. Metabolism and Tissue Distribution of Sulforaphane in Nrf2 Knockout and Wild-Type Mice. Pharm Res.
Curran LK, et al. 2007. Behaviors associated with fever in children with autism spectrum disorders. Pediatrics. 120(6): e1386-1392.

(Continued)

*Primary Examiner* — Yong Chu
*Assistant Examiner* — Yih-Horng Shiao
(74) *Attorney, Agent, or Firm* — Cermak Nakajima & McGowan LLP; Malcolm K. McGowan

(57) ABSTRACT

Disclosed herein are methods and compositions for treating autism. Disclosed herein are methods and compositions for treating an autism spectrum disorder.

21 Claims, 14 Drawing Sheets

(56) References Cited

OTHER PUBLICATIONS

Durieux J, et al. 2011. The cell-non-autonomous nature of electron transport chain-mediated longevity. Cell. 144: 79-91.
Evans CG, et al. 2010. Heat shock protein 70 (hsp70) as an emerging drug target. J Med Chern. 53: 4585-4602.
Fedoroff N. 2006. Redox regulatory mechanisms in cellular stress responses. Ann Bot. 98: 289-300.
Gan N, et al. 2010. Sulforaphane activates heat shock response and enhances proteasome activity through up-regulation ofHsp27. J Bioi Chern. 285(46): 35528-35536.
Gardian G, et al. 2005. Neuroprotective effects of phenylbutyrate in the N171-82Q transgenic mouse model of Huntington's disease. J Bioi Chern. 280: 556-563.
Gibbs A, et al. 2009.Sulforaphane destabilizes the androgen receptor m prostate cancer cells by inactivating histone deacetylase 6. Proc Natl Acad Sci USA. 106(39): 16663-16668.
Powers ET, et al. 2009. Biological and chemical approaches to diseases of proteostasis deficiency. Annu Rev Biochem. 78: 959-991.
Habashi JP, et al. 2006. Losartan, an ATI antagonist, prevents aortic aneurysm in a mouse model ofMarfan syndrome. Science. 312: 117-121.
Petri S, et al. 2006. Additive neuroprotective effects of a histone inhibitor and a catalytic antioxidant in a transgenic mouse model of amyotrophic lateral sclerosis. Neurobiol Dis. 22: 40-49.
Horowitz M, et al. 2007. Heat shock proteins and the heat shock response during hyperthermia and its modulation by altered physiological conditions. Prog Brain Res. 162: 433-446.
Hsiao CH, et al. 2006. Fetal hemoglobin induction by histone deacetylase inhibitors involves generation of reactive oxygen species. Exp Hematol. 34: 264-273.
Hu R, et al. 2006. Gene expression profiles induced by cancer chemopreventive isothiocyanate sulforaphane in the liver of C57BL/6J mice and C57BL/6J/Nrf2 (–/–)mice. Cancer Lett. 243(2): 170-192.
Hutt DM, et al. 2010. Reduced histone deacetylase 7 activity restores function to misfolded CFTR in cystic fibrosis. Nat Chern Bioi. 6: 25-33.
James SJ, et al. 2009. Cellular and mitochondrial glutathione redox imbalance in lymphoblastoid cells derived from children with autism. FASEB J. 23(8): 2374-2383.
Jung M. 2001. Inhibitors of histone deacetylase as new anticancer agents. Curr Med Chem. 8: 1505-1511.
Keefer JR, et al. 2006. Role of cyclic nucleotides m fetal hemoglobin induction in cultured CD34+ cells. Exp Hematol. 34: 1151-1161.
Kemp S, et al. 1998. Gene redundancy and pharmacological gene therapy: implications for X-linked adrenoleukodystrophy. Nat Med. 4: 1261-1268.
Kultz D. 2003. Evolution of the cellular stress proteome: from monophyletic origin to ubiquitous function. J Exp Bioi. 206: 3119-3124.
Kultz D. 2005. Molecular and evolutionary basis of the cellular stress response. Annu Rev Physiol. 67: 225-257.
Lallemand D, et al. 1998. Stress-activated protein kinases are negatively regulated by cell density. EMBO J. 17: 5615-5626.
Lee HC, et al. 2005. Mitochondrial biogenesis and mitochondrial DNA maintenance of mammalian cells under oxidative stress. Int J Biochem Cell Bioi. 37: 822-834.
Li X, et al. 2002. PEXIIalpha is required for peroxisome proliferation in response to 4-phenylbutyrate but is dispensable for peroxisome proliferator-activated receptor alpha-mediated peroxisome proliferation. Mol Cell Bioi. 22: 8226-8240.
Liu J, et al. 2009. Targeting mitochondrial biogenesis for preventing and treating insulin resistance in diabetes and obesity: Hope from natural mitochondrial nutrients. Adv Drug Deliv Rev. 61: 1343-1352.
Lunn MR, et al. 2008. Spinal muscular atrophy. Lancet. 371: 2120-2133.
Martinet W, et al. 2009. Autophagy in disease: a double-edged sword with therapeutic potential. Clin Sci (Lond). 116: 697-712.

McGuinness MC, et al. 2003. Role of ALDP (ABCD1) and mitochondria in X-linked adrenoleukodystrophy. Mol Cell Biol23: 744-753.
McGuinness MC, et al. 2001. Evaluation of pharmacological induction of fatty acid beta-oxidation in X-linked adrenoleukodystrophy. Mol Genet Metab. 74(1-2): 256-263.
Mehler MF, et al. 2009. Autism, fever, epigenetics and the locus coeruleus. Brain Res Rev. 59(2): 388-392.
Miles JH. Unpublished observations. Paper presented at: Simons Foundation Workshop on Fever and Autism; Feb. 5, 2010.
Minetti GC, et al. 2006. Functional and morphological recovery of dystrophic muscles in mice treated with deacetylase inhibitors. Nat Med. 12: 1147-1150.
Myzak MC, et al. 2004. A novel mechanism of chemoprotection by sulforaphane: inhibition of histone deacetylase. Cancer Res. 64: 5767-5774.
Oliveira JM, et al. 2006. Mitochondrial-dependent Ca2+ handling in Huntington's disease striatal cells: effect of histone deacetylase inhibitors. J Neurosci. 26: 11174-11186.
Ong DS, et al. 2011. Chemical and/or biological therapeutic strategies to ameliorate protein misfolding diseases. Curr Opin Cell Bioi. 23(2):231-23 8.
Ozcan U, et al. 2006. Chemical chaperones reduce ER stress and restore glucose homeostasis in a mouse model of type 2 diabetes. Science. 313: 113 7-1140.
Park HM, et al. 2009. Protection against amyloid beta cytotoxicity sulforaphane: role of the proteasome. Arch Pharm Res. 32: 109-115.
Perrine SP. 2008. Fetal globin stimulant therapies m the betahemoglobinopathies: principles and current potential. Pediatr Ann .37: 339-346.
Ranganathan S, et al. 2009. Mitochondrial abnormalities in spinal and bulbar muscular atrophy. Hum Mol Genet. 18: 27-42.
Ricobaraza A, et al. 2009. Phenylbutyrate ameliorates cognitive deficit and reduces tau pathology in an Alzheimer's disease mouse model. N europsychopharmacology 34: 1721-1732.
Santos MJ, et al. 2005. Peroxisomal proliferation protects from beta-amyloid neurodegeneration. J Bioi Chern. 280: 41057-41068.
Schrader M, et al. 1998. Expression of PEXIIbeta mediates peroxisome proliferation in the absence of extracellular stimuli. J Bioi Chern. 273: 29607-29614.
Stetler RA, et al. 2010. Heat shock proteins: cellular and molecular mechanisms in the central nervous system. Prog N eurobiol. 92(2): 184-211.
Sun, et al. 2008. Trichostatin A improves insulin stimulated glucose utilization and insulin signalitransduction through the repression of HDAC2. Biochem Pharmacol. 76:120-127.
Toth A, et al. 2007. Endoplasmic reticulum stress as a novel therapeutic target in heart diseases. Cardiovasc Hematol Disord Drug Targets. 7: 205-218.
Vandesompele J, et al. 2002. Accurate normalization of real-time quantitative RT-PCR data by geometric averaging of multiple internal control genes. Genome Bioi. 3:RESEARCH00.
Vargas DL, et al. 2005. Neuroglial activation and neuroinflammation in the brain of patients with autism. Ann Neurol. 57(1): 67-81.
Watkins PA, et al. 1995. Altered expression of ALDP m X-linked adrenoleukodystrophy. Am J Hum Genet. 57: 292-301.
Wei H, et al. 2000. Pharmacological induction of peroxisomes in peroxisome biogenesis disorders. Ann Neurol. 47: 286-296.
Weissman JR, et al. 2008. Mitochondrial disease in autism spectrum disorder patients: a cohort analysis. PLoS One. 3(11 ): e3 815.
Weng SJ, et al. 2010. Alterations of resting state functional connectivity in the default network in adolescents with autism spectrum disorders. Brain Res. 1313: 202-214.
Westerheide SD, et al. 2009. Stress-inducible regulation of heat shock factor 1 by the deacetylase SIRTI. Science. 323: 1063-1066.
Wiggins JL, et al. 2011. Using a self-organizing map algorithm to detect agerelated changes in functional connectivity during rest in autism spectrum disorders. Brain Res. 138.
Xue M, et al. 2008. Activation of NF-E2-related factor-2 reverses biochemicaldysfunction of endothelial cells induced by hyperglycemia linked to vascular disease Diabetes. 57.
Yang J, et al. 2003. Protein kinases and their involvement in the cellular responses to genotoxic stress. Mutat Res. 543: 31-58.

(56) References Cited

OTHER PUBLICATIONS

Yoon HY, et al. 2008. Sulforaphane protects kidneys against ischemiareperfusion injury through induction of the Nrf2-dependent phase 2 enzyme. Biochem Pharmacol. 75: 2214-222.

Zhao J, et al. 2005. Sulforaphane enhances aquaporin-4 expression and decreases cerebral edema following traumatic brain injury. J Neurosci Res. 82( 4): 499-506.

Madeo F, et al. 2009. Autophagy for the avoidance of neurodegeneration. Genes Dev. 23: 2253-2259.

Aman MG, et al. (1985) The aberrant behavior checklist: a behavior rating scale for the assessment of treatment effects. Am J Ment Defic. 89(5):485-491.

Gorski G, et al. (1985) Increased expression of fragile site Xq by hydroxyurea. Preliminary communication. Acta Anthropogenet. 9(1-3):71-76.

Heinzer AK, et al. (2003) Mouse models and genetic modifiers in X-linked adrenoleukodystrophy. Adv Exp Med Biol. 544:75-93.

International Search Report and Written Opinion issued Feb. 8, 2013 for PCT Application No. PCT/US2012/062841 filed Oct. 31, 2012 and published as WO 2013/067040 on May 10, 2013 (Inventors—Talalay et al. // Applicant—The Johns Hopkins University) (17 pages).

International Preliminary Report on Patentability issued May 6, 2014 for PCT Application No. PCT/US2012/062841 filed Oct. 31, 2012 and published as WO 2013/067040 on May 10, 2013 (Inventors—Talalay et al. // Applicant—The Johns Hopkins University) (8 pages).

Enstrom AM, et al. (2009) Altered gene expression and function of peripheral blood natural killer cells in children with autism. Brain Behav Immun. 23(1):124-33.

Fujita E, et al. (2010). Autism spectrum disorder is related to endoplasmic reticulum stress induced by mutations in the synaptic cell adhesion molecule, CADM1. Cell Death Dis. 1:e47.

Kültz D. (2003) Evolution of the cellular stress proteome: from monophyletic origin to ubiquitous function. J Exp Biol. 206(Pt 18):3119-3124.

Sweeten TL, et al. High nitric oxide production in autistic disorder: a possible role for interferon-gamma. Biol Psychiatry. 55(4):434-437. (2004).

\* cited by examiner

METHODS AND COMPOSITIONS FOR TREATMENT OF AUTISM

CROSS-REFERENCE TO RELATED APPLICATIONS

The present application claims priority to U.S. Provisional Patent Application No. 61/558,486 filed Nov. 11, 2011, to U.S. Provisional Patent Application No. 61/558,094 filed Nov. 10, 2011, and to U.S. Provisional Patent Application No. 61/553,509 filed Oct. 31, 2011, which applications are incorporated herein in their entirety.

STATEMENT REGARDING FEDERALLY SPONSORED RESEARCH

This invention was made with government support under GM077456, HD10981 and HD20961 awarded by Johns Hopkins McKusick-Nathans Institute of Genetic Medicine and Public Health Service. The government has certain rights in the invention.

BACKGROUND

Autism is currently one of five disorders that fall under the umbrella of Pervasive Developmental Disorders (PDD), a category of neurological disorders characterized by severe and pervasive impairment in several areas of development. Autism is a complex developmental disability that typically appears during the first two years of life and affects the functioning of the brain, impacting development of social interaction and communication skills. Both children and adults on the autism spectrum typically show difficulties in verbal and non-verbal communication, social interactions, and leisure or play activities. Autism knows no racial, ethnic, or social boundaries, and can affect any family and any child.

Autism statistics from the U.S. Centers for Disease Control and Prevention (CDC) identify around 1 in 88 American children as on the autism spectrum—a ten-fold increase in prevalence in 40 years. Careful research shows that this increase is only partly explained by improved diagnosis and awareness. Studies also show that autism is four to five times more common among boys than girls. An estimated 1 out of 54 boys and 1 in 252 girls are diagnosed with autism in the United States.

Despite progress in genetic research in autism spectrum disorders (ASD), direct treatment of underlying abnormal cellular mechanisms in ASD is not yet possible. Genetic associations correlate with at most only ~20% of ASD patients. This indicates considerable clinical heterogeneity, which likely results from multiple cellular mechanisms. Several clinical and laboratory findings in ASD indicate that different types of cellular dysfunction, including neuro-inflammation (Vargas et al., 2005), oxidative stress (James et al., 2009), and mitochondrial abnormalities (Weissman et al., 2008), and abnormal synaptic plasticity and connectivity (Weng et al., 2010), involve a number of related, interacting metabolic pathways.

The medications and treatments currently used to treat autism and autism spectrum disorders are symptomatic; there is no evidence that these medications either improve core features (e.g., social responsiveness) or affect the neurodevelopmental trajectory. Thus, despite intensive efforts, no effective methods for treatment or prevention of autism are available.

What is needed is a mechanism-based strategy that targets the intrinsic cellular stress response and modulates the metabolic defects that contribute to the symptomatology of autism and autism spectrum disorders.

SUMMARY

Disclosed herein is a method of treating autism, comprising, administering to a subject diagnosed with autism an effective amount of a composition comprising a compound that induces a general cellular stress response in at least one cell of the subject; and allowing the subject's treated or affected cells to return to cellular homeostasis that existed prior to administering the compound. A composition may comprise a pharmaceutical composition, a natural product composition, a medical food, a nutritional supplement, or a composition comprising excipients, diluents, enzymes, cofactors, and delivery vehicle additives. The treatment of subjects with compounds disclosed herein comprise a return, by treated and/or affected cells, to a state substantially similar to the state of the treated cells prior to treatment, herein referred to as a return to cellular homeostasis. In the treated subject as a whole, the symptoms of and state of the subject's autism or autism spectrum disorder is reduced by such a treatment, so that the subject has lessened, or fewer attributes of, autism or autism spectrum disorder.

Disclosed herein is a method of treating autism, comprising, administering to at least one cell of a subject diagnosed with autism an effective amount of a composition comprising a compound that induces a general cellular stress response in the at least one cell of the subject; and allowing the cell to return to homeostasis that existed prior to administering the compound. A composition may comprise a pharmaceutical composition, a natural product composition, a medical food, a nutritional supplement, or a composition comprising excipients, diluents, enzymes, cofactors, and delivery vehicle additives.

Disclosed herein is a method of treating autism, comprising, administering to a subject diagnosed with autism an effective amount of a composition that modulates measurable effects of behavioral symptoms. A composition may comprise a pharmaceutical composition, a natural product composition, a medical food, a nutritional supplement, or a composition comprising excipients, diluents, enzymes, cofactors, and delivery vehicle additives.

Disclosed herein is a method of treating autism, comprising, administering to a subject diagnosed with autism an effective amount of a composition that modulates social responsiveness of the subject treated. A composition may comprise a pharmaceutical composition, a natural product composition, a medical food, a nutritional supplement, or a composition comprising excipients, diluents, enzymes, cofactors, and delivery vehicle additives.

Disclosed herein is a method of treating one or more autism spectrum disorders, comprising, administering to a subject diagnosed with one or more autism spectrum disorders an effective amount of a composition comprising a compound that induces a general cellular stress response in at least one cell of the person. A composition may comprise a pharmaceutical composition, a natural product composition, a medical food, a nutritional supplement, or a composition comprising excipients, diluents, enzymes, cofactors, and delivery vehicle additives.

Disclosed herein is a method of treating one or more autism spectrum disorders, comprising, administering to a subject diagnosed with one or more autism spectrum disorders an effective amount of a composition that modulates measurable effects of behavioral symptoms. A composition may comprise a pharmaceutical composition, a natural product composition, a medical food, a nutritional supplement, or a composition comprising excipients, diluents, enzymes, cofactors, and delivery vehicle additives.

Disclosed herein is a method of treating one or more autism spectrum disorders, comprising, administering to a subject diagnosed with one or more autism spectrum disorders an effective amount of a composition that modulates social responsiveness of the subject treated. A composition may comprise a pharmaceutical composition, a natural product composition, a medical food, a nutritional supplement, or a composition comprising excipients, diluents, enzymes, cofactors, and delivery vehicle additives.

Disclosed herein is a method for determining effectiveness of a compound in treating autism or autism related disorder, comprising, administering to a first cell an effective amount of a compound to be tested, comparing the response of the first cell with the response of an identical cell that was treated with a compound that induces a generalized stress response, and determining whether or not the tested compound induces a general cellular stress response in cells.

Disclosed herein are medical foods used to treat autism or one or more autism spectrum disorders.

Disclosed herein are dietary or nutritional supplements used to treat autism or one or more autism spectrum disorders.

Disclosed herein are compounds derived from natural or synthetic sources which may be used in a composition to treat autism or one or more autism spectrum disorders.

BRIEF DESCRIPTION OF THE FIGURES

The accompanying Figures, which are incorporated in and constitute a part of this specification, illustrate several aspects and together with the description serve to explain the principles of the invention.

DESCRIPTION

A. Autism and Autism Spectrum Disorders

Figure 1:
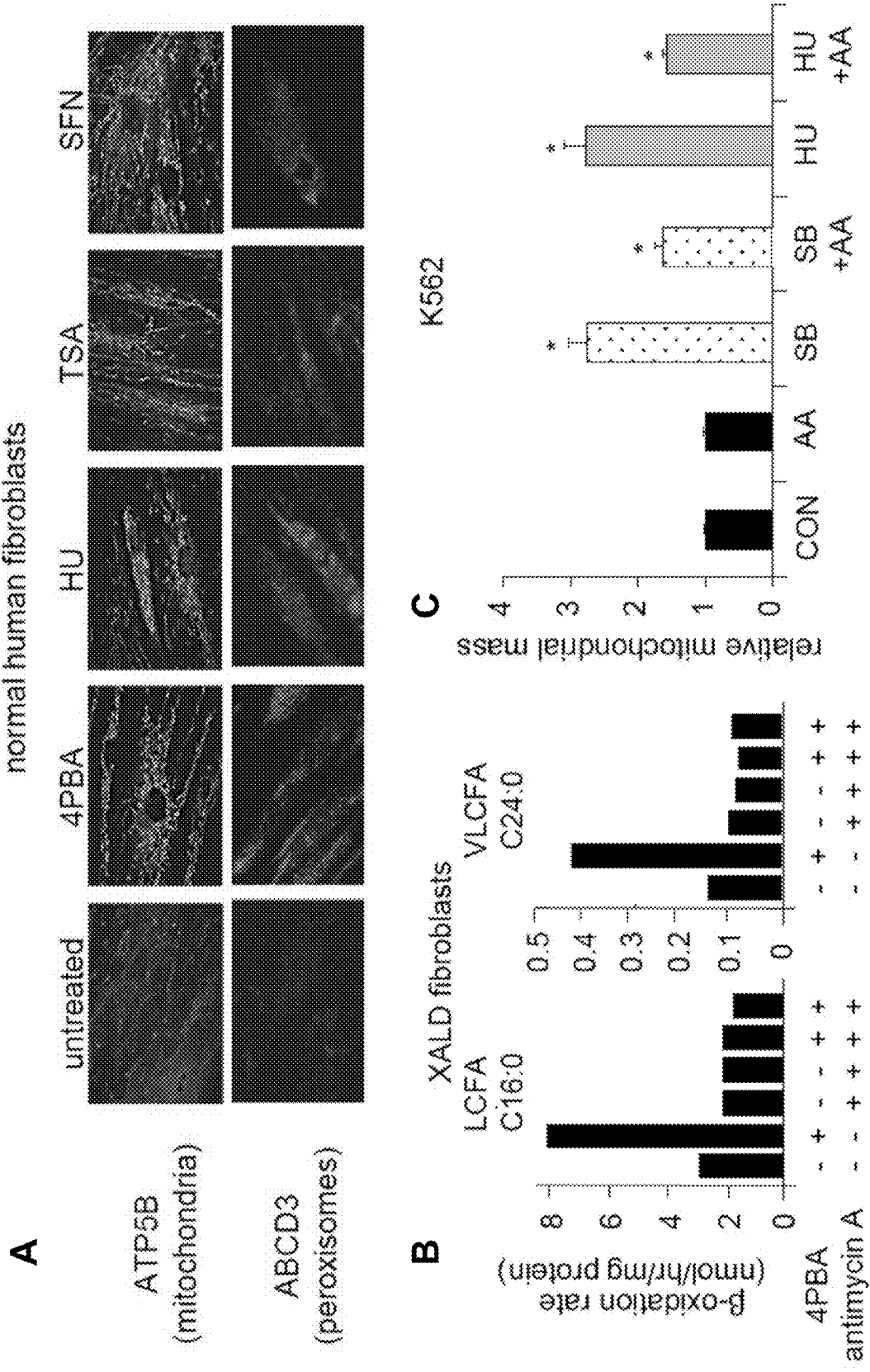
FIG. 1 (A-E) shows that the beneficial responses in XALD and K562 cells involves pharmacological induction of mitochondrial function FIG. 2 (A-F) shows that the mitochondrial biogenesis induced by 4PBA, HU, TSA, or SFN is JNK-dependent.
Figure 1:
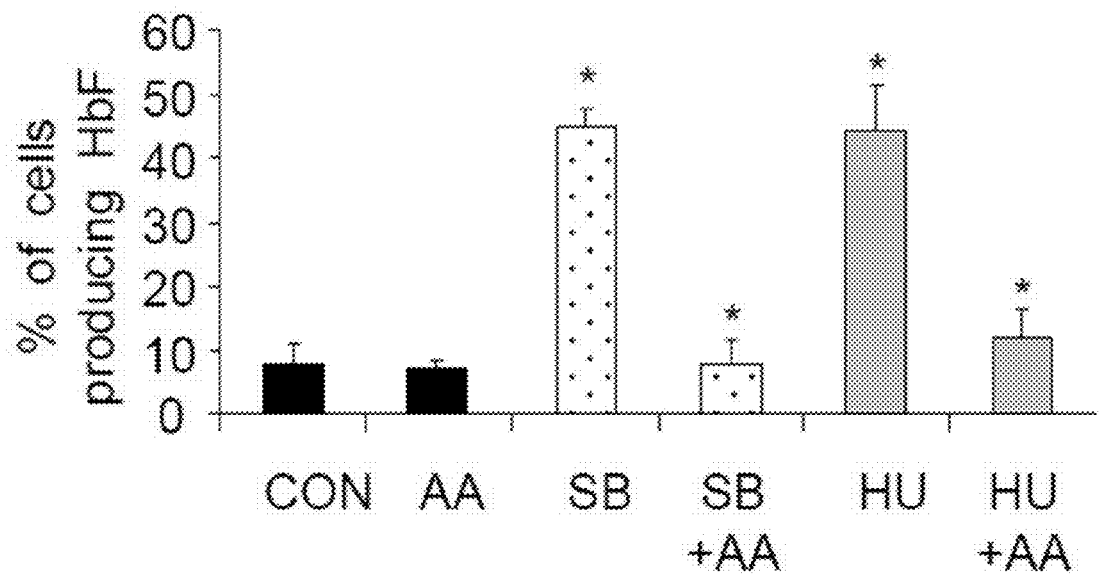
Figure 1:
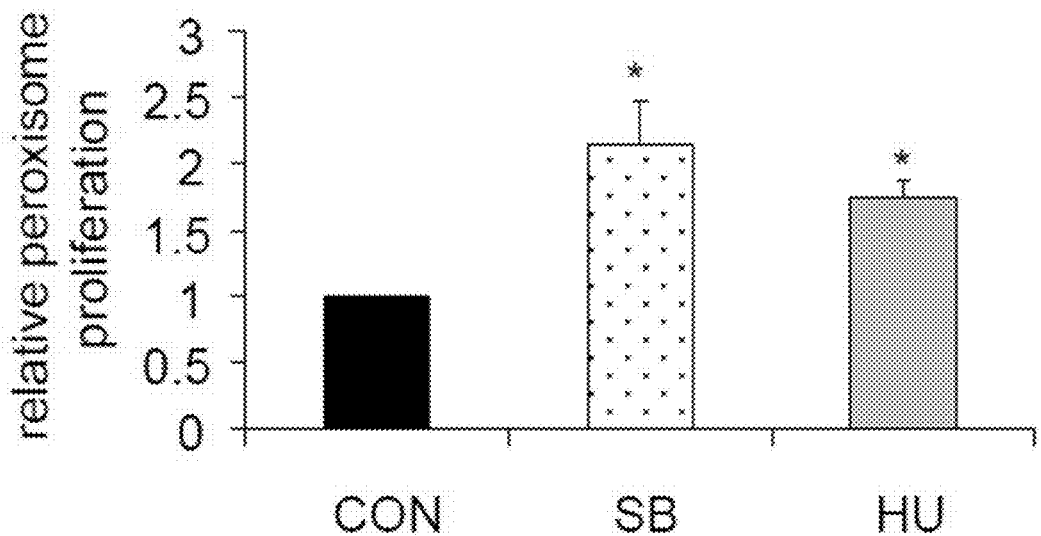

Autism spectrum disorder (ASD) and autism are both general terms for a group of complex disorders of brain development. These disorders are characterized, in varying degrees, by difficulties in social interaction, verbal and nonverbal communication and repetitive behaviors. These disorders include, but are not limited to, autistic disorder, Rett syndrome, childhood disintegrative disorder, pervasive developmental disorder-not otherwise specified (PDD-NOS) and Asperger syndrome. ASD can be associated with intellectual disability, difficulties in motor coordination and attention and physical health issues such as sleep and gastrointestinal disturbances. Some persons with ASD excel in visual skills, music, math and art. (See, e.g., Wiggins et al. 2011, which is incorporated herein in its entirety by reference, and which shows that adolescents with ASD have weaker connectivity between the posterior hub of the default network and the right superior frontal gyms). Though not wishing to be bound by any particular theory, it is believed that autism spectrum disorders may result from a variety of non-lethal genetic disorders and epigenetic effects that affect related metabolic pathways.

such as self-organizing maps (SOM), to create a reference for each participant to calculate connectivity. We used individualized resting-state clusters identified by an SOM algorithm to corroborate previous findings of weaker posterior-anterior connectivity in the ASD group and examine age-related changes in the ASD and control groups. Thirty-nine adolescents with ASD and 41 controls underwent a 10-minute, eyes-open, resting-state functional MRI scan. Additionally, controls have larger increases in connectivity with age compared to the ASD group. These findings indicate that SOM is a complementary method for calculating connectivity in a clinical population. Additionally, adolescents with ASD have a different developmental trajectory of the default network compared to controls.

Behaviors in 38% (Miles 2010) to 83% (Curran et al., 2007) of autistic children transiently improved during episodes of fever. Improvements were most notable in reduced stereotypic behaviors and inappropriate speech. Improvements were not related to the degree of fever or severity of illness (Curran et al., 2007, which is incorporated in its entirety by this reference). Fever stimulates the HSP, which are important for multiple cellular processes in the CNS, including synaptic transmission. (Stetler et al., 2010).

The cellular stress proteome is a complex of interacting proteins involved in pathways that respond to various stressors, such as fever, irradiation and hypoxia, and functions to re-establish homeostasis. Stress response pathways are not stressor specific and include organelle biogenesis. MAPK signaling, antioxidant production, heat shock proteins, unfolded protein responses, and autophagy (Stetler et al., 2010).

B. Compositions i) Glucosinolates

The present invention comprises methods and compositions comprising glucosinolates for the treatment of autism and autism spectrum disorders. Though not wishing to be bound by any particular theory, it is currently believed that a benefit of crucifer plants is their content of isothiocyanates and their precursor molecules, glucosinolates. Glucosinolates are converted to isothiocyanates by the enzymes such as thioglucosides, for example, myrosinase. Generally, in plant cells, myrosinase and glucosinolates are separated in the cell and if the cell is damaged, such as by insect predation, with loss of compartmentalization, myrosinase or other similarly acting enzymes comes into contact with glucosinolates, which are then converted to isothiocyanates. Myrosinase, EC 3.2.1.147, CAS number 9025-38-1 is known to those of skill in the art, as are similarly acting enzymes that convert precursor molecules, such as glucosinolates, to more active compounds, such as isothiocyanates, such as sulforaphane.

The present invention comprises methods and compositions comprising one or more enzymes, and/or one or more types of enzymes, and optionally co-factors or other enzymes in the metabolic pathway, for the treatment of autism and autism spectrum disorders. Enzymes contemplated by the present invention, referred to herein as enzymes of the present invention, comprise, but are not limited to, myrosinase, thioglucosidases, glutathione transferases, NAD(P)H:quinone reductase (QR) and glucuronosyltransferases, which have similar activities or are in related pathways. For example, as known in the art, in the presence of water, myrosinase cleaves the glucose group from a glucosinolate. The remaining molecule then converts to a thiocyanate, an isothiocyanate or a nitrile; these are the active substances that serve as defense for the plant. The hydrolysis of glucosinolates by myrosinase or other enzymes of the present invention or similarly acting enzymes can yield a variety of products, depending on various physiological conditions such as pH and the presence of certain cofactors. Reactions have been observed to share the initial steps. First, the β-thioglucoside linkage is cleaved by myrosinase, releasing D-glucose. The resulting aglycone undergoes a spontaneous Lossen-like rearrangement, releasing a sulfate. The last step in the mechanism is subject to the greatest variety depending on the physiological conditions under which the reaction takes place. At neutral pH, the primary product is the isothiocyanate. Under acidic conditions (pH<3), and in the presence of ferrous ions or epithiospecifer proteins, the formation of nitriles is favored instead.

Methods for the extraction of natural products as sources for compounds such as sulforaphane, include methods for extraction from plant sources in contrast to those produced by chemical synthetic methods, such as from plant sources such as cruciferous vegetables include, but are not limited to homogenization of the vegetables in cold water, lyophilization, extraction of the resultant powder with acetonitrile, filtration and evaporative concentration. Other methods for extraction of compounds from plants are known in the art and are contemplated by the present invention, and may comprise, for example, extractions of seeds and sprouts to produce compounds of the present invention, such as taught by U.S. Pat. No. 5,725,895, which is herein incorporated in its entirety. Known methods for extracting natural products, particularly from cruciferous plants, comprise extraction methods comprising boiling water extraction of desired compounds.

Though not wishing to be bound by any particular theory, it is currently believed that glucosinolates are a precursor molecule without activity that is then converted by enzymes into an active form, for example an isothiocynate such as sulforaphane (which may be referred to herein as a more active compound because the compound is more active in particular assays than the activity of its precursor molecule. Compositions of the present invention comprise one or more precursor compounds, such as glucosinolates, and/or may comprise more active molecules such as products made by enzymatic activity on glucosinolates, for example sulforaphane, or both one or more precursor compounds and one or more active compounds, and further may optionally comprise one or more enzymes and/or co-factors of such enzymes that use the precursor compound or the more active compound as a substrate. Glucosinolates in foods are converted at least partially to isothiocyanates in humans, by, it is currently believed, microorganisms of the gut. For example, a composition of the present invention may comprise one or more precursor compounds, such as glucosinolate, for the treatment of autism and autism spectrum disorders. A composition may further comprise one or more enzymes for which the compound provided in the composition is a substrate molecule of the one or more enzymes. The composition may be provided in a unitary delivery vehicle or may be provided in two or more delivery vehicles which may be provided simultaneously, sequentially, or in other administrative methods.

ii) Cruciferous Plant Sources

Plant sources suitable for use in the methods and compositions disclosed herein may be any portion of a cruciferous plant, including, but not limited to cells, seeds, sprouts, leaves, stalks, roots, flowers and other plant structures. Plant sources contemplated by the present invention comprise, but are not limited to, plants from the family Cruciferae, such as Brassiceae, and including Brassicinae. For example, the plant source may be *Brassica oleracea* selected from the group of varieties of *acephala* (kale, collards, wild cabbage, curly kale), *medullosa* (marrowstem kale), *ramosa* (thousand head kale), *alboglabra* (Chinese kale), *botrytis* (cauliflower, sprouting broccoli), *costata* (Portuguese kale), *gemmifera* (Brussels sprouts), *gongylodes* (kohlrabi), *italica* (broccoli), *palmifolia* (Jersey kale), *sabauda* (savoy cabbage), *sabellica* (collards), and *selensia* (borecole), among others.

Useful broccoli cultivars to be used in the method and compositions disclosed herein are Saga, DeCicco, Everest, Emerald City, Packman, Corvet, Dandy Early, Emperor, Mariner, Green Comet, Green Valiant, Arcadia, Calabrese Caravel, Chancellor, Citation, Cruiser, Early Purple Sprouting Red Arrow, Eureka, Excelsior, Galleon, Ging a, Goliath, Green Duke, Greenbelt, Italian Sprouting, Late Purple Sprouting, Late Winter Sprouting White Star, Legend, Leprechaun, Marathon, Mariner, Minaret (Romanesco), Paragon, Patriot, Premium Crop, Rapine (Spring Raab), Rosalind, Salade (Fall Raab), Samurai, Shogun, Sprinter, Sultan, Taiko, and Trixie. However, many other broccoli cultivars are suitable.

Useful cauliflower cultivars to be used in the method and compositions disclosed herein are Alverda, Amazing, Andes, Burgundy Queen, Candid Charm, Cashmere, Christmas White, Dominant, Elby, Extra Early Snowball, Fremont, Incline, Milkyway Minuteman, Rushmore, S-207, Serrano, Sierra Nevada, Siria, Snow Crown, Snow Flake, Snow Grace, Snowbred, Solide, Taipan, Violet Queen, White Baron, White Bishop, White Contessa, White Corona, White Dove, White Flash, White Fox, White Knight, White Light, White Queen, White Rock, White Sails, White Summer, White Top, Yukon. However, many other cauliflower cultivars are suitable.

iii) Sulforaphane

A composition of the present invention comprises sulforaphane, an organosulfur compound (1-isothiocyanato-4R-(methylsulfinyl)butane), derivatives known in the art, such as dithiocarbamate derivatives and others disclosed herein, and analogs known in the art and/or disclosed herein. Sulforaphane is a hormetic drug that, though not wishing to be bound by any particular theory, is thought to induce a general "cell protective" response. Sulforaphane is an active component of many plants and for example, may be extracted from broccoli sprouts, or may be made by chemical synthetic methods. Sulforaphane may be obtained from lyophilized, freeze dried extracts of 3-day-old broccoli sprouts. Broccoli sprouts are widely consumed all over the world by a very large number of individuals, without any reports of adverse effects. Human research studies have also not shown any significant adverse effects by administration of sulforaphane.

Sulforaphane crosses the blood brain barrier. Studies have demonstrated bioavailability of sulforaphane to the brain, peripheral nervous system, and nerve cells. Studies in various strains of mice and rats have demonstrated the accumulation of sulforaphane (and its dithiocarbamate metabolites) in the brain after various routes of administration (Zhao et al., 2005 and Clarke et al., 2011, both of which is incorporated in their entirety by this reference).

Though not wishing to be bound by any particular theory, it is believed that sulfurophane may provide protection against oxidative and inflammatory stress, such as disturbances of systems that protect cells against oxidative damage, heat shock, and disturbances caused by protein misfolding. These protective mechanisms are thought to be mediated by the transcription factor Nrf2 which controls expression of genes of the human genome via the Keap1/Nrf2/ARE regulatory system. This system may be upregulated in many tissues including the brain by sulforaphane. (See, e.g., Baird et al., 2011, which is incorporated in its entirety by this reference).

Data has shown that heat shock protein and ubiquitin 26s proteasome subunits were induced in mice after treatment with sulforaphane (Hu et al., 2008). Heat shock factor 1 (HSF1) and expression of HSP 27 were amplified by sulforaphane. In HeLa cells, sulforaphane upregulates HSP70 and HSP90. Others have found that the Keap1-Nrf2 Pathway may be involved. (Baird et al., 2011).

The art is familiar with sulforaphane analogs, which include, but are not limited to, the following: 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3-(methylsulfonyl)cyclohexylmethylisothiocyanante and trans-3-(methylsulfonyl)cyclohexylmethylisothiocyanante.

iv) Compounds of the Present Invention

A composition of the present invention may comprise one or more compounds disclosed herein, for example, histone deacetylase inhibitors, Class I and class II histone deacetylase inhibitors, and compounds that are not histone deacetylase inhibitors, such as hydroxyurea, sulforaphane and/or its derivatives and analogs. A composition of the present invention may comprise a compound that modulates one or more aspects of the general cellular stress response of a cell. It is currently believed that one or more pathways may be involved in modulating the general cellular stress response of a cell, and the present invention contemplates compounds, including, but not limited to those disclosed herein, that up-regulate the general cellular stress response of a cell, as described herein and as is commonly understood in the art.

For example, in an aspect, a composition comprises 4-phenylbutyrate. In an aspect, a composition comprises sodium butyrate. In an aspect, a composition comprises hydroxyurea. In an aspect, a composition comprises sulforaphane. In an aspect, a composition comprises derivatives of sulforaphane. In an aspect, a composition comprises analogs of sulforaphane. In an aspect, a composition comprises trichostatin A. In an aspect, a composition comprises a combination of compounds disclosed herein, for example a composition comprising one or more of hydroxyurea, sulforaphane, 4-phenylbutyrate, sodium butyrate, and/or trichostatin A. For example, a composition comprises a combination comprising phenylbutyrate and sodium butyrate. In an aspect, a composition comprises a combination comprising phenylbutyrate and trichostatin A. In an aspect, a composition comprises a combination comprising sodium butyrate and trichostatin A. In an aspect, a composition comprises a combination comprising hydroxyurea, phenylbutyrate, sodium butyrate. In an aspect, a composition comprises a combination comprising hydroxyurea and sulforaphane. In an aspect, a composition comprises a combination comprising hydroxyurea and sulforaphane derivatives or analogs, as known and/or disclosed herein. In an aspect, a composition comprises a combination comprising hydroxyurea, sulforaphane, phenylbutyrate, sodium butyrate, and trichostatin A. In an aspect, a composition comprises a combination comprising sulforaphane, phenylbutyrate, sodium butyrate, and trichostatin A. In an aspect, a composition comprises a combination comprising sulforaphane derivatives or analogs, and one or more of phenylbutyrate, sodium butyrate, and trichostatin A.

A composition of the present invention may comprise a compound that is present as a structure represented by a formula:

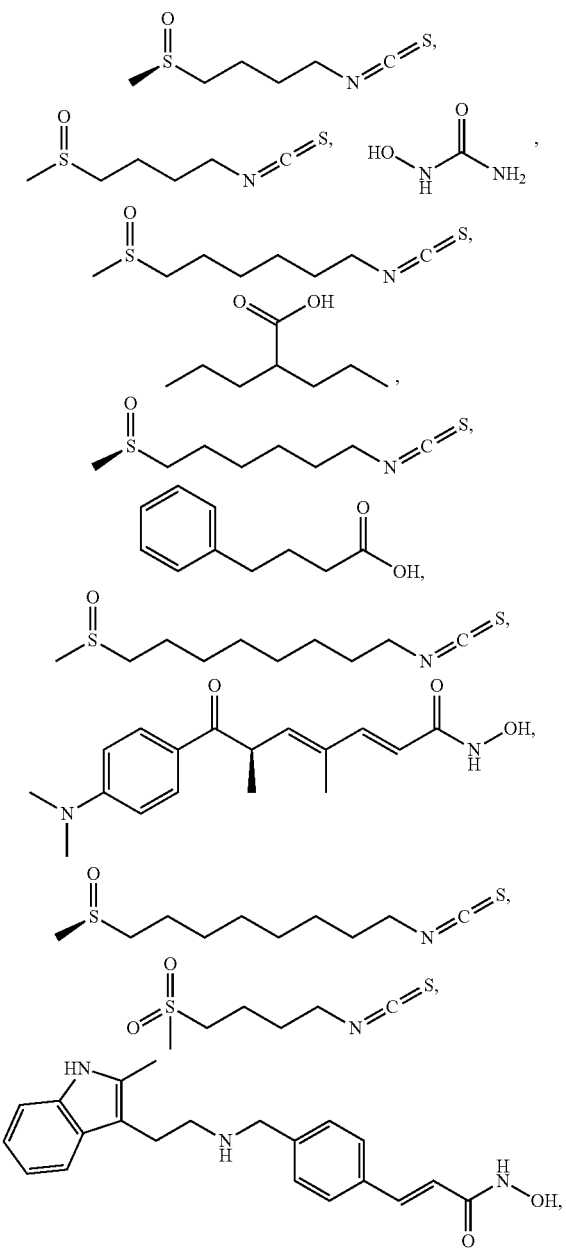

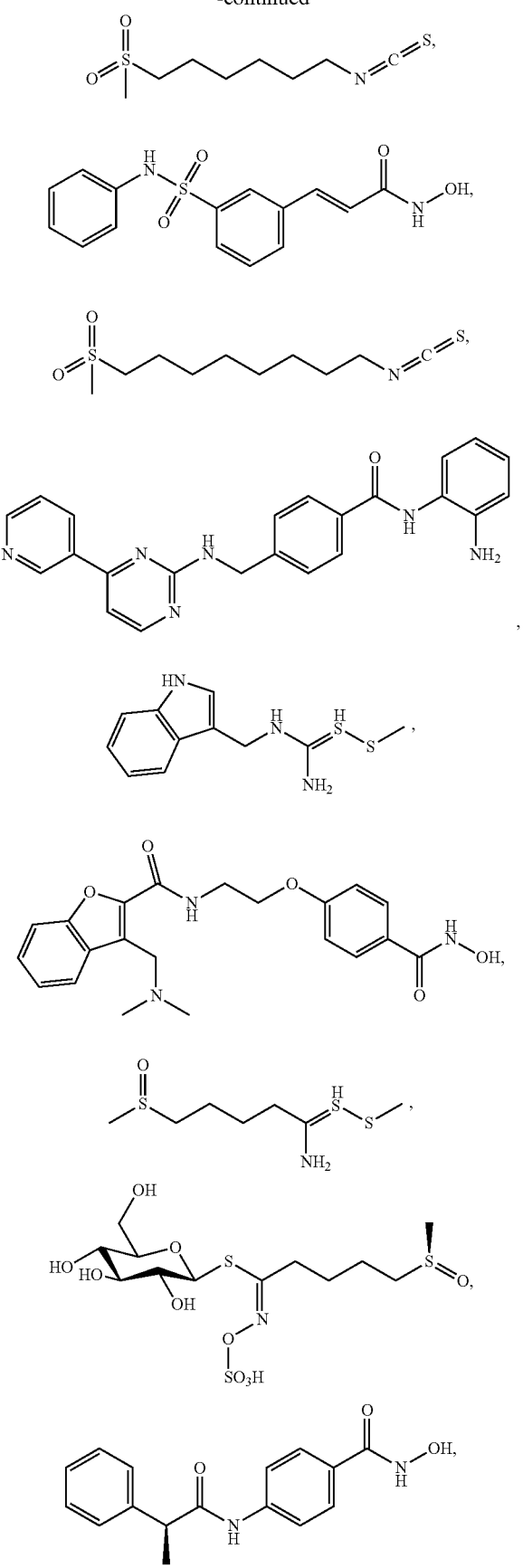

, or a subgroup or pharmaceutically acceptable salt thereof v) Compounds that Modulate the General Cell Stress Response The present invention comprises methods and compositions comprising compounds for the treatment of autism and autism spectrum disorders that modulate the general cellular stress response that modulate, for example, transcription and expression of heat shock factors and heat shock proteins. Heat shock proteins (HSPs) are involved in sensing and repairing DNA damage and function as molecular chaperones in many pathways. Heat shock factors (HSF) are transcriptional regulators for HSP that act as stress integrators in cells and organisms to maintain homeostasis and are evolutionarily conserved. (Akerfelt et al., 2010).

Methods of the present invention comprise administering an effective amount of a compound disclosed herein, such as histone deacetylase (HDAC) inhibitors and non-HDAC inhibitors, such as hydroxyurea or sulforaphane, to modulate the general cellular stress response, such as modulating levels and amounts of nucleic acids and peptides and proteins associated with the general cellular stress response, including mitochondrial biogenesis, peroxisome proliferation, activation of the stress proteome, transcription and/or translation of genes and proteins encoded by genes comprising heat shock and unfolded protein, genes for autophagic responses, genes for antioxidant responses, and genes for the c-jun-N-terminal kinase pathway.

A composition of the present invention that modulates the general stress response in a cell may comprise a compound that is present as a structure represented by a formula:

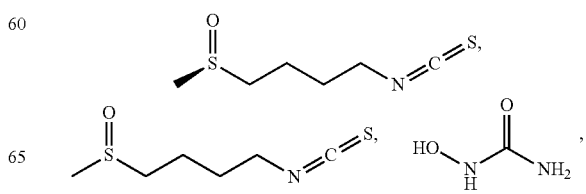

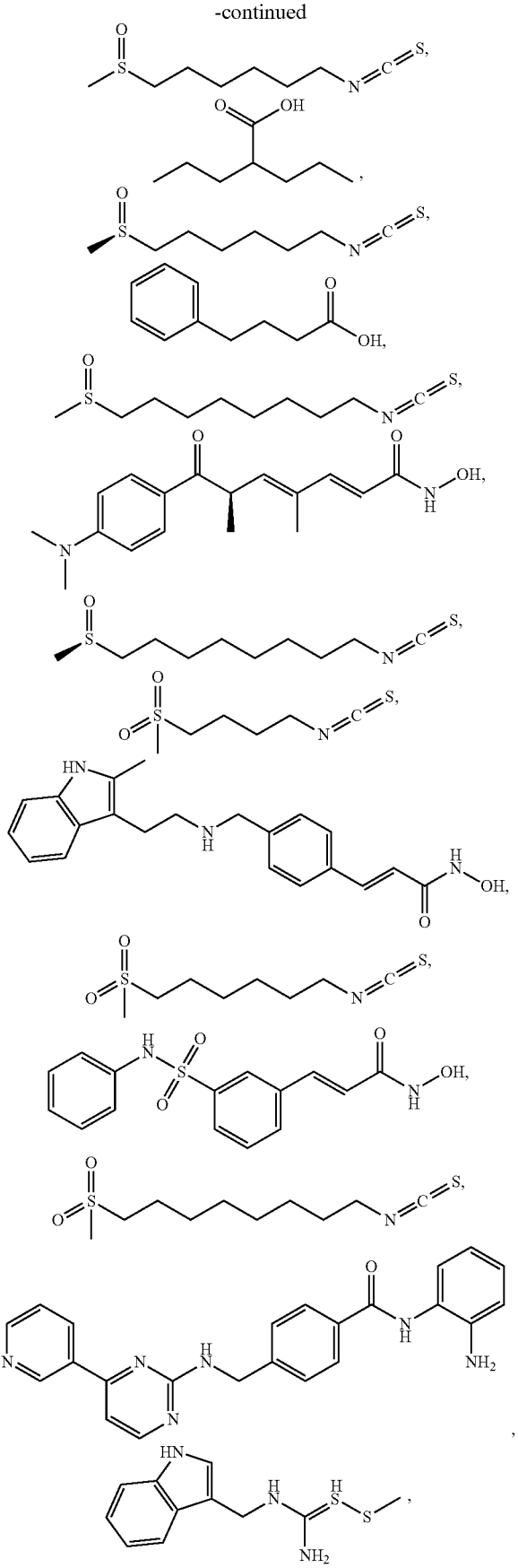
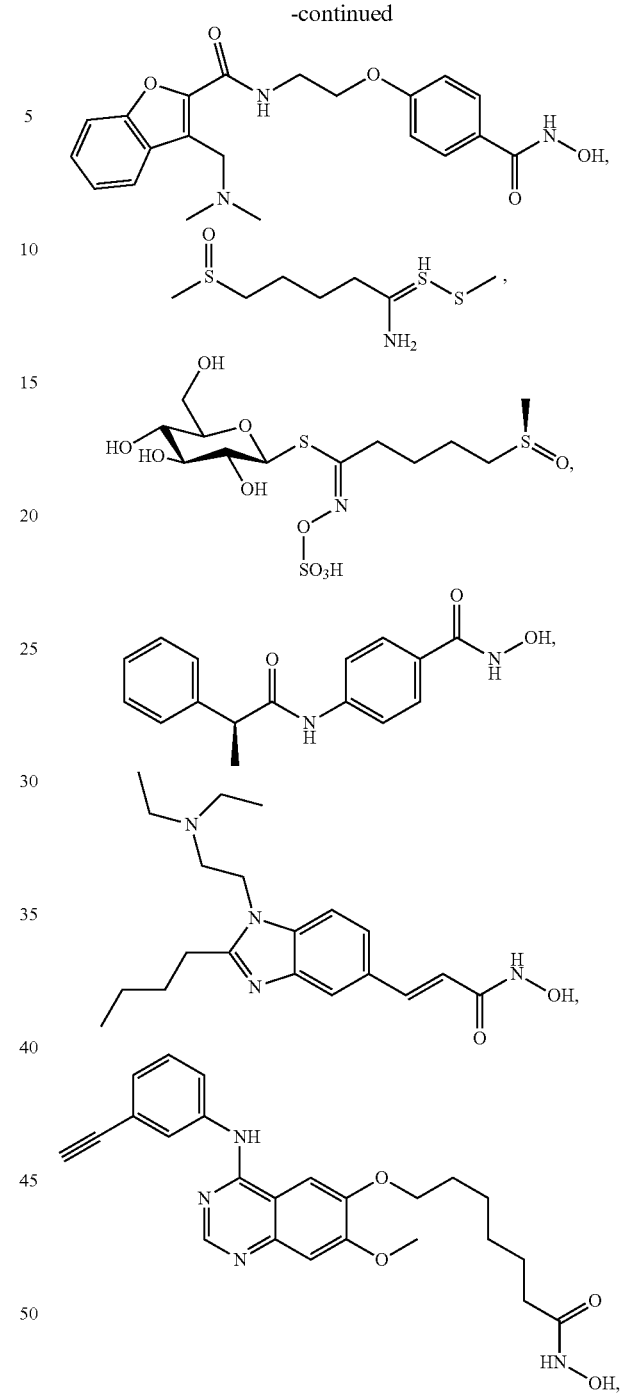

or a subgroup or pharmaceutically acceptable salt thereof.

Compositions of the present invention may comprise a compound disclosed herein that is formulated as a medical food. A composition of the present invention comprises a medical food comprising a compound disclosed herein and components known to those of skill in the art for producing medical foods. Medical foods are foods that are specially formulated and intended for the dietary management of a disease, such as autism and/or autism spectrum disorder, which has distinctive nutritional needs that cannot be met by normal diet alone. In an aspect, the disease, for example, is autism. In an aspect, the disease, for example, is one or more autism spectrum disorders. As defined by the FDA in section 5(b) of the Orphan Drug Act (21 U.S.C. 360ee (b) (3)), the term "medical food" is defined as "a food which is formulated to be consumed or administered enterally under the supervision of a physician and which is intended for the specific dietary management of a disease or condition for which distinctive nutritional requirements, based on recognized scientific principles, are established by medical evaluation."

vi) Medical Foods

Medical foods are distinct from the broader category of foods for special dietary use and from traditional foods that bear a health claim. In order to be considered a medical food the product must, at a minimum: (i) be a food for oral ingestion or tube feeding (nasogastric tube), (ii) be labeled for the dietary management of a specific medical disorder, disease or condition for which there are distinctive nutritional requirements, and (iii) be intended to be used under medical supervision. In an aspect, the disease for which there are distinctive nutritional requirements is, for example, autism. In an aspect, the disease for which there are distinctive nutritional requirements is, for example, one or more autism spectrum disorders.

Disclosed herein are medical foods used to treat autism. Disclosed herein are medical foods used to treat one or more autism spectrum disorders.

A composition of the present invention comprises a medical food comprising one or more compounds disclosed herein, one or more compounds that modulate the general cellular stress response, one or more histone deacetylase inhibitors, Class I histone deacetylase inhibitors, and or Class II histone deacetylase inhibitors. For example, in an aspect, the medical food comprises 4-phenylbutyrate. In an aspect, the medical food comprises sodium butyrate. In an aspect, the medical food comprises trichostatin A. In an aspect, the medical food comprises a combination of 4-phenylbutyrate, sodium butyrate, and/or trichostatin A. For example, the medical food comprises a combination comprising phenylbutyrate and sodium butyrate. In an aspect, the medical food comprises a combination comprising phenylbutyrate and trichostatin A. In an aspect, the medical food comprises a combination comprising sodium butyrate and trichostatin A. In an aspect, the medical food comprises a combination comprising phenylbutyrate, sodium butyrate, and trichostatin A. In an aspect, the medical food comprises hydroxyurea. In an aspect, the medical food comprises one or more Class II histone deacetylase inhibitors. In an aspect, the medical food comprises sulforaphane or a sulforaphane analog. In an aspect, the medical food comprises a sulforaphane dithocarbamate metabolite.

In an aspect, the medical food comprises at least one of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, a sulforaphane derivative, or a sulforaphane dithocarbamate metabolite. In an aspect, the medical food comprises a combination of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, a sulforaphane derivative, or a sulforaphane dithocarbamate metabolite. In an aspect, the medical food comprises a combination of a histone deacetylase inhibitor, such as for example, a Class I histone deacetylase inhibitor or a Class II histone deacetylase inhibitor, and one or more of the following: 4-phenylbutyrate, trichostatin A, hydroxyurea, sulforaphane, a sulforaphane derivative, or a sulforaphane analog, or a sulforaphane dithocarbamate metabolite. In an aspect, the medical food comprises a combination of 4-phenylbutyrate, trichostatin A, hydroxyurea, and sulforaphane or a sulforaphane analog.

In an aspect, the medical food comprises one or more cruciferous seeds or sprouts, or the extracts from one or more cruciferous sprouts.

In a disclosed method of treating autism or one or more autism spectrum disorders, the medical food comprises a compound that is present as a structure represented by a formula:

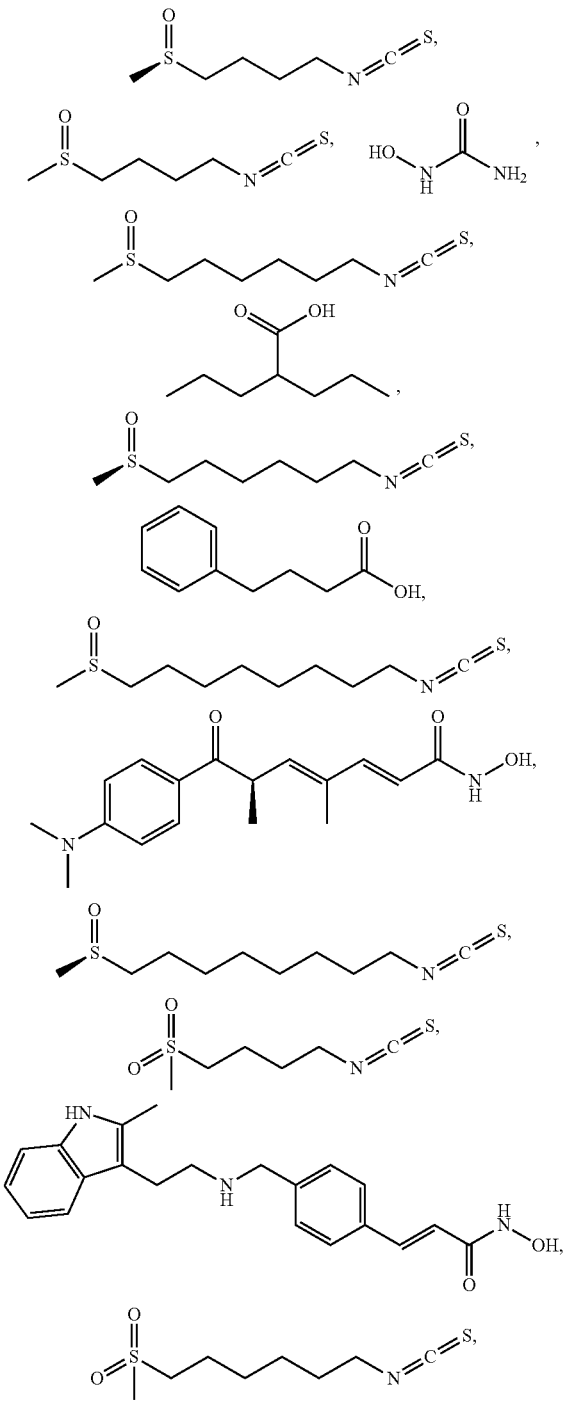

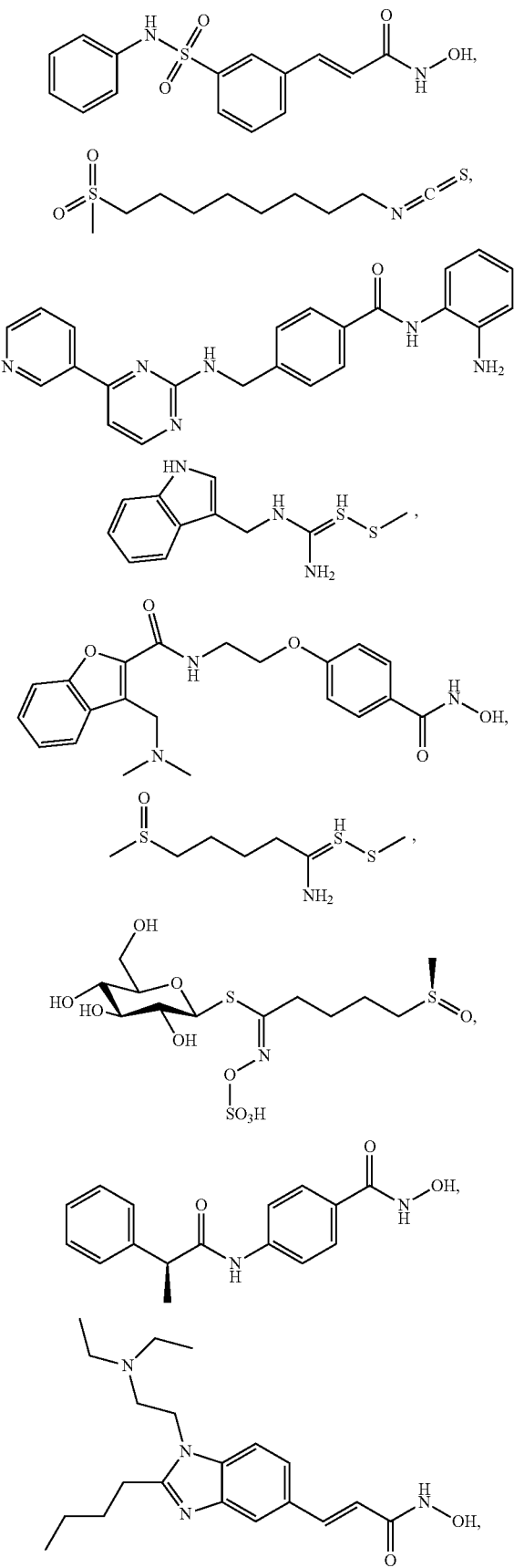

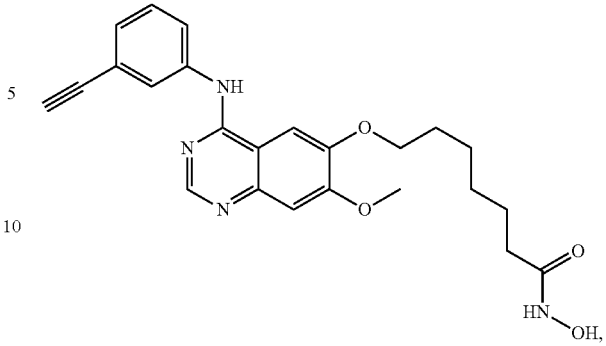

or a subgroup or pharmaceutically acceptable salt thereof.

In a disclosed method of treating autism or one or more autism spectrum disorders, a sulforaphane analog is 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3-(methylsulfonyl)cyclohexylmethylisothiocyanante, or trans-3-(methylsulfonyl)cyclohexylmethylisothiocyanante.

In a disclosed method of treating autism or one or more autism spectrum disorders, the medical food comprises excipients or diluents.

In an aspect, the disclosed medical food comprises one or more compounds that causes (i) mitochondrial biogenesis, (2) peroxisome proliferation, (3) activation of the stress proteome, or (4) transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway.

In an aspect, a medical food disclosed herein comprises compounds and compositions of the present invention, and optionally comprises enzymes for which compounds of the present invention are substrates. Medical food compositions may be taken by subjects in a delivery vehicle appropriate for the route of administration, such as capsules, topical creams, nasal sprays, injectable solutions, pastilles, sachets, and such compositions may be administered alone or in combination with other component compositions. For example, a composition may comprise compounds of the present invention in one delivery vehicle that is administered concurrently or sequentially with a second composition comprising an enzyme composition of the present invention. An enzyme composition as used herein may comprise one or more disclosed enzymes for altering precursor molecules to result in more active compounds, and may comprise co-factors, co-enzymes, and/or other enzymes in a conversion pathway.

vii) Dietary Supplements

The present invention comprises methods and compositions comprising compounds disclosed herein for the treatment of autism and autism spectrum disorders that are formulated as dietary or nutritional supplements. A dietary supplement, also known as food supplement or nutritional supplement, is a preparation intended to supplement the diet and provide compounds, such as those disclosed herein or such as vitamins, minerals, fiber, fatty acids, or amino acids, that may be missing from normal dietary sources or may not be consumed in sufficient quantities in a person's diet. Some countries define dietary supplements as foods, while in others they are defined as drugs or natural health products. A dietary supplement may be provided in delivery vehicles suitable for administration, or may be added to foods, liquids, solids, drinks, water, or other ingestible or nutritious compositions that subjects can eat or drink.

Disclosed herein are dietary supplements used to treat autism. Disclosed herein are dietary supplements used to treat one or more autism spectrum disorders.

A composition of the present invention comprises a dietary supplement comprising one or more compounds disclosed herein, one or more compounds that modulate the general cellular stress response, one or more histone deacetylase inhibitors, Class I histone deacetylase inhibitors, and or Class II histone deacetylase inhibitors. In an aspect, a dietary supplement comprises one or more Class I histone deacetylase inhibitors. For example, in an aspect, a dietary supplement comprises 4-phenylbutyrate. In an aspect, a dietary supplement comprises sodium butyrate. In an aspect, a dietary supplement comprises trichostatin A. In an aspect, a dietary supplement comprises a combination of 4-phenylbutyrate, sodium butyrate, and/or trichostatin A. For example, a dietary supplement comprises a combination comprising phenylbutyrate and sodium butyrate. In an aspect, the dietary supplement comprises a combination comprising phenylbutyrate and trichostatin A. In an aspect, the dietary supplement comprises a combination comprising sodium butyrate and trichostatin A. In an aspect, the dietary supplement comprises a combination comprising phenylbutyrate, sodium butyrate, and trichostatin A. In an aspect, the dietary supplement comprises hydroxyurea. In an aspect, the dietary supplement comprises one or more Class II histone deacetylase inhibitors. In an aspect, the dietary supplement comprises sulforaphane or a sulforaphane analog or derivative. In an aspect, the dietary supplement comprises a sulforaphane dithocarbamate metabolite.

In an aspect, the dietary supplement comprises at least one of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, or a sulforaphane dithocarbamate metabolite. In an aspect, the dietary supplement comprises a combination of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, or a sulforaphane dithocarbamate metabolite. In an aspect, the dietary supplement comprises a combination of a histone deacetylase inhibitor, such as for example, a Class I histone deacetylase inhibitor or a Class II histone deacetylase inhibitor, and one or more of the following: 4-phenylbutyrate, trichostatin A, hydroxyurea, sulforaphane or a sulforaphane analog, or a sulforaphane dithocarbamate metabolite. In an aspect, the dietary supplement comprises a combination of 4-phenylbutyrate, trichostatin A, hydroxyurea, and sulforaphane or a sulforaphane analog.

A composition of the present invention comprises a dietary supplement comprising a compound that is present as a structure represented by a formula:

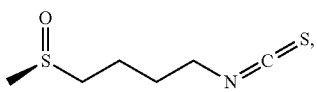

-continued

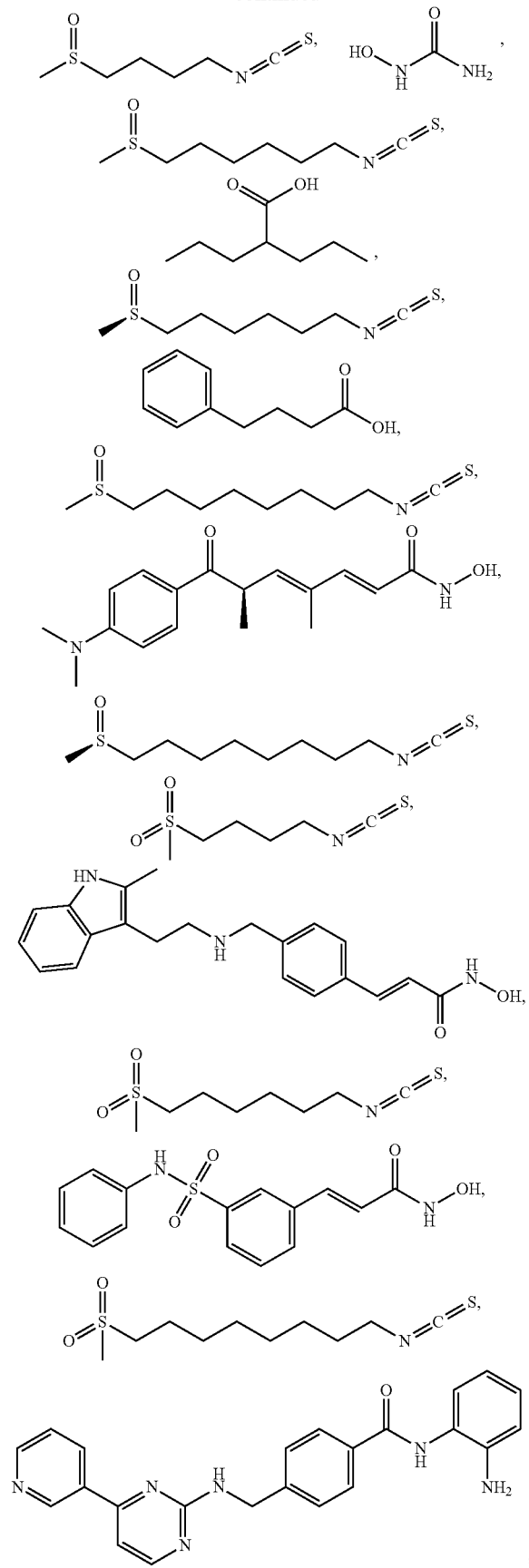

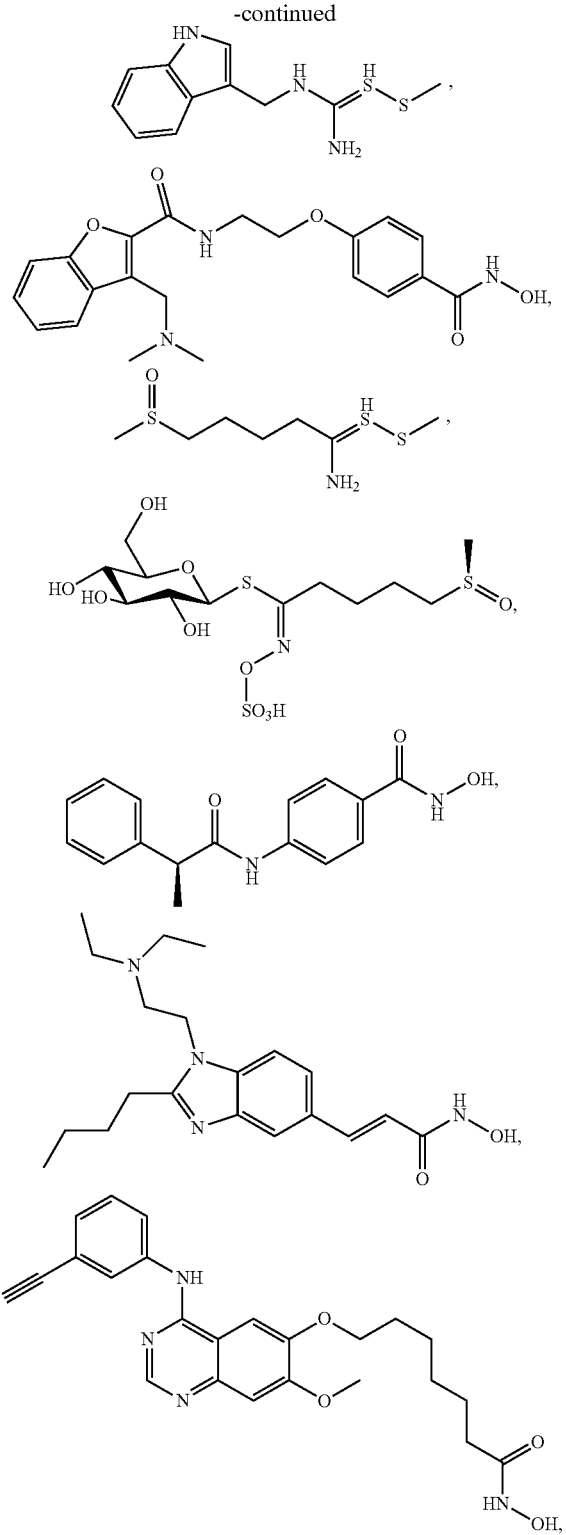

or a subgroup or a pharmaceutically acceptable salt thereof.

In a disclosed method of treating autism or one or more autism spectrum disorders, the dietary supplement comprises excipients or diluents, or other components routinely used in formulating a dietary supplement.

In an aspect, the disclosed dietary supplement comprises one or more cruciferous sprouts, or the extracts from one or more cruciferous plant sources.

In an aspect, a disclosed dietary supplement comprises one or more compounds that causes (i) mitochondrial biogenesis, (2) peroxisome proliferation, (3) activation of the stress proteome, or (4) transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway.

In an aspect, the dietary supplements disclosed herein comprise compounds and compositions of the present invention, and optionally comprises enzyme compositions that alter compounds of the present invention. Dietary supplements compositions may be taken by subjects in a delivery vehicle appropriate for the route administration, such as capsules, topical creams, nasal sprays, injectable solutions, pastilles, sachets, and such compositions may be administered alone or in combination with other component compositions. For example, in a method, one composition may comprise compounds of the present invention in one delivery vehicle that is administered concurrently or sequentially with a second composition comprising an enzyme composition of the present invention.

B. Methods of Treating Autism

Disclosed herein are methods of treating autism.

Disclosed herein is a method of treating autism comprising administering to a subject diagnosed with autism an effective amount of a pharmaceutical composition, wherein the composition comprises a compound that induces a general cellular stress response in at least one cell of the subject; and allowing the subject to return to homeostasis that existed prior to administering the compound.

Disclosed herein is method of treating autism comprising administering to at least one cell of a subject diagnosed with autism an effective amount of a pharmaceutical composition comprising a compound that induces a general cellular stress response in the at least one cell of the subject; and allowing the cell to return to homeostasis that existed prior to administering the compound.

Disclosed herein is a method of treating autism comprising administering to a subject diagnosed with autism an effective amount of a pharmaceutical composition that modulates measurable effects of behavioral symptoms.

Disclosed herein is a method of treating autism comprising administering to a subject diagnosed with autism an effective amount of a pharmaceutical composition that modulates social responsiveness of the subject treated. The person skilled in the art is familiar with the social responsiveness of a subject with autism or autism spectrum disorder as discussed in Constantino et al., 2003 (J Autism Devel Disorders, 33: 427-433, which discusses the Social Responsiveness Scale or SRS—a well-validated measure of autistic traits).

In a disclosed method of treating autism, the subject is male or female. In an aspect, the subject does not denote a particular age or sex. Thus, adult and newborn subjects, as well as fetuses, whether male or female, are intended to be covered. In an aspect, the subject is a mammal.

In a disclosed method of treating autism, improvements in behavioral symptoms comprise one or more of the following: a decrease in (i) irritability, (ii) hyperactivity, (iii) stereotypy, and/or (iv) inappropriate speech. In an aspect, improvements in behavioral symptoms include comprise a decrease in (i) irritability, (ii) hyperactivity, (iii) stereotypy, and (iv) inappropriate speech. In an aspect, improvements in behavioral symptoms comprise a combination of two or more of a decrease in (i) irritability, (ii) hyperactivity, (iii) stereotypy, and/or (iv) inappropriate speech. For example, in an aspect, improvements in behavioral symptoms comprise a decrease in irritability and hyperactivity. For example, in an aspect, improvements in behavioral symptoms comprise a decrease in irritability and stereotypy. For example, in an aspect, improvements in behavioral symptoms comprise a decrease in irritability and inappropriate speech. For example, in an aspect, improvements in behavioral symptoms comprise a decrease in hyperactivity and inappropriate speech. For example, in an aspect, improvements in behavioral symptoms comprise a decrease in stereotypy and inappropriate speech. For example, in an aspect, improvements in behavioral symptoms comprise a decrease in irritability, hyperactivity, and stereotypy. For example, in an aspect, improvements in behavioral symptoms comprise a decrease in irritability, hyperactivity, and inappropriate speech. For example, in an aspect, improvements in behavioral symptoms comprise a decrease in irritability, stereotypy, and inappropriate speech. For example, in an aspect, improvements in behavioral symptoms comprise a decrease in hyperactivity, stereotypy, and inappropriate speech. As known to the person skilled in the art, behavioral symptoms in autism and autism spectrum disorders and improvements thereof are discussed in Aman et al., 1985.

In a disclosed method of treating autism, in at least one cell of the subject, the stress proteome is stimulated. In a disclosed method of treating autism, in at least one cell of the subject, increased nitrous oxide production is measured. In a disclosed method of treating autism, in at least one cell of the subject, stress-sensing organelles are increased from an amount prior to the administration of the composition. A stress-sensing organelle can be a mitochondrion or a peroxisome. In an aspect, a stress-sensing organelle is a mitochondrion. In an aspect, a stress-sensing organelle is a peroxisome.

In a disclosed method of treating autism, a general cellular stress response of a disclosed method of treating autism comprises at least one of the following: (1) mitochondrial biogenesis, (2) peroxisome proliferation, (3) activation of the stress proteome, or (4) transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, a general cellular stress response comprises more than one of the following: (1) mitochondrial biogenesis, (2) peroxisome proliferation, (3) activation of the stress proteome, or (4) transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway.

For example, in an aspect, a combination comprises mitochondrial biogenesis and peroxisome proliferation. In an aspect, a combination comprises mitochondrial biogenesis and activation of the stress proteome. In an aspect, a combination comprises mitochondrial biogenesis and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, a combination comprises peroxisome proliferation and activation of the stress proteome.

In an aspect, a combination comprises peroxisome proliferation and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, a combination comprises activation of the stress proteome and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises mitochondrial biogenesis, peroxisome proliferation, and activation of the stress proteome. In an aspect, a combination comprises mitochondrial biogenesis, peroxisome proliferation, transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, a combination comprises mitochondrial biogenesis, activation of the stress proteome, and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises peroxisome proliferation, activation of the stress proteome, and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway.

In a disclosed method of treating autism, genes for heat shock proteins can be genes for heat shock protein 40, 70, and/or 90 family members. In an aspect, the genes for heat shock proteins comprise genes for heat shock protein 40 family members. In an aspect, the genes for heat shock proteins comprise genes for heat shock protein 70 family members. In an aspect, the genes for heat shock proteins comprise genes for heat shock protein 90 family members. In an aspect, the genes for heat shock proteins comprise genes for heat shock protein 40 and 70 family members. In an aspect, the genes for heat shock proteins comprise genes for heat shock protein 40 and 90 family members. In an aspect, the genes for heat shock proteins comprise genes for heat shock protein 70 and 90 family members. In an aspect, the genes for heat shock proteins comprise genes for heat shock protein 40, heat shock protein 70, and heat shock protein 90 family members.

In a disclosed method of treating autism, unfolded protein genes may comprise glucose regulated protein 78 (BIP), protein kinase RNA-like endoplasmic reticulum kinase, (PERK), inositol requiring 1 (IRE1), and/or activating transcription factor 6. In an aspect, the unfolded protein gene is glucose regulated protein 78 (BIP). In an aspect, the unfolded protein gene is PERK. In an aspect, the unfolded protein gene is inositol requiring 1 (IRE1). In an aspect, the unfolded protein gene is transcription factor 6.

In an aspect of a disclosed method of treating autism, the unfolded protein genes comprise a combination of glucose regulated protein 78 (BIP), protein kinase RNA-like endoplasmic reticulum kinase (PERK), inositol requiring 1 (IRE1), and/or activating transcription factor 6. In an aspect, the combination of unfolded protein genes comprises glucose regulated protein 78 (BIP) and PERK. In an aspect, the combination of unfolded protein genes comprises glucose regulated protein 78 (BIP) and inositol requiring 1 (IRE1). In an aspect, the combination of unfolded protein genes comprises glucose regulated protein 78 (BIP) and activating transcription factor 6. In an aspect, the combination of unfolded protein genes comprises PERK and inositol requiring 1 (IRE1). In an aspect, the combination of unfolded protein genes comprises PERK and activating transcription factor 6. In an aspect, the combination of unfolded protein genes comprise glucose regulated protein 78 (BIP), PERK, and inositol requiring 1 (IRE1). In an aspect of a disclosed method of treating autism, the unfolded protein genes comprise a combination of glucose regulated protein 78 (BIP), PERK, and activating transcription factor 6. In an aspect of a disclosed method of treating autism, the unfolded protein genes comprise a combination of glucose regulated protein 78 (BIP), inositol requiring 1 (IRE1), and activating transcription factor 6. In an aspect of a disclosed method of treating autism, the unfolded protein genes comprise a combination of PERK, inositol requiring 1 (IRE1), and activating transcription factor 6.

In a disclosed method of treating autism, autophagic response genes may comprise beclin-1 (BCN1), autophagy protein 5 (ATG5), and/or microtubule-associated protein 1 light chain 3 (LC3 or APG8). In an aspect, the autophagic response gene is beclin-1 (BCN1). In an aspect, the autophagic response gene is autophagy protein 5 (ATG5). In an aspect, the autophagic response gene is microtubule-associated protein 1 light chain 3 (LC3 or APG8). In an aspect, the autophagic response genes comprise a combination of beclin-1 (BCN1), autophagy protein 5 (ATG5), and/or microtubule-associated protein 1 light chain 3 (LC3 or APG8). In an aspect, the combination comprises beclin-1 (BCN1 and autophagy protein 5 (ATG5). In an aspect, the combination comprises beclin-1 (BCN1) and microtubule-associated protein 1 light chain 3 (LC3 or APG8). In an aspect, the combination comprises autophagy protein 5 (ATG5) and microtubule-associated protein 1 light chain 3 (LC3 or APG8).

In a disclosed method of treating autism, antioxidant response genes may comprise expression of nuclear factor erythroid 2-like 2 (NFE2L2), heme oxygenase 1 (HMOX1), and superoxide dismutase 2 (SOD2). In an aspect, the antioxidant response gene is nuclear factor erythroid 2-like 2 (NFE2L2). In an aspect, the antioxidant response gene is heme oxygenase 1 (HMOX1). In an aspect, the antioxidant response gene is superoxide dismutase 2 (SOD2). In an aspect, the antioxidant response genes comprise expression of a combination of nuclear factor erythroid 2-like 2 (NFE2L2), heme oxygenase 1 (HMOX1), and/or superoxide dismutase 2 (SOD2). In an aspect, the antioxidant response genes comprise expression of a combination of nuclear factor erythroid 2-like 2 (NFE2L2) and heme oxygenase 1 (HMOX1). In an aspect, the antioxidant response genes comprise expression of a combination of nuclear factor erythroid 2-like 2 (NFE2L2 and superoxide dismutase 2 (SOD2). In an aspect, the antioxidant response genes comprise expression of a combination of heme oxygenase 1 (HMOX1) and superoxide dismutase 2 (SOD2). In an aspect, the antioxidant response genes comprise expression of a combination of nuclear factor erythroid 2-like 2 (NFE2L2), heme oxygenase 1 (HMOX1), and superoxide dismutase 2 (SOD2).

In a disclosed method of treating autism, at least one cell of the subject is located in the brain of the subject. In an aspect, at least one cell of the subject is not in the brain of the subject. In an aspect, a general stress response occurs in all cells of the subject, but to differing degrees. In an aspect, the degree to which a cell demonstrates a general stress response depends on the specific tissue and cell type. For example, in an aspect, cells in the subject's brain are sensitive due to a high energy requirement and mitochondrial activity.

In a disclosed method of treating autism, a composition comprises one or more histone deacetylase inhibitors. In a disclosed method of treating autism, a composition comprises one or more Class I histone deacetylase inhibitors. For example, in an aspect, the composition comprises 4-phenylbutyrate. In an aspect, the composition comprises sodium butyrate. In an aspect, the composition comprises trichostatin A. In an aspect, the composition comprises a combination of 4-phenylbutyrate, sodium butyrate, and/or trichostatin A. For example, the composition comprises a combination comprising phenylbutyrate and sodium butyrate. In an aspect, the composition comprises a combination comprising phenylbutyrate and trichostatin A. In an aspect, the composition comprises a combination comprising sodium butyrate and trichostatin A. In an aspect, the composition comprises a combination comprising phenylbutyrate, sodium butyrate, and trichostatin A.

In a disclosed method of treating autism, a composition comprises hydroxyurea.

In a disclosed method of treating autism, a composition comprises one or more Class II histone deacetylase inhibitors.

In a disclosed method of treating autism, a composition comprises sulforaphane or a sulforaphane derivative or analog, or combinations thereof.

In a disclosed method of treating autism, the composition comprises a sulforaphane dithocarbamate metabolite.

In a disclosed method of treating autism, a composition comprises at least one of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, or a sulforaphane dithocarbamate metabolite. In an aspect, a composition comprises a combination of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, or a sulforaphane dithocarbamate metabolite. In an aspect, the composition comprises a combination of a histone deacetylase inhibitor, such as for example, a Class I histone deacetylase inhibitor or a Class II histone deacetylase inhibitor, and one or more of the following: 4-phenylbutyrate, trichostatin A, hydroxyurea, sulforaphane or a sulforaphane analog, or a sulforaphane dithocarbamate metabolite. In an aspect, the composition comprises a combination of 4-phenylbutyrate, trichostatin A, hydroxyurea, and sulforaphane or a sulforaphane analog.

In a disclosed method of treating autism, the composition comprises a compound that is present as a structure represented by a formula:

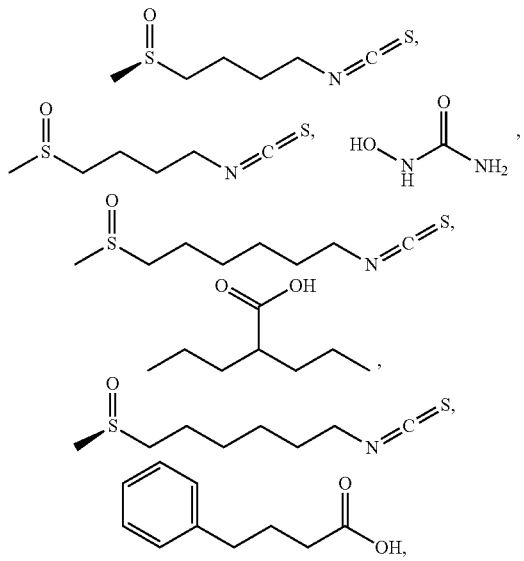

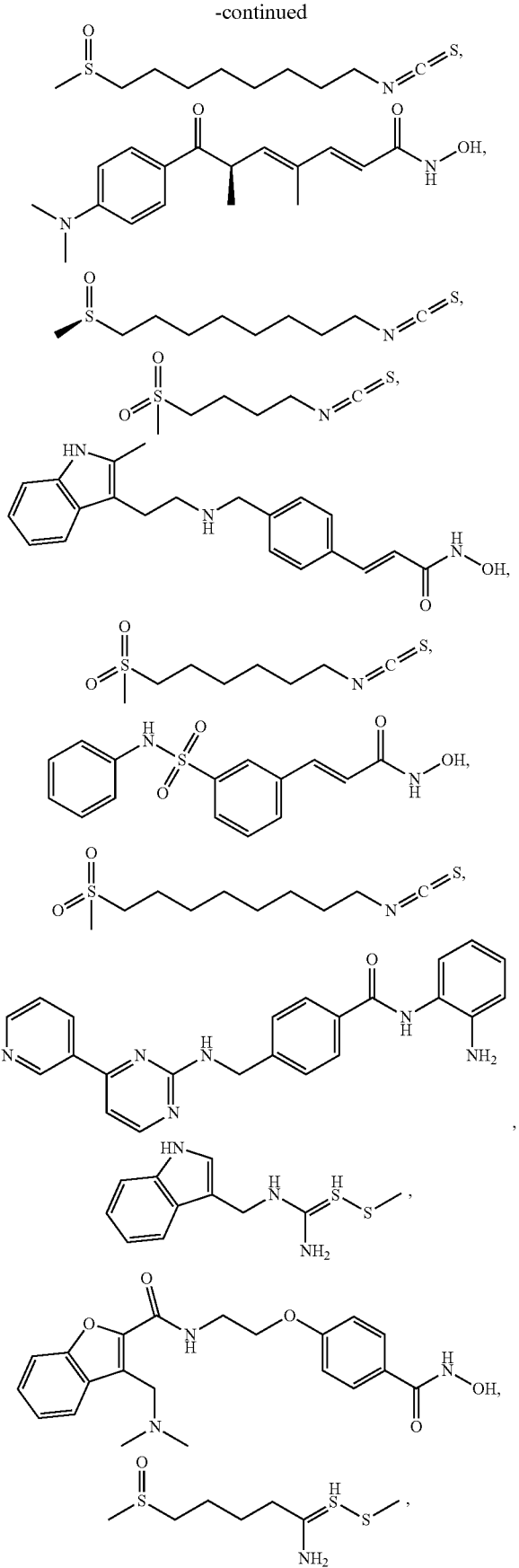
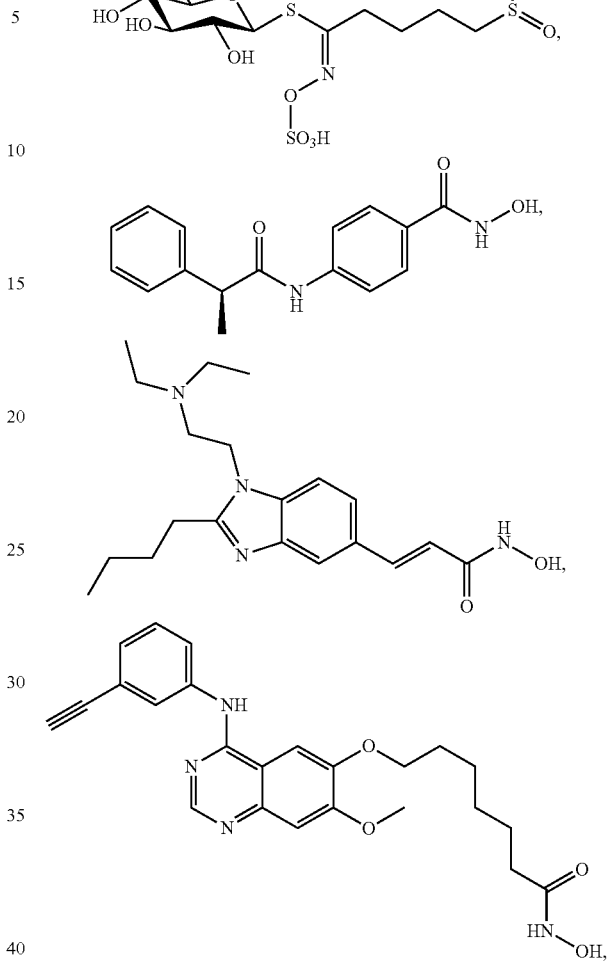

or a subgroup or pharmaceutically acceptable salt thereof.

In a disclosed method of treating autism, the composition further comprises pharmaceutical excipients or diluents, or components of formulations used in delivery vehicles for appropriate administration of the composition.

In a disclosed method of treating autism, the composition is administered orally, topically, by injection, intravascular, subcutaneously, intramuscularly, nasally, or by other known routes of administration. In a disclosed method of treating autism, the composition is administered one or more times. For example, in an aspect, the composition is administered at least one time per day. In an aspect, the composition is administered continuously. In an aspect, the composition is administered intermittently. In an aspect, administration can be repeated, for example, once per day, or two or more times per day, or once per week, or two or more times per week, or every other week, or once per month, or one or more times per month, or every other day, or every other week, or every over month, or every other year, so forth and so on.

A disclosed method of treating autism can further comprise evaluating the progression of a subject's neurological disease or neurological disorder, such as, for example, autism or one or more autism spectrum disorders. A clinician (e.g., a physician) or researcher can evaluating the subject at scheduled times. For example, in an aspect, the acquisition of data for a human subject can be performed periodically, wherein the scheduled times occur at regular intervals, such as every 3 months, 6 months, 9 months, or every year, every other year, every 5 years, every 10 years for the life of the subject. In an aspect, the scheduled times need not be periodic. For another example, in an aspect, the acquisition of data for a non-human subject can be carried out periodically at scheduled times spaced at regular intervals, such as every week, every other week, every month, every other month, every 3 months, every 6 months, every 9 months, every year, every other year for the life of the non-human subject.

C. Methods of Treating Autism Spectrum Disorder

Disclosed herein are methods of treating one or more autism spectrum disorders.

Disclosed herein is a method of treating one or more autism spectrum disorders comprising administering to a subject diagnosed with one or more autism spectrum disorders an effective amount of a pharmaceutical composition comprising a compound that induces a general cellular stress response in at least one cell of the person.

Disclosed herein is a method of treating one or more autism spectrum disorders comprising administering to a subject diagnosed with one or more autism spectrum disorders an effective amount of a pharmaceutical composition that modulates measurable effects of behavioral symptoms.

Disclosed herein is a method of treating one or more autism spectrum disorders comprising administering to a subject diagnosed with one or more autism spectrum disorders an effective amount of a pharmaceutical composition that modulates social responsiveness of the subject treated. The person skilled in the art is familiar with the social responsiveness of a subject with autism or autism spectrum disorder as discussed in Constantino et al., 2003 (J Autism Devel Disorders, 33: 427-433, which discusses the Social Responsiveness Scale or SRS—a well-validated measure of autistic traits).

In a disclosed method of treating one or more autism spectrum disorders, the subject is male or female. In an aspect, the subject does not denote a particular age or sex. Thus, adult and newborn subjects, as well as fetuses, whether male or female, are intended to be covered. In an aspect, the subject is a mammal.

In a disclosed method of treating one or more autism spectrum disorders, in the at least one cell of the subject, the stress proteome is stimulated. In a disclosed method of treating autism, in the at least one cell of the subject, increased nitrous oxide production is measured.

In a disclosed method of treating one or more autism spectrum disorders, in the at least one cell of the subject, stress-sensing organelles are increased from an amount prior to the administration of the composition. A stress-sensing organelle can be a mitochondrion or a peroxisome. In an aspect, a stress-sensing organelle is a mitochondrion. In an aspect, a stress-sensing organelle is a peroxisome.

In a disclosed method of treating one or more autism spectrum disorders, a general cellular stress response of a disclosed method of treating autism comprises at least one of the following: (1) mitochondrial biogenesis, (2) peroxisome proliferation, (3) activation of the stress proteome, or (4) transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, a general cellular stress response comprises more than one of the following: (1) mitochondrial biogenesis, (2) peroxisome proliferation, (3) activation of the stress proteome, or (4) transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway.

For example, in an aspect, a combination comprises mitochondrial biogenesis and peroxisome proliferation. In an aspect, the combination comprises mitochondrial biogenesis and activation of the stress proteome. In an aspect, the combination comprises mitochondrial biogenesis and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises peroxisome proliferation and activation of the stress proteome.

In an aspect, the combination comprises peroxisome proliferation and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises activation of the stress proteome and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises mitochondrial biogenesis, peroxisome proliferation, and activation of the stress proteome. In an aspect, the combination comprises mitochondrial biogenesis, peroxisome proliferation, transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises mitochondrial biogenesis, activation of the stress proteome, and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises peroxisome proliferation, activation of the stress proteome, and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway.

In a disclosed method of treating one or more autism spectrum disorders, genes for heat shock proteins can be genes for heat shock protein 40, 70, and/or 90 family members. In an aspect, the genes for heat shock proteins comprise genes for heat shock protein 40 family members. In an aspect, the genes for heat shock proteins comprise genes for heat shock protein 70 family members. In an aspect, the genes for heat shock proteins comprise genes for heat shock protein 90 family members. In an aspect, the genes for heat shock proteins comprise genes for heat shock protein 40 and 70 family members. In an aspect, the genes for heat shock proteins comprise genes for heat shock protein 40 and 90 family members. In an aspect, the genes for heat shock proteins comprise genes for heat shock protein 70 and 90 family members. In an aspect, the genes for heat shock proteins comprise genes for heat shock protein 40, heat shock protein 70, and heat shock protein 90 family members.

In a disclosed method of treating one or more autism spectrum disorders, unfolded protein genes comprise glucose regulated protein 78 (BIP), protein kinase RNA-like endoplasmic reticulum kinase (PERK), inositol requiring 1 (IRE1), and/or activating transcription factor 6. In an aspect, the unfolded protein gene is glucose regulated protein 78 (BIP). In an aspect, the unfolded protein gene is PERK. In an aspect, the unfolded protein gene is inositol requiring 1 (IRE1). In an aspect, the unfolded protein gene is transcription factor 6.

In an aspect of a disclosed method of treating one or more autism spectrum disorders, the unfolded protein genes comprise a combination of glucose regulated protein 78 (BIP), protein kinase RNA-like endoplasmic reticulum kinase (PERK), inositol requiring 1 (IRE1), and/or activating transcription factor 6. In an aspect, the combination of unfolded protein genes comprises glucose regulated protein 78 (BIP) and PERK. In an aspect, the combination of unfolded protein genes comprises glucose regulated protein 78 (BIP) and inositol requiring 1 (IRE1). In an aspect, the combination of unfolded protein genes comprises glucose regulated protein 78 (BIP) and activating transcription factor 6. In an aspect, the combination of unfolded protein genes comprises PERK and inositol requiring 1 (IRE1). In an aspect, the combination of unfolded protein genes comprises PERK and activating transcription factor 6. In an aspect, the combination of unfolded protein genes comprise glucose regulated protein 78 (BIP), PERK, and inositol requiring 1 (IRE1). In an aspect of a disclosed method of treating autism, the unfolded protein genes comprise a combination of glucose regulated protein 78 (BIP), PERK, and activating transcription factor 6. In an aspect of a disclosed method of treating autism, the unfolded protein genes comprise a combination of glucose regulated protein 78 (BIP), inositol requiring 1 (IRE1), and activating transcription factor 6. In an aspect of a disclosed method of treating autism, the unfolded protein genes comprise a combination of PERK, inositol requiring 1 (IRE1), and activating transcription factor 6.

In a disclosed method of treating one or more autism spectrum disorders, the autophagic response genes comprise beclin-1 (BCN1), autophagy protein 5 (ATG5), and/or microtubule-associated protein 1 light chain 3 (LC3 or APG8). In an aspect, the autophagic response gene is beclin-1 (BCN1). In an aspect, the autophagic response gene is autophagy protein 5 (ATG5). In an aspect, the autophagic response gene is microtubule-associated protein 1 light chain 3 (LC3 or APG8). In an aspect, the autophagic response genes comprise a combination of beclin-1 (BCN1), autophagy protein 5 (ATG5), and/or microtubule-associated protein 1 light chain 3 (LC3 or APG8). In an aspect, the combination comprises beclin-1 (BCN1 and autophagy protein 5 (ATG5). In an aspect, the combination comprises beclin-1 (BCN1) and microtubule-associated protein 1 light chain 3 (LC3 or APG8). In an aspect, the combination comprises autophagy protein 5 (ATG5) and microtubule-associated protein 1 light chain 3 (LC3 or APG8).

In a disclosed method of treating one or more autism spectrum disorders, the antioxidant response genes comprise expression of nuclear factor erythroid 2-like 2 (NFE2L2), heme oxygenase 1 (HMOX1), and superoxide dismutase 2 (SOD2). In an aspect, the antioxidant response gene is nuclear factor erythroid 2-like 2 (NFE2L2). In an aspect, the antioxidant response gene is heme oxygenase 1 (HMOX1). In an aspect, the antioxidant response gene is superoxide dismutase 2 (SOD2). In an aspect, the antioxidant response genes comprise expression of a combination of nuclear factor erythroid 2-like 2 (NFE2L2), heme oxygenase 1 (HMOX1), and/or superoxide dismutase 2 (SOD2). In an aspect, the antioxidant response genes comprise expression of a combination of nuclear factor erythroid 2-like 2 (NFE2L2) and heme oxygenase 1 (HMOX1). In an aspect, the antioxidant response genes comprise expression of a combination of nuclear factor erythroid 2-like 2 (NFE2L2 and superoxide dismutase 2 (SOD2). In an aspect, the antioxidant response genes comprise expression of a combination of heme oxygenase 1 (HMOX1) and superoxide dismutase 2 (SOD2). In an aspect, the antioxidant response genes comprise expression of a combination of nuclear factor erythroid 2-like 2 (NFE2L2), heme oxygenase 1 (HMOX1), and superoxide dismutase 2 (SOD2).

In a disclosed method of treating one or more autism spectrum disorders, the at least one cell of the subject is located in the brain of the subject. In an aspect, the at least one cell of the subject is not in the brain of the subject. In an aspect, a general stress response occurs in all cells of the subject, but to differing degrees. In an aspect, the degree to which a cell demonstrates a general stress response depends on the specific tissue and cell type. For example, in an aspect, cells in the subject's brain are especially sensitive due to a high energy requirement and mitochondrial activity.

In a disclosed method of treating one or more autism spectrum disorders, the composition comprises one or more Class I histone deacetylase inhibitors. For example, in an aspect, the composition comprises 4-phenylbutyrate. In an aspect, the composition comprises sodium butyrate. In an aspect, the composition comprises trichostatin A. In an aspect, the composition comprises a combination of 4-phenylbutyrate, sodium butyrate, and/or trichostatin A. For example, the composition comprises a combination comprising phenylbutyrate and sodium butyrate. In an aspect, the composition comprises a combination comprising phenylbutyrate and trichostatin A. In an aspect, the composition comprises a combination comprising sodium butyrate and trichostatin A. In an aspect, the composition comprises a combination comprising phenylbutyrate, sodium butyrate, and trichostatin A.

In a disclosed method of treating one or more autism spectrum disorders, the composition comprises hydroxyurea.

In a disclosed method of treating one or more autism spectrum disorders, the composition comprises one or more Class II histone deacetylase inhibitors.

In a disclosed method of treating one or more autism spectrum disorders, the composition comprises sulforaphane or a sulforaphane derivative or analog.

In a disclosed method of treating one or more autism spectrum disorders, the composition comprises a sulforaphane dithocarbamate metabolite.

In a disclosed method of treating one or more autism spectrum disorders, the composition comprises at least one of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, or a sulforaphane dithocarbamate metabolite. In an aspect, the composition comprises a combination of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, or a sulforaphane dithocarbamate metabolite. In an aspect, the composition comprises a combination of a histone deacetylase inhibitor, such as for example, a Class I histone deacetylase inhibitor or a Class II histone deacetylase inhibitor, and one or more of the following: 4-phenylbutyrate, trichostatin A, hydroxyurea, sulforaphane or a sulforaphane analog, or a sulforaphane dithocarbamate metabolite. In an aspect, the composition comprises a combination of 4-phenylbutyrate, trichostatin A, hydroxyurea, and sulforaphane or a sulforaphane analog.

In a disclosed method of treating one or more autism spectrum disorders, the composition comprises a compound that is present as a structure represented by a formula:
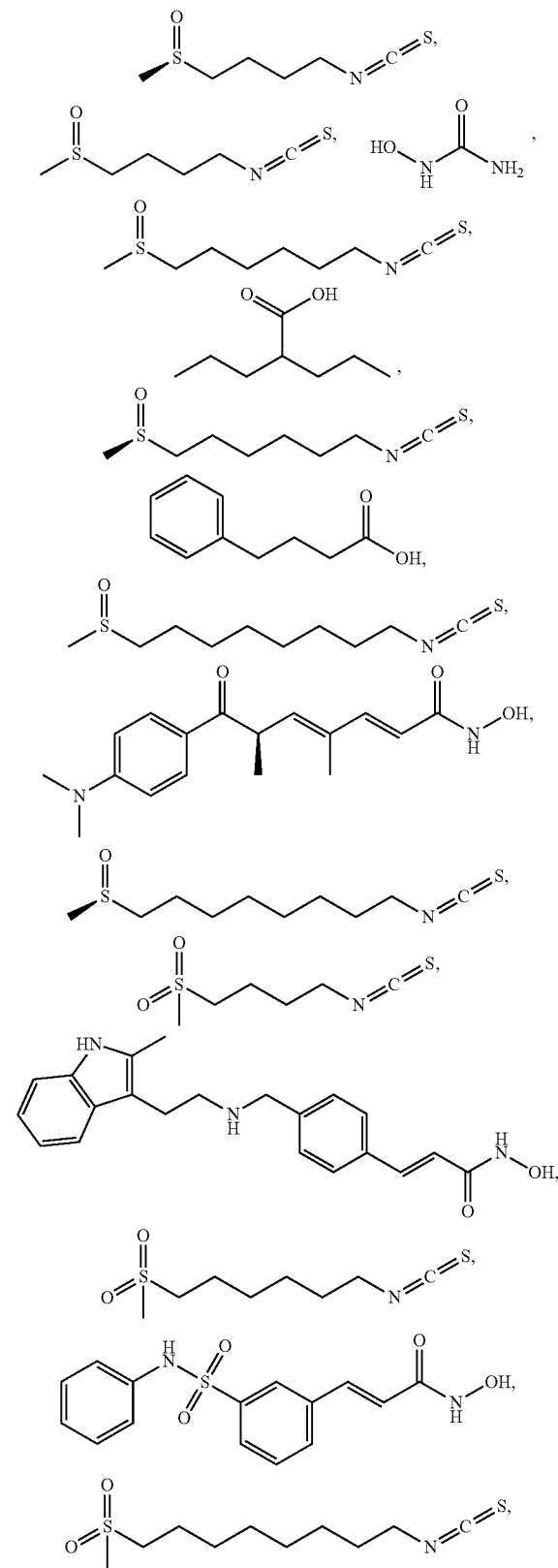
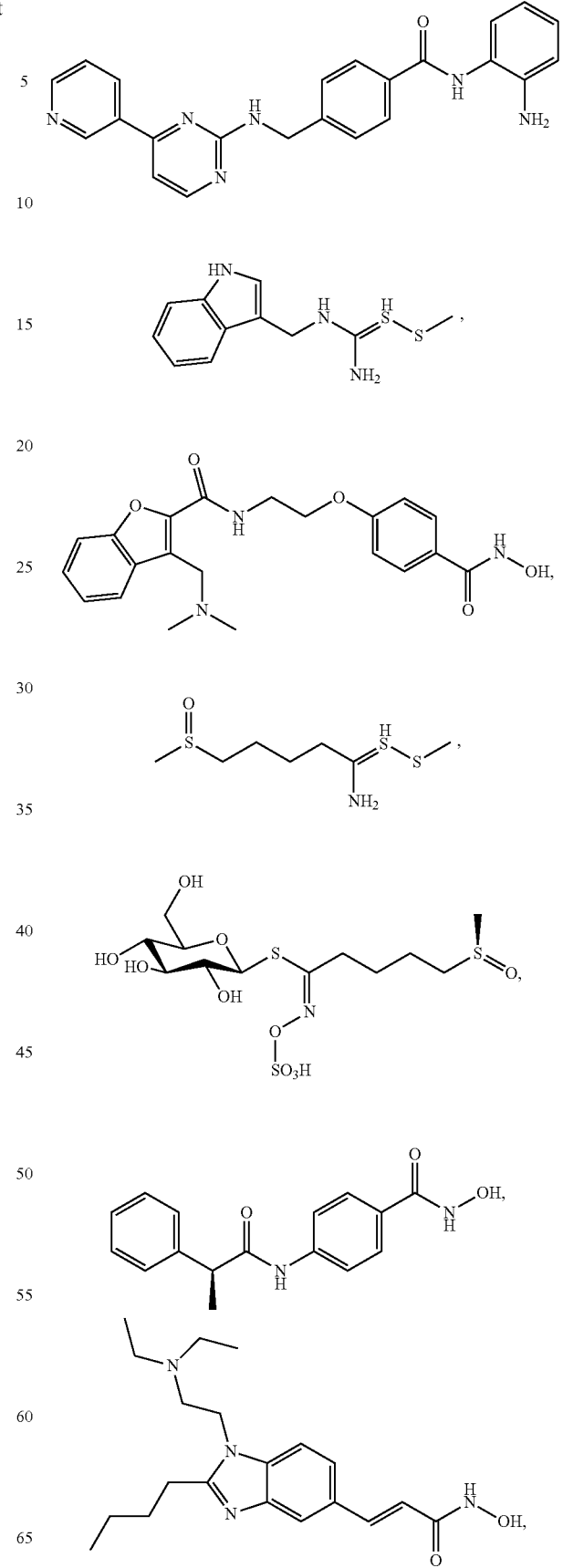

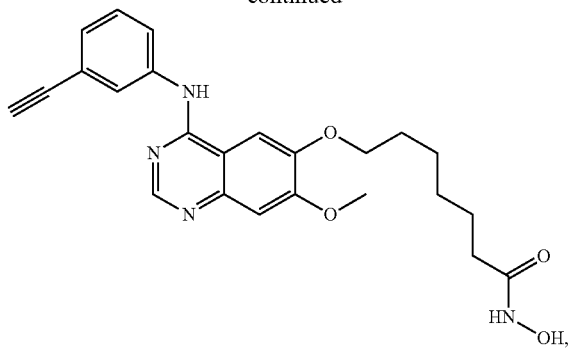

or a subgroup or pharmaceutically acceptable salt thereof.

In a disclosed method of treating one or more autism spectrum disorders, the composition further comprises pharmaceutical excipients or diluents, or components of formulations used in delivery vehicles for appropriate administration of the composition.

In a disclosed method of treating one or more autism spectrum disorders, the composition is administered orally, topically, by injection, nasally, or by other known routes of administration.

In a disclosed method of treating one or more autism spectrum disorders, the composition is administered one or more times. For example, in an aspect, the composition is administered at least one time per day. In an aspect, the composition is administered continuously. In an aspect, the composition is administered intermittently. In an aspect, administration can be repeated, for example, once per day, or two or more times per day, or once per week, or two or more times per week, or every other week, or once per month, or one or more times per month, or every other day, or every other week, or every over month, or every other year, so forth and so on.

A disclosed method of treating one or more autism spectrum disorders can further comprise evaluating the progression of a subject's neurological disease or neurological disorder, such as, for example, autism or one or more autism spectrum disorders. A clinician (e.g., a physician) or researcher can evaluating the subject at scheduled times. For example, in an aspect, the acquisition of data for a human subject can be performed periodically, wherein the scheduled times occur at regular intervals, such as every 3 months, 6 months, 9 months, or every year, every other year, every 5 years, every 10 years for the life of the subject. In an aspect, the scheduled times need not be periodic. For another example, in an aspect, the acquisition of data for a non-human subject can be carried out periodically at scheduled times spaced at regular intervals, such as every week, every other week, every month, every other month, every 3 months, every 6 months, every 9 months, every year, every other year for the life of the non-human subject.

D. Methods of Determining Effectiveness of a Compound

Disclosed herein are methods of determining the effectiveness of a compound in treating autism or an autism related disorder comprising administering to a first cell an effective amount of a compound to be tested, comparing the response of the first cell with the response of an identical cell that was treated with a compound that induces a generalized stress response, and determining whether or not the tested compound induces a general cellular stress response in cells. In an aspect, the cell is a normal human fibroblast. In an aspect, the cell is XALD fibroblast. In an aspect, the cell is a K562 cell.

In a disclosed method of determining the effectiveness of a compound in treating autism or an autism related disorder, the cell is from a subject. In an aspect, the subject is male or female. In an aspect, the subject does not denote a particular age or sex. Thus, adult and newborn subjects, as well as fetuses, whether male or female, are intended to be covered. In an aspect, the subject is a mammal.

In a disclosed method of determining the effectiveness of a compound in treating autism or an autism related disorder, the stress proteome of the first cell is stimulated. In a disclosed method of determining the effectiveness of a compound in treating autism or an autism related disorder, increased nitrous oxide production is measured in the first cell.

In a disclosed method of in a disclosed method of determining the effectiveness of a compound in treating autism or an autism related disorder, stress-sensing organelles are increased in the first cell from an amount prior to the administration of the compound. A stress-sensing organelle can be a mitrochondrion or a peroxisome. In an aspect, a stress-sensing organelle is a mitochondrion. In an aspect, a stress-sensing organelle is a peroxisome.

In a disclosed method of determining the effectiveness of a compound in treating autism or an autism related disorder, a general cellular stress response comprises at least one of the following: (1) mitochondrial biogenesis, (2) peroxisome proliferation, (3) activation of the stress proteome, or (4) transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, a general cellular stress response comprises more than one of the following: (1) mitochondrial biogenesis, (2) peroxisome proliferation, (3) activation of the stress proteome, or (4) transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway.

For example, in an aspect, the combination comprises mitochondrial biogenesis and peroxisome proliferation. In an aspect, the combination comprises mitochondrial biogenesis and activation of the stress proteome. In an aspect, the combination comprises mitochondrial biogenesis and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises peroxisome proliferation and activation of the stress proteome.

In an aspect, the combination comprises peroxisome proliferation and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises activation of the stress proteome and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises mitochondrial biogenesis, peroxisome proliferation, and activation of the stress proteome. In an aspect, the combination comprises mitochondrial biogenesis, peroxisome proliferation, transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises mitochondrial biogenesis, activation of the stress proteome, and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway. In an aspect, the combination comprises peroxisome proliferation, activation of the stress proteome, and transcription and/or translation of genes and proteins encoded by (a) genes comprising heat shock and unfolded protein, (b) genes for autophagic responses, (c) genes for antioxidant responses, and (d) genes for the c-jun-N-terminal kinase pathway.

In a disclosed method of determining the effectiveness of a compound in treating autism or an autism related disorder, the genes for heat shock proteins can be genes for heat shock protein 40, 70, and/or 90 family members. In an aspect, the genes for heat shock proteins comprise genes for heat shock protein 40 family members. In an aspect, the genes for heat shock proteins comprise genes for heat shock protein 70 family members. In an aspect, the genes for heat shock proteins comprise genes for heat shock protein 90 family members. In an aspect, the genes for heat shock proteins comprise genes for heat shock protein 40 and 70 family members. In an aspect, the genes for heat shock proteins comprise genes for heat shock protein 40 and 90 family members. In an aspect, the genes for heat shock proteins comprise genes for heat shock protein 70 and 90 family members. In an aspect, the genes for heat shock proteins comprise genes for heat shock protein 40, heat shock protein 70, and heat shock protein 90 family members.

In a disclosed method of determining the effectiveness of a compound in treating autism or an autism related disorder, the unfolded protein genes comprise glucose regulated protein 78 (BIP), protein kinase RNA-like endoplasmic reticulum kinase (PERK), inositol requiring 1 (IRE1), and/or activating transcription factor 6. In an aspect, the unfolded protein gene is glucose regulated protein 78 (BIP). In an aspect, the unfolded protein gene is PERK. In an aspect, the unfolded protein gene is inositol requiring 1 (IRE1). In an aspect, the unfolded protein gene is transcription factor 6.

In a disclosed method of determining the effectiveness of a compound in treating autism or an autism related disorder, the unfolded protein genes comprise a combination of glucose regulated protein 78 (BIP), protein kinase RNA-like endoplasmic reticulum kinase (PERK), inositol requiring 1 (IRE1), and/or activating transcription factor 6. In an aspect, the combination of unfolded protein genes comprises glucose regulated protein 78 (BIP) and PERK. In an aspect, the combination of unfolded protein genes comprises glucose regulated protein 78 (BIP) and inositol requiring 1 (IRE1). In an aspect, the combination of unfolded protein genes comprises glucose regulated protein 78 (BIP) and activating transcription factor 6. In an aspect, the combination of unfolded protein genes comprises PERK and inositol requiring 1 (IRE1). In an aspect, the combination of unfolded protein genes comprises PERK and activating transcription factor 6. In an aspect, the combination of unfolded protein genes comprise glucose regulated protein 78 (BIP), PERK, and inositol requiring 1 (IRE1). In an aspect of a disclosed method of treating autism, the unfolded protein genes comprise a combination of glucose regulated protein 78 (BIP), PERK, and activating transcription factor 6. In an aspect of a disclosed method of treating autism, the unfolded protein genes comprise a combination of glucose regulated protein 78 (BIP), inositol requiring 1 (IRE1), and activating transcription factor 6. In an aspect of a disclosed method of treating autism, the unfolded protein genes comprise a combination of PERK, inositol requiring 1 (IRE1), and activating transcription factor 6.

In a disclosed method of determining the effectiveness of a compound in treating autism or an autism related disorder, the autophagic response genes comprise beclin-1 (BCN1), autophagy protein 5 (ATG5), and/or microtubule-associated protein 1 light chain 3 (LC3 or APG8). In an aspect, the autophagic response gene is beclin-1 (BCN1). In an aspect, the autophagic response gene is autophagy protein 5 (ATG5). In an aspect, the autophagic response gene is microtubule-associated protein 1 light chain 3 (LC3 or APG8). In an aspect, the autophagic response genes comprise a combination of beclin-1 (BCN1), autophagy protein 5 (ATG5), and/or microtubule-associated protein 1 light chain 3 (LC3 or APG8). In an aspect, the combination comprises beclin-1 (BCN1 and autophagy protein 5 (ATG5). In an aspect, the combination comprises beclin-1 (BCN1) and microtubule-associated protein 1 light chain 3 (LC3 or APG8). In an aspect, the combination comprises autophagy protein 5 (ATG5) and microtubule-associated protein 1 light chain 3 (LC3 or APG8).

In a disclosed method of determining the effectiveness of a compound in treating autism or an autism related disorder, the antioxidant response genes comprise expression of nuclear factor erythroid 2-like 2 (NFE2L2), heme oxygenase 1 (HMOX1), and superoxide dismutase 2 (SOD2). In an aspect, the antioxidant response gene is nuclear factor erythroid 2-like 2 (NFE2L2). In an aspect, the antioxidant response gene is heme oxygenase 1 (HMOX1). In an aspect, the antioxidant response gene is superoxide dismutase 2 (SOD2). In an aspect, the antioxidant response genes comprise expression of a combination of nuclear factor erythroid 2-like 2 (NFE2L2), heme oxygenase 1 (HMOX1), and/or superoxide dismutase 2 (SOD2). In an aspect, the antioxidant response genes comprise expression of a combination of nuclear factor erythroid 2-like 2 (NFE2L2) and heme oxygenase 1 (HMOX1). In an aspect, the antioxidant response genes comprise expression of a combination of nuclear factor erythroid 2-like 2 (NFE2L2 and superoxide dismutase 2 (SOD2). In an aspect, the antioxidant response genes comprise expression of a combination of heme oxygenase 1 (HMOX1) and superoxide dismutase 2 (SOD2). In an aspect, the antioxidant response genes comprise expression of a combination of nuclear factor erythroid 2-like 2 (NFE2L2), heme oxygenase 1 (HMOX1), and superoxide dismutase 2 (SOD2).

In a disclosed method of determining the effectiveness of a compound in treating autism or an autism related disorder, the first cell is a brain cell. In an aspect, the first cell is not a brain cell. In an aspect, a general stress response occurs in all cells of a subject, but to differing degrees. In an aspect, the degree to which a cell demonstrates a general stress response depends on the specific tissue and cell type. For example, in an aspect, a brain cell is especially sensitive due to a high energy requirement and mitochondrial activity.

In a disclosed method of determining the effectiveness of a compound in treating autism or an autism related disorder, the compound comprises a Class I histone deacetylase inhibitors. For example, in an aspect, the compound comprises 4-phenylbutyrate. In an aspect, the compound comprises sodium butyrate. In an aspect, the compound comprises trichostatin A. In an aspect, the compound comprises a combination of 4-phenylbutyrate, sodium butyrate, and/or trichostatin A. For example, the compound comprises a combination comprising phenylbutyrate and sodium butyrate. In an aspect, the compound comprises a combination comprising phenylbutyrate and trichostatin A. In an aspect, the compound comprises a combination comprising sodium butyrate and trichostatin A. In an aspect, the compound comprises a combination comprising phenylbutyrate, sodium butyrate, and trichostatin A.

In a disclosed method of determining the effectiveness of a compound in treating autism or an autism related disorder, the compound comprises hydroxyurea.

In a disclosed method of determining the effectiveness of a compound in treating autism or an autism related disorder, the compound comprises one or more Class II histone deacetylase inhibitors.

In a disclosed method of determining the effectiveness of a compound in treating autism or an autism related disorder, the compound comprises sulforaphane or a sulforaphane analog.

In a disclosed method of determining the effectiveness of a compound in treating autism or an autism related disorder, the compound comprises a sulforaphane dithocarbamate metabolite.

In a disclosed method of determining the effectiveness of a compound in treating autism or an autism related disorder, the compound comprises at least one of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, or a sulforaphane dithocarbamate metabolite. In an aspect, the composition comprises a combination of a histone deacetylase inhibitor, a Class I histone deacetylase inhibitor, a Class II histone deacetylase inhibitor, 4-phenylbutyrate, trichostatin A, hydroxyurea, sulforaphane or a sulforaphane analog, or a sulforaphane dithocarbamate metabolite. In an aspect, the compound comprises a combination of a histone deacetylase inhibitor, such as for example, a Class I histone deacetylase inhibitor or a Class II histone deacetylase inhibitor, and one or more of the following: 4-phenylbutyrate, trichostatin A, hydroxyurea, sulforaphane or a sulforaphane analog, or a sulforaphane dithocarbamate metabolite. In an aspect, the compound comprises a combination of 4-phenylbutyrate, trichostatin A, hydroxyurea, and sulforaphane or a sulforaphane analog.

In a disclosed method of determining the effectiveness of a test compound in treating autism or an autism related disorder, a comparative compound, to which the compound being tested is compared to for effectiveness or changes in the cells in the assay, is present as a structure represented by a formula:

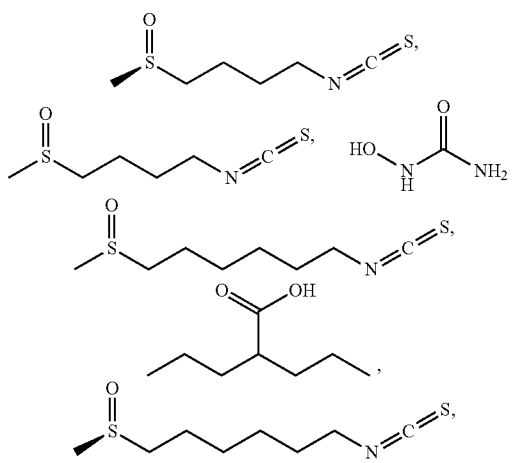

-continued

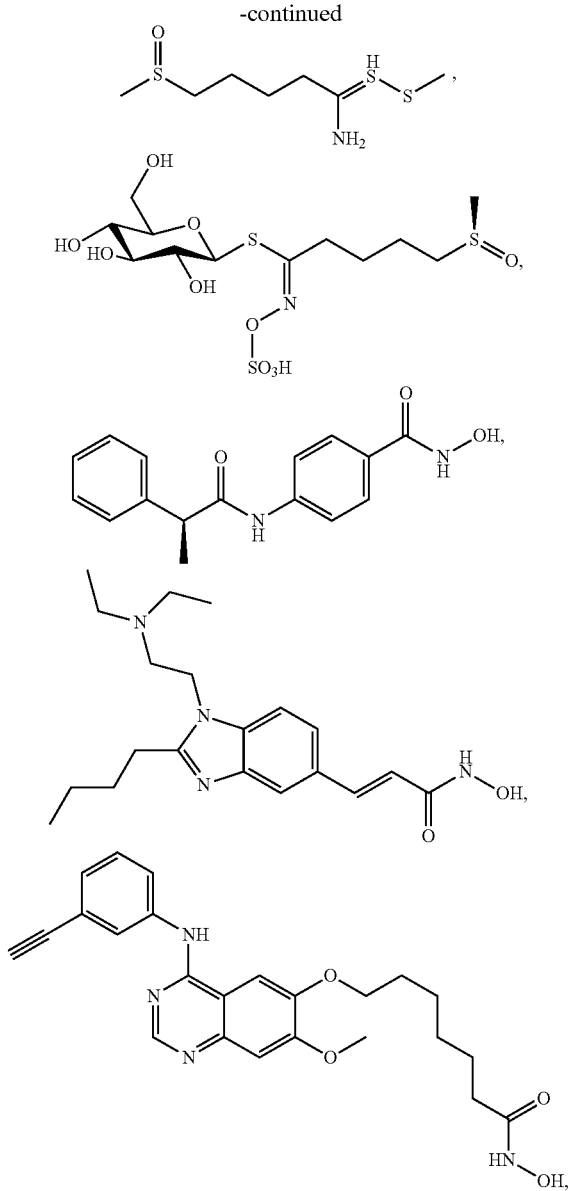

or a subgroup or pharmaceutically acceptable salt thereof.

Compounds may be tested in in vitro conditions or in in vivo conditions.

E. Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, a cruciferous sprout is a plant or seedling that is at an early stage of development following seed germination. Cruciferous seeds are placed in an environment in which they germinate and grow. The cruciferous sprouts may be harvested following seed germination through and including the 2-leaf stage.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A subject also can be a transgenic, non-human animal including but not limited to a transgenic mouse or transgenic rat.

A patient refers to a subject afflicted with a disease or disorder. The term "patient" includes human and veterinary subjects. In some aspects of the disclosed methods, the subject has been diagnosed with a need for treatment for autism or one or more autism spectrum disorders prior to the administering step.

As used herein, the term "analog" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, "homolog" or "homologue" refers to a polypeptide or nucleic acid with homology to a specific known sequence. Specifically disclosed are variants of the nucleic acids and polypeptides herein disclosed which have at least 40, 41, 42, 43, 44, 45, 46, 47, 48, 49, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated or known sequence. Those of skill in the art readily understand how to determine the homology of two proteins or nucleic acids. For example, the homology can be calculated after aligning the two sequences so that the homology is at its highest level. It is understood that one way to define any variants, modifications, or derivatives of the disclosed genes and proteins herein is through defining the variants, modification, and derivatives in terms of homology to specific known sequences.

As used herein, the term "treatment" refers to the medical management of a subject or a patient with the intent to cure, ameliorate, stabilize, or prevent a disease, pathological condition, or disorder, such as, for example, autism or one or more autism spectrum disorders. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In an aspect, the disease, pathological condition, or disorder is autism or one or more autism spectrum disorders.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, the amino acid abbreviations are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

"Peptide" as used herein refers to any peptide, oligopeptide, polypeptide, gene product, expression product, or protein. For example, a peptide can be an enzyme. A peptide is comprised of consecutive amino acids. Polypeptides encompass naturally occurring or synthetic molecule, and may contain modified amino acids other than the 20 gene-encoded amino acids. Polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide.

In general, the biological activity or biological action of a gene/nucleic acid or peptide refers to any function exhibited or performed by the gene/nucleic acid or peptide that is ascribed to the naturally occurring form of the gene/nucleic acid or peptide as measured or observed in vivo (i.e., in the natural physiological environment of the gene/nucleic acid or peptide) or in vitro (i.e., under laboratory conditions).

The term "enzyme" as used herein refers to any peptide that catalyzes a chemical reaction of other substances without itself being destroyed or altered upon completion of the reaction. Typically, a peptide having enzymatic activity catalyzes the formation of one or more products from one or more substrates. Such peptides can have any type of enzymatic activity including, without limitation, the enzymatic activity or enzymatic activities associated with enzymes such as those disclosed herein.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, "$EC_{50}$," is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in an in vitro or in vivo system as is convenient and appropriate for the biological response of interest. For example, the response can be measured in vitro using cultured brain cells or in an ex vivo organ culture system with isolated brain cells. Alternatively, the response can be measured in vivo using an appropriate research model such as rodent, including mice and rats. As appropriate, the response can be measured in a transgenic or knockout mouse or rat wherein a gene or genes has been introduced or knocked-out, as appropriate, to replicate a disease process.

As used herein, "$IC_{50}$," is intended to refer to the concentration or dose of a substance (e.g., a compound or a drug) that is required for 50% inhibition or diminution of a biological process, or component of a process, including a protein, subunit, organelle, ribonucleoprotein, etc. $IC_{50}$ also refers to the concentration or dose of a substance that is required for 50% inhibition or diminution in vivo, as further defined elsewhere herein. Alternatively, $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured brain cells or in an ex vivo organ culture system with isolated brain cells. Alternatively, the response can be measured in vivo using an appropriate research model such as rodent, including mice and rats. As appropriate, the response can be measured in a transgenic or knockout mouse or rat wherein a gene or genes has been introduced or knocked-out, as appropriate, to replicate a disease process.

Cells can be obtained from commercial sources such as the American Type Culture Collection (ATCC) and can be prokaryotic or eukaryotic. Cells can be grown in liquid media culture or on tissue culture plates. The growth conditions will be dependent upon the specific cells used and such conditions would be known to one of skill in the art. Transfection and growth of host cells is described in Maniatis et al.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

As used herein, the terms "optional" or "optionally" means that the subsequently described event or circumstance can or cannot occur, and that the description includes instances where said event or circumstance occurs and instances where it does not.

As used herein, the terms "transformation" and "transfection" mean the introduction of a nucleic acid, e.g., an expression vector, into a recipient cell including introduction of a nucleic acid to the chromosomal DNA of said cell. The art is familiar with various compositions, methods, techniques, etc. used to effect the introduction of a nucleic acid into a recipient cell. The art is familiar with such compositions, methods, techniques, etc. for both eukaryotic and prokaryotic cells. The art is familiar with such compositions, methods, techniques, etc. for the optimization of the introduction and expression of a nucleic acid into and within a recipient cell.

The term "contacting" as used herein refers to bringing a disclosed compound and a cell, target receptor, gene, peptide, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the term "determining" can refer to measuring or ascertaining a quantity or an amount or a change in expression and/or activity level, e.g., of a nucleotide or transcript or polypeptide. For example, determining the amount of a disclosed transcript or polypeptide in a sample as used herein can refer to the steps that the skilled person would take to measure or ascertain some quantifiable value of the transcript or polypeptide in the sample. The art is familiar with the ways to measure an amount of the disclosed nucleotides, transcripts, polypeptides, etc.

As used herein, the term "level" refers to the amount of a target molecule in a sample, e.g., a sample from a subject. The amount of the molecule can be determined by any method known in the art and will depend in part on the nature of the molecule (i.e., gene, mRNA, cDNA, protein, enzyme, etc.). The art is familiar with quantification methods for nucleotides (e.g., genes, cDNA, mRNA, etc.) as well as proteins, polypeptides, enzymes, etc. It is understood that the amount or level of a molecule in a sample need not be determined in absolute terms, but can be determined in relative terms (e.g., when compare to a control or a sham or an untreated sample).

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by the composition.

As used herein, the term "diagnosed" means having been subjected to a physical examination by a person of skill, for example, a physician, and found to have a condition that can be diagnosed or treated or ameliorated or detected or lessened by the compounds, compositions, or methods disclosed herein. For example, "diagnosed with autism" or "diagnosed with one or more autism spectrum disorders" means having been subjected to a physical examination by a person of skill, for example, a physician, and found to have a condition that can be diagnosed or treated by a compound or composition that alleviates or ameliorates autism or one or more autism spectrum disorders.

As used herein, the phrase "identified to be in need of treatment for a disorder," or the like, refers to selection of a subject based upon need for treatment of the disorder. For example, a subject can be identified as having a need for treatment of a disorder (e.g., autism or an autism spectrum) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a disclosed compositions or pharmaceutical preparation comprising a disclosed composition to a subject. Such methods are well known to those skilled in the art and include, but are not limited to, intracardiac administration, intramyocardial administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. Administration can be repeated, for example, once per day, or two or more times per day, or once per week, or two or more times per week, or every other week, or once per month, or one or more times per month, or every other day, or every other week, or every over month, or every other year, so forth and so on. In various aspects, a preparation can be administered therapeutically; that is, administered to treat an existing disease or condition. In further various aspects, a preparation can be administered prophylactically; that is, administered for prevention of a disease or condition.

Disclosed are the components to be used to prepare a composition of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

The present invention can be understood more readily by reference to the following detailed description of the invention and the Examples included therein.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

F. Experimental

As each of the small molecules can produce similar outcomes in diverse Mendelian and complex disorders, these small molecules likely induce common cellular effects. These molecules include two (2) histone deacetylase inhibitors, 4-phenylbutyrate and trichostatin A, and two (2) small molecules without direct histone deacetylase inhibitor activity, hydroxyurea and sulforaphane. In some cases, the therapeutic effects of histone deacetylase inhibitors (HDACi) are attributed to an increase in expression of genes related to the disease-causing gene. In the neurological disorder X-linked adrenoleukodystrophy (XALD), the potentially beneficial reduction of very long chain fatty acid levels by trichostatin A was not due to an increase in expression of a compensatory gene. Rather, the reduction in 4-phenylbutyrate was accompanied by an increase in proliferation of the key stress-sensing organelles, i.e., the mitochondria and peroxisomes. These studies examine whether 4-phenylbutyrate, trichostatin A, hydroxyurea, and sulforaphane share a common cellular response, which includes by induction of mitochondrial biogenesis, peroxisome proliferation, activation of the stress proteome, which are collectively referred to as adaptive cell survival response.

The studies described herein have identified the activation of the evolutionarily conserved stress proteome and mitochondrial biogenesis as the common cellular responses to small molecule therapy. This series of responses may be a common basis of therapeutic action in various diseases. Modulation of this novel therapeutic target could broaden the range of treatable diseases and be used to optimize therapeutic small molecules or agents without directly targeting the causative genetic abnormalities.

i) Materials and Methods a. Cell Culture

Primary human fibroblasts, HeLa cells (ATCC #CCL-2, a gift from Dr. Hal Dietz, Johns Hopkins University, Baltimore, Md.), and K562 cells (ATCC # CCL-243) were grown in minimal Eagle medium (MEM; Mediatech, Manassas, Va.), RPMI medium (Mediatech) supplemented with 10 mM HEPES and 1 mM sodium pyruvate, or RPMI, respectively, and supplemented with 10% fetal bovine serum, penicillin (100 U/mL), and streptomycin (100 U/ml). Fibroblasts (70-95% confluent) were treated with 5 mM 4PBA (1 mM for JNK inhibition studies), 600 µM HU, 200 nM TSA, or 5 µM SFN unless otherwise specified. K562 cells were treated with 1.2 mM SB or 100 µM HU. All drugs were obtained from Sigma-Aldrich (St. Louis, Mo.). The concentration of each drug per cell type was titrated to allow 100% viability and to minimally affect growth rate. The duration of treatment varied by experiment as indicated in the figure legends.

b. HDAC Activity Assay

A colorimetric HDAC activity assay was performed in triplicate using 100-200 µg of HeLa or fibroblast lysates following the manufacturer's protocol (K331; Biovision, Mountain View, Calif.).

c. Indirect Immunofluorescence

Performed as described in Watkins et al., 1995 using 4% formaldehyde, 1% Triton X-100, primary antibody anti-ATP5B (Millipore, Billerica, Mass.) or anti-ABCD3 (Invitrogen, Carlsbad, Calif.), and secondary antibody sheep anti-mouse IgG FITC-conjugated (Santa Cruz Biotechnology, Santa Cruz, Calif.) or goat anti-rabbit IgG rhodamine-conjugated (Jackson ImmunoResearch, West Grove, Pa.).

d. In-Cell Western Analysis

The immunostaining of primary human fibroblasts with anti-ATP5B, DRAQ5 (Cell Signaling Technologies, Danvers, Mass.; a cellular DNA stain to normalize cell number), and secondary antibody IRDye 800CW donkey anti-mouse IgG (Li-cor Biosciences, Lincoln, Nebr.) was identical to the indirect immunofluorescence procedure described above and performed in duplicate. Imaging and quantification were performed using the Odyssey Imager (L1-cor Biosciences).

e. Inhibition Studies

Antimycin A (10 ng/mL), LY294002, PD98059, RO-31-8425, SB203580, SP600125, and L-NAME were obtained from Sigma. Compound C was from EMD Biosciences (Darmstadt, Germany). Human fibroblasts were treated with each inhibitor. Then, 45-75 min later, either 4PBA, HU, TSA, or SFN was added. Cells were stained four to six days after treatment with one of the small molecules. As a control for inhibitors dissolved in DMSO, fibroblasts were treated with an equivalent amount of DMSO in the absence of inhibitor.

f. Real-Time PCR Analysis (RT-PCR)

Following the manufacturer's protocols, DNase I-treated cDNA was synthesized using Superscript III or Thermoscript reverse transcriptase (Invitrogen). PCR reactions were performed in duplicate on the Roche Lightcycler 3.5 (Basel, Switzerland) or the Bio-Rad iCycler (Hercules, Calif.) using Quantitech SYBR green PCR mix (Qiagen, Valencia, Calif.). GeNorm software calculated a normalization factor for each sample using the relative amounts of at least two of the following reference genes, β2-microglobulin, glyceraldehyde-6-phosphate, actin, and/or eukaryotic elongation factor 1A (Vandesompele et al., 2002). Primers for the various experiments described herein are listed below.

| SEQ ID NO: | Primer Name | Primer Sequence (5' to 3') |
|---|---|---|
| 1 | MAP3K4F | CCCAGAAACTTGGACTGGAA |
| 2 | MAP3K4R | CCCAGCGCTAAGAGTAAACG |
| 3 | cJun-ex1F | CAGGTGGCACAGCTTAAACA |
| 4 | cJun-ex1R | TGAGTTGGCACCCACTGTTA |
| 5 | PGC1αF | AGCTGCTGAAGAGGCAAGAG |
| 6 | PGC1αR | CTCCAGGAAAAGCAAAGCTG |
| 7 | PGC1β-ex12F | TGAAGCCATGGATTTTGACA |
| 8 | PGC1β-ex12R | TATTGGAAGGGCCTTGTCTG |
| 9 | NRF1-ex11F | TATCAGACAGCGCAGTCACC |
| 10 | NRF1-ex11R | CAATGTCACCACCTCCACAG |
| 11 | NRF2-ex15F | GGCAGCTGGTTTTATTGGAA |
| 12 | NRF2-ex15R | ACAGTTTCACGTCCCCACTC |
| 13 | TFAM-ex7 | GCACAGGAAACCAGTTAGG |
| 14 | TFAM-ex7R | ATCTGGGTTTTCCAAAGCAA |
| 15 | ATF4-ex2F | AGATGACCTGGAAACCATGC |
| 16 | ATF4-ex2R | GTGTCATCCAACGTGGTCAG |
| 17 | XBP1-ex6F | ACTGCCTGGAGGATAGCAGA |
| 18 | XBP1-ex6R | ACCTTGGACTGCTGGATGTC |
| 19 | BiP-ex8F | AATGACCAGAATCGCCTGAC |
| 20 | BiP-ex8R | CGCTCCTTGAGCTTTTGTC |
| 21 | HSF1F | CCGCTCCACAGAGATACACA |
| 22 | HSF1R | GTCTTGTCCGTCCATCCACT |
| 23 | ATF6F | GCAGAACCTCAGCCACTTTC |
| 24 | ATF6R | ACCGAGGAGACGAGACTGAA |
| 25 | HSP90AA1F | GGCAGAGGCTGATAAGAACG |
| 26 | HSP90AA1R | AGACAGGAGCGCAGTTTCAT |
| 27 | HSPA1AF | CCGAGAAGGACGAGTTTGAG |
| 28 | HSPA1AR | CTGGTACAGTCCGCTGATGA |
| 29 | DNAJC3F | GATATTTTGCCCAGCAGGAA |
| 30 | DNAJC3R | TTTGTCTCCCGTTTTGGAAC |
| 31 | NFE2L2F-intron | ACACGGTCCACAGCTCATC |
| 32 | NFE2L2R-intron | TCTTGCCTCCAAAGTATGTCAA |
| 33 | HMOX1-ex5F | TCCGATGGGTCCTTACACTC |
| 34 | HMOX1-ex5R | TAAGGAAGCCAGCCAAGAGA |
| 35 | SOD2-ex2F | CCCTGGAACCTCACATCAAC |
| 36 | SOD2-ex3R | CGTTAGGGCTGAGGTTTGTC |
| 37 | B-actinF | ACGTTGCTATCCAGGCTGTGCTAT |
| 38 | B-actinR | CGGTGAGGATCTTCATGAGGTAGT |

-continued

| | | |
|---|---|---|
| 39 | EEF1AF | TTGCCGCCAGAACACAG |
| 40 | EEF1AR | ACTTGCCCGAATCTACGTGT |
| 41 | B2MF | TGCTGTCTCCATGTTTGATGTATCT |
| 42 | B2MR | TCTCTGCTCCCCACCTCTAAGT |
| 43 | CHOP*F | GGAGCTGGAAGCCTGGTATG |
| 44 | CHOP*R | GCTCTGGGAGGTGCTTGT |
| 45 | Beclin1F (BCN1) | CAAGATCCTGGACCGTGTCA |
| 46 | Beclin1R (BCN1) | TGGCCATTTCTGTGGACATCA |
| 47 | APSLF-intron | TGCAGAAGAAAATGGATTTCG |
| 48 | APGSLR-intron | ACTGTCCATCTGCAGCCAC |
| 49 | FL-SMNF | GCGATGATTCTGACATTTGG |
| 50 | FL-SMNR | AATGAAGCCACAGCTTTATCA |
| 51 | Total SMNF | ATAATTCCCCCACCACCTC |
| 52 | Total SMNR | CACCTTCCTTCTTTTTGATTTTGTC | g. Western Blot Analysis

Cell lysates were collected in mammalian protein extraction reagent (m-PER; Thermo Scientific, Rockford, Ill.) plus 1×protease inhibitor (Sigma-Aldrich) and 1×Halt phosphatase inhibitor (Thermo Scientific). Denatured SDS-PAGE and immunoblot analyses were performed using the following antibodies: phosphorylated JNK and β-actin from Santa Cruz Biotechnology, HSP70, HSP90, BIP, phosphorylated eIF2α, and XBP1 from Cell Signaling, APG8 (Abgent, San Diego, Calif.), and SOD2 (Stressgen, Ann Arbor, Mich.). Quantitation was performed using a Fuji Intelligent Dark box II, FUJI LAS-1000 Lite software and Image Gauge v4.22 software (Tokyo, Japan).

h. Fatty Acid β-Oxidation

Fatty acid β-oxidation activity in XALD fibroblasts was determined by measuring their capacity to degrade 1-$^{14}$C-labeled fatty acids to water-soluble products as described in McGuiness et al., 2003.

i. Flow Cytometry

K562 cells were incubated with 50 nM Mitotracker Green FM, 300 nM Mitotracker Deep Red 633 (Invitrogen), or PBS as a negative control for 15 min at 37° C. or stained with anti-Pex14 using Caltag Fix and Perm reagents (Invitrogen) following the manufacturer's instructions. Stained cells were suspended in 0.5 mL of 1% paraformaldehyde/PBS and subjected to flow cytometric analysis (FACScan machine, Becton Dickinson, Franklin Lakes, N.J.).

j. Measurement of Hemoglobin

K562 cells were suspended in 1.1 mL media and 240 µL of DAF [working solution 50 µL 2,7diaminofluorene (DAF) stock (50 µg DAF in 5 mL 90% glacial acetic acid), 50 µL 30% hydrogen peroxide, and 2.5 ml 200 mM Tris-HCl, pH 7.0]. DAF stained hemoglobinized cells were scored using a hemocytometer.

k. Mitotracker Staining

SMA type I (GM00232) fibroblasts were treated with 2.5 mM 4PBA, 300 mM HU, 100 nM TSA or 2.5 mM SFN for 5 days, live stained with 25 nM Mitotracker Red CMXROS (Invitrogen) in pre-warmed MEM media for 15 min at 37° C. in a $CO_2$ incubator. Stained cells were washed with pre-warmed MEM, washed with PBS and excess PBS was removed. The cells were examined under the microscope at ×80.

l. SIRT1 Activity Assay

A fluorescence-based SIRT1 activity assay was performed in triplicate following the manufacturer's protocol (10010401; Cayman Chemical Company, Ann Arbor, Mich., USA). The percent developer interference was below 3% for each small molecule. The percent fluorophore interference was below 9% for each small molecule. The acceptable interference values were ≤10%.

m. Statistical Analyses

Three or more independent experiments were performed for each technique unless otherwise noted and the standard error of the mean (SEM) calculated and graphed. A one-tailed Student's t-test was used to calculate p-values. P-values ≤0.05 were considered significant.

ii) Activation of Stress Proteosome

Many small molecules are under investigation as potential therapeutic agents for a spectrum of Mendelian and complex genetic disorders. Screens for small molecules typically target a specific cellular pathway related to, or implicated in, a particular disorder. However, various small molecules with different known mechanisms of action, including histone deacetylase inhibitors (HDACi) and those that do not inhibit histone deacetylases, produce similar favorable outcomes in a wide variety of heterogeneous disease models in which different classes of proteins, different cell types, and different molecular pathways are affected. (Table 1).

TABLE 1

Similar Therapeutic Responses of Diverse Small Molecules in Various Disease models.

| Disease Model Studied | Small Molecule | Therapeutic Effect | References |
|---|---|---|---|
| Huntington's disease | 4PBA, TSA | reduce neurodegeneration increase survival | Gardian et al., 2005 Oliveira et al., 2006 |
| Alzheimer's disease | 4PBA, SFN | reduce β-amyloid toxicity prevent neuronal cell death | Park et al., 2009 Ricobaraza et al., 2009 |
| Diabetes | 4PBA, TSA, SFN | hyperglycemia normalization improve glucose utilization | Ozcan et al., 2006 Xue et al., 2008 Sun et al., 2008 |
| Sickle Cell Disease | 4PBA, HU, TSA | increase F-cell production | Hsiao et al., 2006 |
| X-linked Adrenoleukodystrophy | 4PBA, TSA | decrease very long chain fatty acid levels | McGuiness et al., 2003 |
| Spinal Muscular Atrophy | 4PBA, HU, TSA | increase percentage of full length SMN2 transcript | Lunn et al., 2008 |

TABLE 1-continued

Similar Therapeutic Responses of Diverse Small Molecules in Various Disease models.

| Disease Model Studied | Small Molecule | Therapeutic Effect | References |
|---|---|---|---|
| Fragile X Mental Retardation | 4PBA, HU, TSA | increase transcription of FMR1 | Gorski et al., 1985 Chiurazzi et al., 1999 |
| Ischemia | 4PBA, SFN | protection via antioxidant pathway | Qi et al., 2004 Yoon et al., 2008 |
| Cystic Fibrosis | 4PBA, TSA | increase proper protein trafficking | Choo-Kang et al., 2001 Hutt et al., 2010 |

4PBA = 4-phenylbutyrate
HU = hydroxyurea
SFN = sulforaphane
TSA = trichostatin A The class I and class II HDACi, 4-phenylbutyrate (4PBA) and trichostatin A (TSA), have been extensively studied. In some cases, the beneficial effect of HDACi treatment was attributed to an increase in the expression of genes related to, or compensating for, the primary disease-causing gene (Kemp et al., 1998; Gardian et al., 2005).

Studies of X-linked adrenoleukodystrophy (XALD), a neurological disorder, indicate that the observed therapeutic overlap of HDACi and other small molecules is due to modulation of general cellular functions rather than direct targeting of compensatory targets. Both 4PBA and TSA treatment normalized the abnormally high levels of very long chain fatty acids (VLCFA) in human XALD fibroblasts and the ALD (Abcd1−/Y) mouse model in vivo (McGuinness et al., 2003). 4PBA, but not TSA, increased expression of ABCD2, whose function overlaps that of the defective peroxisomal gene ABCD1 (Li et al., 2002). Thus, induction of ABCD2 does not directly correlate to the reduction of VLCFA levels in all instances. However, 4PBA treatment of XALD fibroblasts also increased mitochondrial and peroxisomal biogenesis, which are organelles required for cellular detoxification and stress-sensing (Kemp et al., 1998; McGuinness et al., 2003). The induction of peroxisome proliferation by 4PBA treatment is dependent on peroxisome biogenesis factor 11 alpha (PEX11α) (Li et al., 2002). PEX11β is required for constitutive peroxisome abundance, whereas PEX11α is not. Rather, PEX11α induces peroxisome proliferation in response to external stimuli or stress (Schrader et al., 1998). Therefore, the induction of the generalized cellular stress response, also known as the adaptive cell survival response, by small molecules was monitored (Kultz 2003). The therapeutic relevance of modulating a general cellular response can explain how small molecules are able to elicit the observed diverse effects in a broad spectrum of diseases (e.g., Table 1, in which the amenable diseases exhibit minor defects at the cellular level regardless of the severity of the clinical phenotypes).

The cellular stress response, which has been conserved from archaea to eukaryotes, protects against damage and promotes viability by adapting cells to their environment (Kultz 2003). This response modulates the activity of molecular chaperones and proteins (i) that affect reduction-oxidation regulation, (ii) that sense and repair DNA damage, (iii) that are involved in protein degradation, and (iv) that are involved in fatty acid, lipid, and energy metabolism. Stimulation of these adaptive survival pathways readjusts the cell to various stressors and restores cellular homeostasis by inducing the heat shock response (HSR), the unfolded protein response (UPR), the autophagic response, the antioxidant response, and mitochondrial and peroxisomal biogenesis. Activation of the UPR and autophagy, proteostatic components of the stress response, and modulation of mitochondrial energetics can alleviate symptoms of neurodegenerative and aging disorders and extend the lifespan of model organisms (Ong et al., 2010; Powers et al., 2009; Durieux et al., 2011). The present experiments indicate that joint activation of the stress proteome and the subsequent reestablishment of homeostasis is beneficial to a broad range of diseases (Table 1).

The potential of four small molecules with overlapping therapeutic benefits but different known functions (see Table 1), to induce the adaptive cell survival response was evaluated. The primary known modes of action of these small molecules: 4PBA, TSA, hydroxyurea (HU), and sulforaphane (SFN) are listed in Table 2. These studies show that, at concentrations minimally affecting cellular proliferation, these four drugs increase mitochondrial biogenesis and peroxisome proliferation in both normal and XALD human fibroblasts as well as in human K562 erythroleukemic cells. These four pharmacological small molecules induced primary pathways that constitute the cytoprotective stress proteome. Thus, the therapeutic effects of these pharmacological small molecules or agents result from stimulation of the adaptive cell survival response and the reestablishment of cellular homeostasis. Identification of these common cellular responses allows screening for more clinically efficacious molecules, expands the repertoire of currently treatable diseases to include those with unknown genetic etiology, and shortens the time to treatment for some diseases.

TABLE 2

Small Molecules and Mode of Action

| Small Molecule | Known Mode of Action | Used Clinically |
|---|---|---|
| 4-phenylbutyrate | histone deacetylase inhibitor | Yes, Orally |
| trichostatin A | histone deacetylase inhibitor | No |
| hydroxyurea | ribonucleotide reductase inhibitor | Yes, Orally |
| sulforaphane | phase II detoxification enzyme inducer | Yes, Clinical Trials (Oral) | a. Small Molecule Induction of Mitochondrial Biogenesis and Peroxisome Proliferation 4PBA treatment of fibroblasts from healthy individuals, XALD patients, and patients with peroxisomal biogenesis disorders increased mitochondrial mass and peroxisome proliferation 2- to 3-fold (Kemp et al., 1998; McGuinness et al., 2003; Wei et al., 2000). Other small molecules, including HU, TSA, and SFN, exhibit therapeutic overlap with 4PBA (Table 1). To broaden the examination of small molecule induction of mitochondrial biogenesis and peroxisome proliferation, normal human fibroblasts were treated for four to five days with 4PBA, HU, TSA, or SFN. Drug concentrations were titrated to allow 100% viability and minimally affect cellular proliferation. Both mitochondrial biogenesis and peroxisomal biogenesis were monitored. Immunofluorescence staining for the mitochondrial membrane protein ATP synthase beta subunit (ATP5B) and the 70 kD peroxisomal membrane protein (ABCD3) revealed drug-induced increases in mitochondrial biogenesis and peroxisomal proliferation, respectively, by all four small molecules or agents (FIG. 1A). FIG. 1A shows immunofluorescence staining for mitochondrial membrane protein ATP5B (top) and the peroxisomal membrane protein ABCD3 (bottom). Normal human fibroblasts were treated with each drug for four to five days. (400× magnification). This identified mitochondrial biogenesis and peroxisome proliferation as a common cellular response to treatment with these small molecules.

b. Beneficial Effects of 4PBA in XALD Cells Require Increased Mitochondrial Function 4PBA-induced peroxisomal VLCFA β-oxidation (degradation) is dependent on mitochondrial long chain fatty acid (LCFA) β-oxidation (McGuinness et al., 2003). To determine whether 4PBA-induced peroxisomal VLCFA β-oxidation was dependent on mitochondrial function, mitochondrial function was chemically inhibited with antimycin A (AA). Antimycin A (AA) is a cytochrome c reductase inhibitor that inhibits the mitochondrial electron transport chain, mitochondrial biogenesis, and thus, cellular respiration (Ranganathan et al., 2009). The concentration of AA, which was titrated to minimally affect basal levels of LCFA and VLCFA β-oxidation, did not exhibit any observable cellular toxicity, and did not affect cellular proliferation. Treatment of XALD fibroblasts with 4PBA (1) induced LCFA and VLCFA β-oxidation (FIG. 1B) and (2) increased carbon dioxide release (Heinzer et al., 2003). FIG. 1B shows the VLCFA analysis. XALD fibroblasts were treated with 4PBA in the presence or absence of antimycin A (AA), a cytochrome c reductase inhibitor, for five days and β-oxidation levels of LCFA (C16:0) and VLCFA (C24:0) levels were measured. However, in the presence of AA, the 4PBA-induction of mitochondrial LCFA β-oxidation was inhibited. This inhibition concomitantly blocked the induction of peroxisomal VLCFA β-oxidation. Thus, pharmacological reduction in peroxisomal VLCFA levels by 4PBA treatment was not only dependent on mitochondrial LCFA β-oxidation, but was more generally dependent on increased mitochondrial energy production.

c. Beneficial Effects of Sodium Butyrate and Hydroxyurea in a B-Hemoglobinopathy Model Require Induced Mitochondrial Biogenesis The clinical severity of 3-hemoglobinopathies, such as sickle cell disease (SCD) and β-thalasemmia, was ameliorated by increasing the number of HbF-containing cells (F-cells). The increase in the number of HbF-containing cells elevated the total HbF levels (Perrine 2008). Sodium butyrate (SB, an analog of 4PBA) and HU increased HbF levels in several contexts: in SCD and β-thalasemmia patients, in K562 cells, and in CD34+ derived hematopoietic stem cells (Keefer et al., 2006). To further assess the pharmacological commonality of the induction of mitochondrial and peroxisomal biogenesis in a disease model unrelated to the neurological disease XALD, these responses were examined in K562 cells. K562 cells are an erythroleukemic cell line that produces HbF and is commonly used as a model of the induction of F-cell production.

K562 cells were treated with SB and HU for four to ten days. Flow cytometric analyses demonstrated that both SB and HU significantly increased mitochondrial mass, the number of HbF-producing cells, and peroxisomal proliferation (FIGS. 1C, 1D, and 1E). FIGS. 1C, 1D, and 1E shows results from the treatment of K562 cells with SB, HU, or PBS as a control (CON). (n≥3 unless otherwise noted).

To determine whether the induction of mitochondrial biogenesis by SB or HU treatment was necessary for the induction of HbF-producing cell production, K562 cells were treated with SB or HU in the presence or absence of AA. The concentration of AA, which was again titrated to minimally affect basal levels of HbF-producing cells, did not exhibit any observable cellular toxicity and did not affect cellular proliferation. The induction of mitochondrial biogenesis and the induction of HbF-producing cells by SB or HU treatment were significantly inhibited by AA (FIG. 1C-1D). FIG. 1C shows flow cytometric analysis of mitochondrial mass. After two to four days of drug treatment with or without AA, mitochondrial mass was measured using Mitotracker, a mitochondrial stain. Fold change (drug treated/control) is shown. FIG. 1D shows the analysis of HbF-producing cell production. After four days of drug treatment with or without AA, cells were stained with DAF. The relative number of cells producing HbF (DAF stained cells) were plotted. FIG. 1E shows flow cytometric analysis of peroxisome proliferation. After eight to ten days of drug treatment, peroxisome proliferation was measured using an antibody against the peroxisomal membrane protein, PEX14 and a FITC-labeled secondary antibody. Fold change (drug treated/control) is shown. In FIGS. 1C, 1D, and 1E, the * represents a statistically significant increase in a measurement between drug treated and control samples or a statistically significant decrease in a measurement between drug treated and drug treated samples in the presence of AA (p≤0.05) (Bars=SEM). This finding indicates dependence of the beneficial effect (i.e., elevated HbF levels) on induced mitochondrial biogenesis. Thus, the therapeutic effects observed in SCD may involve the pharmacological induction of mitochondrial biogenesis by SB or HU.

d. Pharmacological Induction of Mitochondrial Biogenesis is Dependent on the JNK Pathway Mitochondrial biogenesis is stimulated by various signaling pathways that activate the transcription factors peroxisome proliferator-activated receptor gamma coactivator-1 alpha and beta (PGC1 and PGC1β, respectively) (Lee et al., 2005). To determine whether the induction of mitochondrial biogenesis by these small molecules required the activation of a common kinase cascade or endothelial nitric oxide synthase (eNOS), XALD fibroblasts were treated with (i) each inducing drug and (ii) either an eNOS inhibitor or various specific kinase inhibitors (Table 3).

TABLE 3

Kinase and endothelial nitric oxide synthase inhibitors tested.

| Target | Chemical Inhibitor | Tested Concentrations | Inhibits Mitochondrial Biogenesis? |
|---|---|---|---|
| MAPKK1 | PD98059 | 10-100 µM | no |
| MAPKK1 | arctigenin | 1-50 µM | no |
| p38 MAPK | SB203580 | 10-100 µM | no |
| AMPK | compound C | 1-10 µM | no |
| constitutive eNOS | L-NAME | 0.1-1 mM | no |
| JNK 1, 2, and 3 | SP600125 | 5-50 µM | yes |
| MAPKK1 and 2 | U0126 | 10-50 µM | no |
| protein kinase C | RO-21-8425 | 1-30 µM | no |
| PI3K | LY294002 | 10-50 µM | no |

Mitogen activated protein kinase kinase 1 (MAPKK1) is an upstream activator of extracellular signal-regulated kinases 1 and 2 (ERK1/2).
Adenosine monophosphate protein kinase (AMPK).
Endothelial nitric oxide (eNOS).
c-jun N-terminal MAPK (JNK).
Phosphatidylinositide-3- kinase (PI3K).

Figure 2:
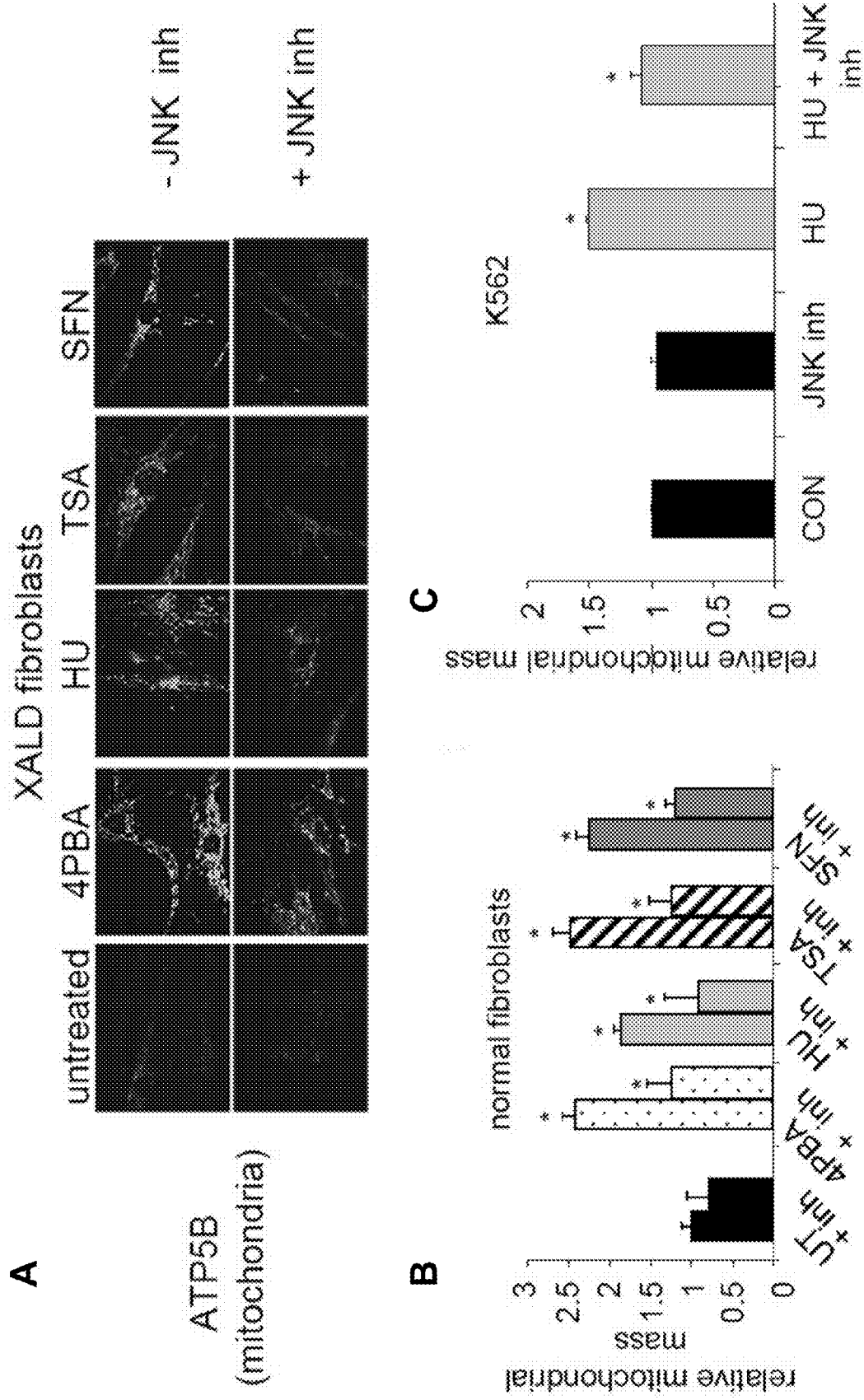
Figure 2:
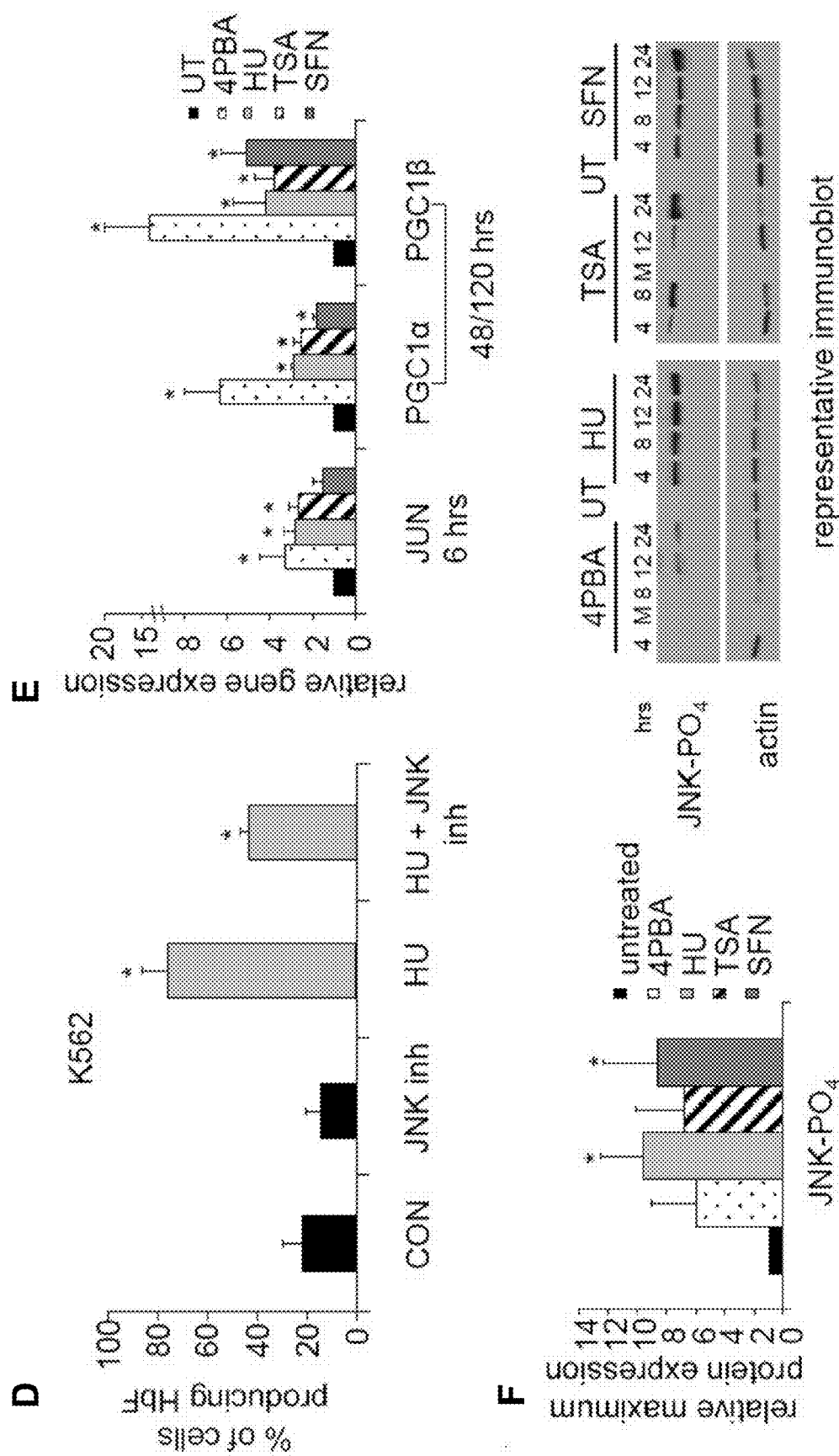

4PBA, HU, TSA, and SFN increased mitochondrial biogenesis in XALD fibroblasts (FIG. 2A. top row) Inhibition of pathways, including the p38 mitogen activated kinase (MAPK), the extracellular regulated kinase, the MAPK kinases 1 and 2, the adenosine monophosphate kinase, the protein kinase C, the phosphoinositide-3-kinase, and eNOS pathways, had no effect on drug-induced mitochondrial biogenesis. Only SP600125-inhibition (Bennett et al., 2001) of the stress activated protein kinase (SAPK) pathway, otherwise known as the c-jun N-terminal kinase (JNK) pathway, with reduced pharmacological induction of mitochondrial biogenesis as demonstrated by immunofluorescence staining in treated XALD and by quantitative in-cell western analyses normal human fibroblasts. (FIG. 2A-B). In FIGS. 2A-B, the JNK inhibitor SP600125 (10 µM+inh) was utilized. FIG. 2A shows immunofluorescence staining for mitochondrial membrane protein ATP5B. XALD fibroblasts were treated with each drug for four days with or without SP600125. (400× magnification). FIG. 2B shows quantification of pharmacological induction of mitochondrial biogenesis. Normal human fibroblasts were treated with each of the small four molecules with or without SP600125 for six days. Quantitative in-cell western analyses were performed using anti-ATP5B.

As indicated by an increase in ATP5B staining, 4PBA, HU, TSA, or SFN treatment alone significantly increased mitochondrial mass. In normal human fibroblasts, mitochondrial mass significantly increased 2.4-fold with 4PBA treatment, 1.8-fold with HU treatment, 2.5-fold with TSA treatment, and 2.2-fold with SFN treatment when compared to untreated cells. The mitochondrial mass of cells treated with each drug and the JNK inhibitor did not significantly differ from the mitochondrial mass of untreated cells.

In K562 cells, the JNK inhibitor SP600125 (Bennett et al., 2001) also blocked HU-induced mitochondrial biogenesis and consequently HbF-producing cell production (FIG. 2C-D). FIGS. 2C-D shows inhibition of mitochondrial biogenesis and HbF-containing cell production. K562 cells were treated for four days with HU in the presence or absence of SP600125 or PBS as a control (CON). FIG. 2C shows mitochondrial mass (plotted as in FIG. 1C) and FIG. 2D shows the relative number of HbF-producing cells were determined by staining with Mitotracker and DAF, respectively (n=2). In fully competent hematopoietic stem cells HU-stimulated F-cell production was similarly dependent on the JNK pathway. The JNK pathway is activated by external stressors and stimuli such as heat shock, osmotic shock, and ultraviolet irradiation (Yang et al., 2003). Therefore, these data indicate that the same cytoprotective pathway is involved in the pharmacological induction of mitochondrial biogenesis by 4PBA, HU, TSA, and SFN treatment.

Activation of the JNK pathway led to activation of the transcription factor JUN via phosphorylation. PGC1α and PGC1β maintained basal levels of mitochondria. PGC1α also induced mitochondrial biogenesis under physiological stress such as during adaptive thermogenesis, endurance exercise, or fasting (Kultz 2005). JUN transcript levels were significantly increased after six hours of treatment with 4PBA, HU, or TSA. PGC1α and PGC1β transcript levels were significantly increased after 48 hours or more of treatment with each of the four small molecules (FIG. 2E). JUN transcript levels were not consistently changed after SFN treatment. FIG. 2E shows mRNA expression of JUN and mitochondrial transcription factors PGC1α and PGC1β by RT-PCR. The relative gene expression for each treatment compared to untreated normal human fibroblasts was calculated and the fold change (drug treated/untreated) is shown. Measurements of PGC1α and PGC1β levels after SFN treatment were performed twice in duplicate.

However, JNK phosphorylation was increased within 24 hours of treatment with each drug, including SFN (FIG. 2F). Thus, the JNK pathway was activated and the abundance of the mitochondrial transcription factors was increased following 4PBA, HU, TSA, or SFN treatment. FIG. 2F shows immunoblot analysis of JNK phosphorylation (46 kDa). Normal human fibroblasts were treated at various time points. Treatment was initiated at the indicated times prior to collection. The average of the maximum protein expression (within 24 hours) for three or more independent experiments is shown as fold change (drug treated/untreated). Actin (43 kDa) was the loading control. M denotes the marker lane. (0.05≤p≤0.10 for 4PBA and TSA treated samples). The * statistically significant increase in a measurement between drug treated and untreated or control samples or a statistically significant decrease in a measurement between drug treated and drug treated samples in the presence of SP600125 (p≤0.05) (n≥3 independent experiments unless otherwise noted) (Bars=SEM).

e. Small Molecule Activation of the Adaptive Cell Survival Response

In three different cell types (normal human fibroblasts, XALD fibroblasts, and K562 cells) inhibition of the stress-activated JNK pathway blocked the small molecule induction of mitochondrial biogenesis. Mitochondrial biogenesis is a necessary response for the reduction of VLCFA in XALD cells and for the increase in HbF levels in K562 cells. The mitochondria are involved in cellular adaptation to stress, indicating that a common cellular response to these pharmacological small molecules or agents may be stimulation of the stress proteome. Expression of key components of the HSR, UPR, the autophagic response, and the antioxidant response were monitored at the transcriptional, translational, and/or post-translational level. These responses are known to be transiently activated in response to various cellular stressors. The degree of induction of each component can vary depending on the metabolic state of the cell (e.g., confluency, cell passage number) (Kultz 2003; Lallemand et al., 1998; Westerheide et al., 2009). Due to the transient nature of these responses, several components of each pathway were monitored at various time points within a 24 hour treatment. At least two normal human fibroblast lines were tested in three or more independent experiments. An increase in mRNA expression after 2 hr., 6 hr., or 18 hrs. of treatment occurred. The average of the maximal increase in protein expression within a 24 hour time frame was also compared to the untreated sample. Activation of each pathway was assessed by an increase in one or more components of each pathway.

f. Small Molecule Activation of the Heat Shock Response

Figure 3:
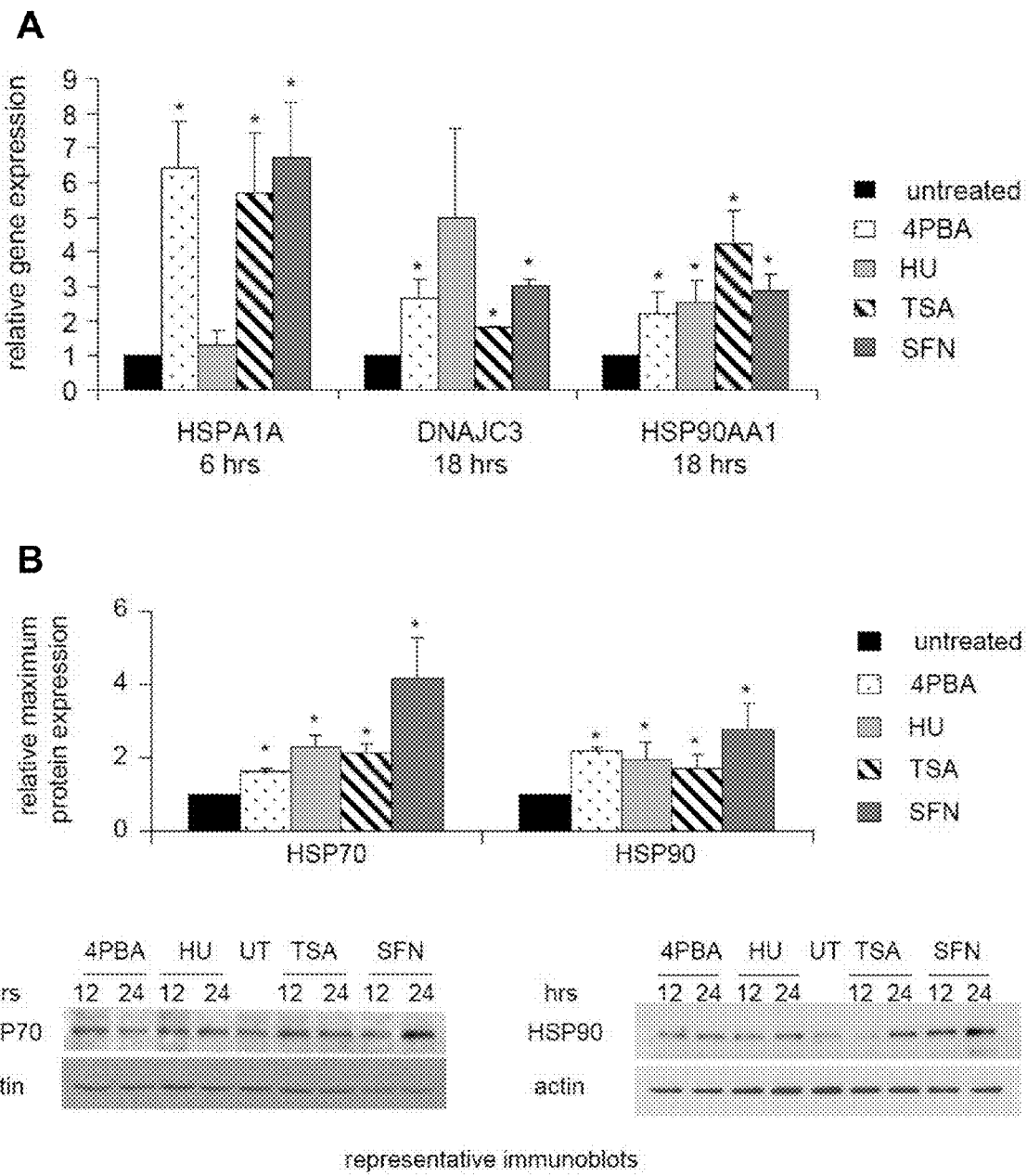
FIG. 3 (A-B) shows that the heat shock response is induced by 4PBA, HU, TSA, or SFN treatment.

Induction of the HSR is a hallmark of the adaptive cell survival response (Fedoroff 2006). To evaluate its activation, the expression of heat shock protein (HSP) 40, HSP 70, and HSP 90 family members was monitored. 4PBA, TSA, or SFN increased transcription of the HSP 70 kDa protein 1A (HSPA1A). All four small molecules or agents increased transcription of DNAJ HSP40 homolog subfamily C member 3 (DNAJC3) and transcription of HSP 90 kDa class A member 1 (HSP90AA1; FIG. 3A). FIG. 3A shows RT-PCR analyses of mRNA expression of HSR genes. Normal human fibroblasts were treated and the mRNA expression of HSPA1A (HSP70), DNAJC3 (HSP40), and HSP90AA1 (HSP90) was measured and plotted as in FIG. 2E. P-value for SFN DNAJC3 measurement is 0.10. HSPA1A transcript expression was not stimulated by HU treatment at the time points examined.

However, total HSP70 and HSP90 protein levels were significantly increased with all four small molecules or agents (FIG. 3B). The pharmacological induction of HSR mRNA and protein expression was similar to that caused by mild heat shock (Clark et al., 2009). Thus, the HSR was activated by 4PBA, HU, TSA, or SFN treatment. FIG. 3B shows immunoblot analyses of HSP expression. Normal human fibroblasts were treated at various time points within 24 hours and the average of the maximum protein expression of HSP70 (70 kDa) and HSP90 (90 kDa) is plotted as in FIG. 2F. Actin (43 kDa) was used as a loading control. (UT=untreated cells; * statistical significance ($p \leq 0.05$); Bars=SEM for $n \geq 3$ independent experiments).

g. Small Molecule Activation of the Unfolded Protein Response

UPR markers evaluated included the central UPR regulator glucose regulated protein 78 (BIP) and other components that are stimulated after the activation of the three ER transmembrane receptors: PKR-like ER kinase (PERK), inositol requiring 1 (IRE1), and activating transcription factor 6 (Fedoroff 2006). Elongation initiation factor 2 alpha (eIF2a) is phosphorylated by PERK, attenuates general translation, and induces activating transcription factor 4 (ATF4). CHOP promotes reactivation of PERK. XBP1 mRNA is non-conventionally spliced by the endonuclease activity of IRE1 upon UPR activation. BIP expression was significantly increased at the transcriptional and translational levels after treatment with 4PBA, HU, TSA, or SFN (FIG. 4A-4B). Treatment with these small molecules also increased ATF4 and CHOP mRNA expression (FIG. 4A), modestly increased eIF2α phosphorylation (FIG. 4B), and increased the total amount of XBP1 protein and the amount of spliced XBP1 protein (FIG. 4C).

Figure 4:
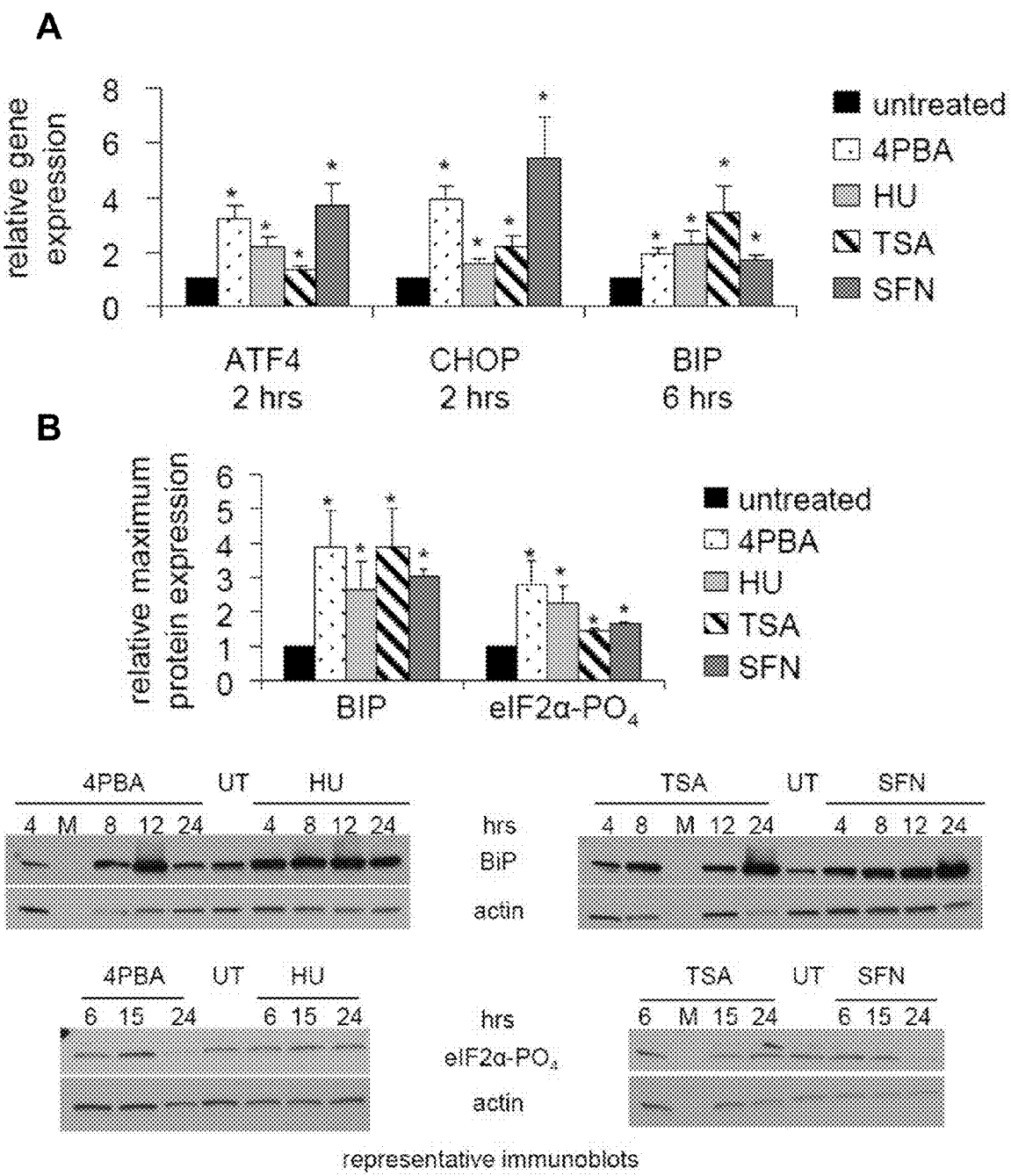
FIG. 4 (A-C) shows that the unfolded protein response is activated by treatment with 4PBA, HU, TSA, or SFN.
Figure 4:
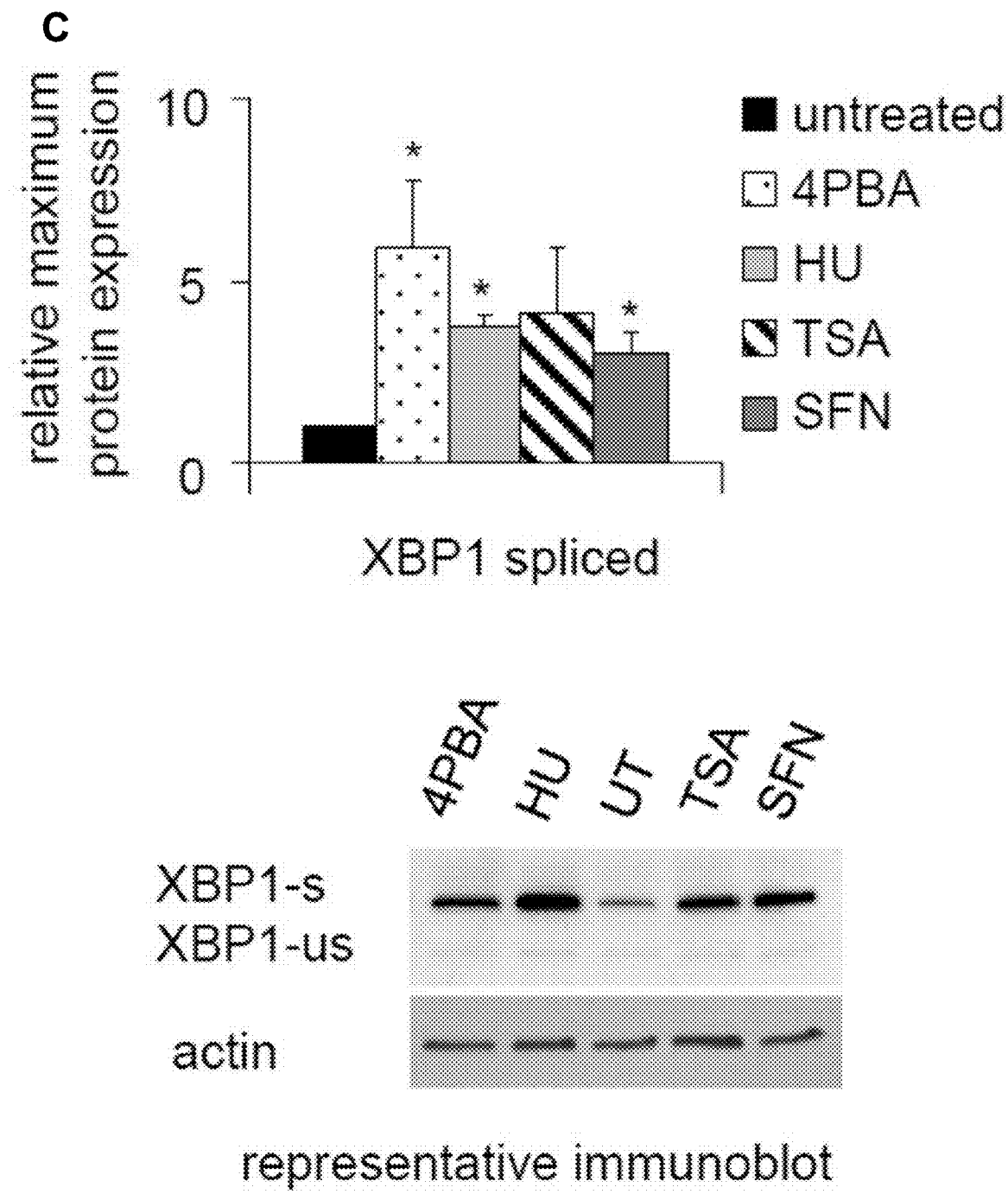

FIG. 4A shows RT-PCR analyses of mRNA expression of UPR genes. Normal human fibroblasts were treated with drugs as indicated. The expression of the UPR genes ATF4, CHOP, and BIP was measured as described in FIG. 2E. FIG. 4B shows immunoblot analyses of UPR protein expression. Normal human fibroblasts were treated at various time points and the average of the maximum protein expression of BIP (78 kDa) and phosphorylated eIF2α (38 kDa) is plotted as in FIG. 2F. Actin (43 kDa) was used as a loading control and is the same blot as FIG. 2F. UT denotes untreated cells. M denotes marker lane. FIG. 4C shows XBP1 splicing. Normal human fibroblasts were treated. The expression of the unspliced form (XBP1-us; 33 kDa) and the activated and spliced form of XBP1 (XBP1-s; 54 kDa) was analyzed by immunoblotting. BP1-s is a larger protein than XBP1-us due to non-canonical mRNA splicing which results in a larger carboxy-terminal domain. The percentage of XBP1-s to XBP1-us increased with each treatment as shown (24 hr. time point). The average of the maximum expression of XBP1-s (within 24 hrs.) is plotted as in FIG. 2F. Actin was used as a loading control. (P=0.08 for the TSA treated values; * statistical significance ($p \leq 0.05$); Bars=SEM for $n \geq 3$ independent experiments).

Thus, the pro-survival capabilities of all three UPR branches were activated at the transcriptional, post-transcriptional, translational, and post-translational levels by treatment with these small molecules.

h. Small Molecule Activation of Autophagy

Figure 5:
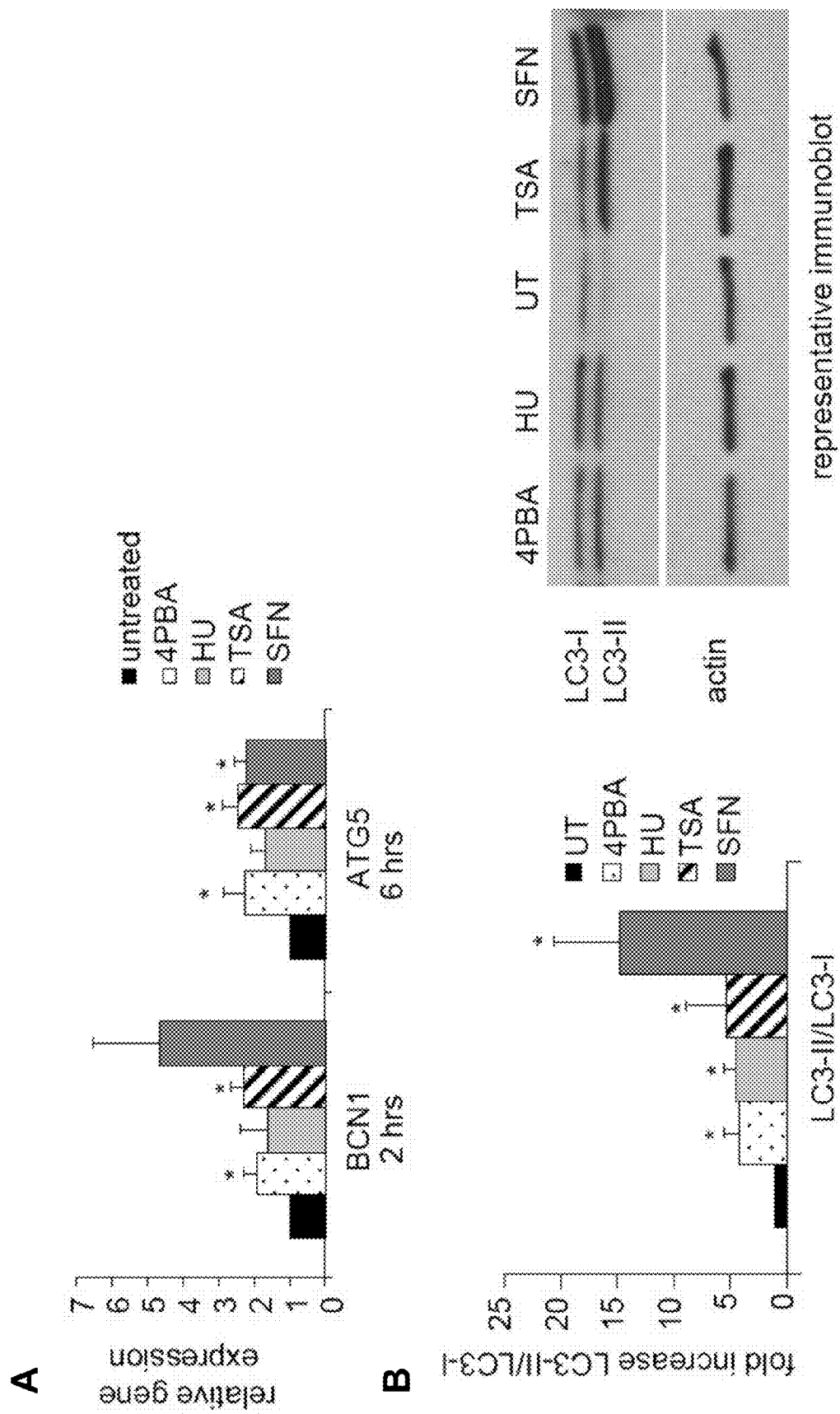
FIG. 5 (A-D) shows that autophagy and the antioxidant response are induced by treatment with 4PBA, HU, TSA, or SFN.
Figure 5:
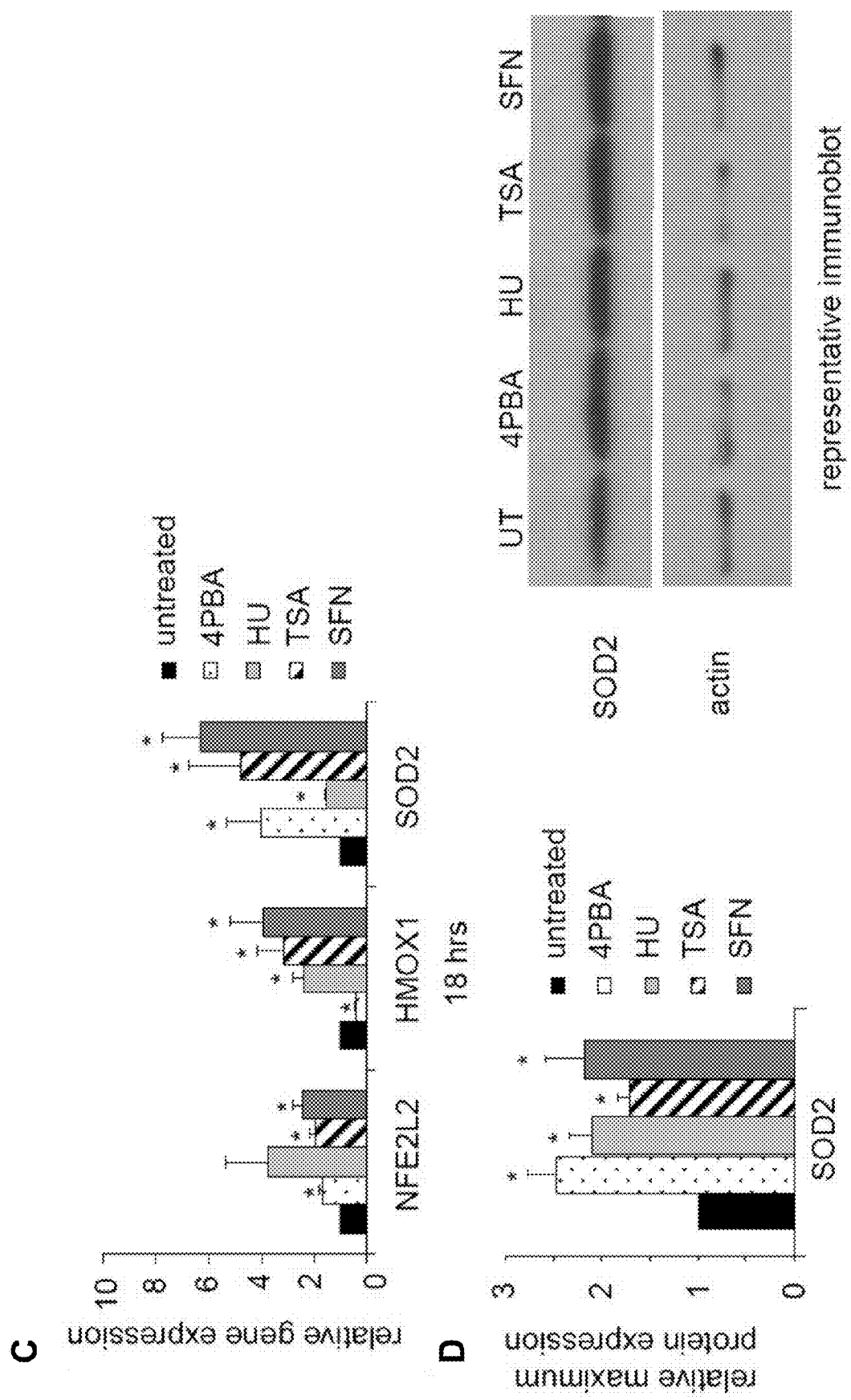

Adverse growth conditions increase the energetic demand on a cell, which in turn, stimulates the catabolic processes of autophagy to promote utilization of damaged and excess proteins and damaged organelles for cellular nutrients (Martinet et al., 2009). To monitor activation of autophagy, the expression of three classical autophagy markers was examined. The three classical autophagy markers are: (i) beclin-1 (BCN1), (ii) autophagy protein 5 (ATG5), and (iii) microtubule-associated protein 1 light chain 3 (LC3 or APG8). Autophagosome formation is signaled by the phosphorylation of BCN1 by JNK1 and is dependent on the conjugation of ATG5 and ATG12 and the cleavage (LC3-I) and phosphatidylethanolamine lipidation (LC3-II) of APG8. Treatment with 4PBA, TSA, or SFN increased BCN1 and ATG5 mRNA levels (FIG. 5A). FIG. 5A shows RT-PCR analyses of mRNA expression of autophagy genes. Normal human fibroblasts were treated as indicated. The expression of BCN1 and ATG5 were measured as described in FIG. 2E. After TSA treatment, the levels of ATG5 mRNA were measured in two independent experiments in duplicate. The p-value for the ATG5 HU treated samples is 0.10. The p-values for the BCN1 HU and SFN samples are 0.23 and 0.06, respectively.

After HU treatment, ATG5 mRNA levels also increased, but BCN1 mRNA levels were not reproducibly changed within six hours of treatment. Treatment with each of these small molecules significantly increased the proportion of LC3-II to LC3-I, a hallmark of autophagy activation (FIG. 5B). FIG. 5B shows immunoblot analyses of the cleavage and lipidation of autophagy protein APG8. Normal human fibroblasts were treated for 4 hrs.-24 hrs. and the average of the maximum proportion of APG8 LC-II (13 kDa), the cleaved and lipidated form of APG8, to APG8 LC3-I (17 kDa) is plotted as in FIG. 2F. A 24 hour time point is shown. Actin (43 kDa) was used as a loading control. UT denotes untreated cells. Therefore, treatment with each of the four small molecules activated the autophagy pathway.

i. Small Molecule Activation of the Antioxidant Response

The antioxidant response detoxifies the cell and regulates reduction-oxidation (redox) homeostasis by neutralizing the effects of reactive oxygen species (ROS) and reactive nitrogen species (RNS). ROS and RNS are second messengers of the adaptive cell survival response (Fedoroff 2006). The expression of three key components was examined—(i) nuclear factor erythroid 2-like 2 (NFE2L2), (ii) heme oxygenase 1 (HMOX1), and (iii) superoxide dismutase 2 (SOD2). NFE2L2, a transcription factor that binds the antioxidant response element, is involved in the chemoprotective response provided by SFN (Myzak et al., 2004). After treatment with 4PBA, HU, TSA, or SFN, NFE2L2 and SOD2 mRNA levels increased (FIG. 5C). FIG. 5C shows RT-PCR analyses of mRNA expression of antioxidant genes. Normal human fibroblasts were treated for 18 hours. The expression of NFE2L2, HMOX1, and SOD2 was measured as described in FIG. 2E. The p-value for the NFE2L2 HU measurements was 0.11.

HMOX1 mRNA levels significantly increased with HU, TSA, or SFN treatment and significantly decreased with 4PBA treatment. SOD2 protein levels also significantly increased (FIG. 5D). FIG. 5D shows immunoblot analyses of SOD2 protein expression. Normal human fibroblasts were treated for two to five days. The relative expression of SOD2 (26 kDa) is plotted for each treatment compared to UT cells as in FIG. 2F. Actin (43 kDa) was used as a loading control. (*statistical significance ($p \leq 0.05$); Bars=SEM for $n \geq 3$ independent experiments unless otherwise noted). Thus, cellular antioxidant defense mechanisms were induced at the transcriptional and translational levels by treatment with each of these small molecules.

j. HU And SFN do not Inhibit Class I and II HDACS

Figure 6:
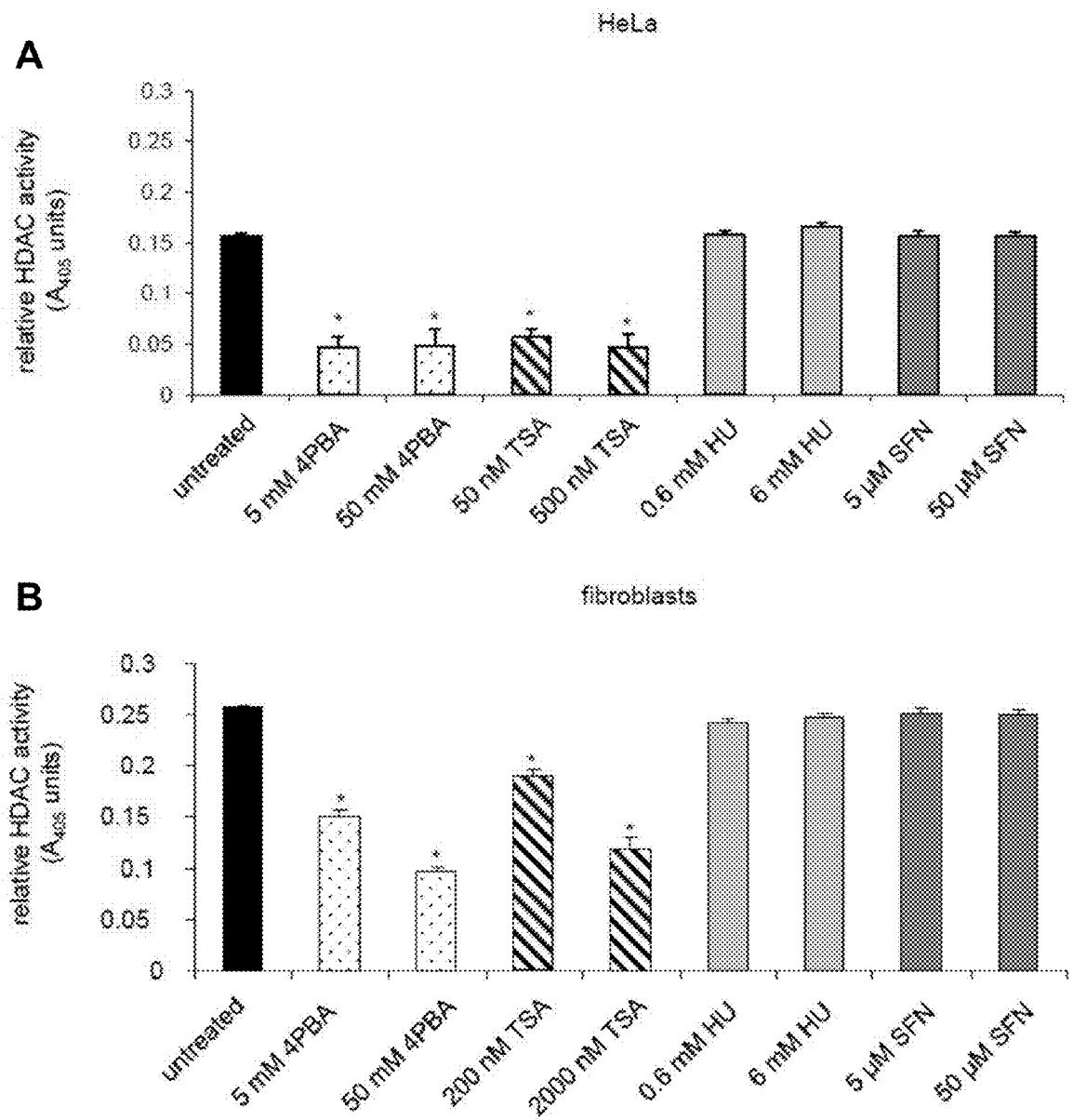
FIG. 6 (A-B) shows that HU and SFN do not inhibit class I and class II histone deacetylase activities.

These small molecules activate the stress proteome and share similar cellular responses in diverse disease models. Two of the small molecules, 4PBA and TSA, directly inhibit histone deacetylase activity in vitro (Jung 2001). Whether inhibition of class I and class II HDAC activities is a shared biochemical function that could account for the effects of all four small molecules was examined. Using lysates from HeLa cells and primary human fibroblasts, an in vitro colorimetric assay of HDAC activity was performed. Two concentrations of each small molecule were used. The first concentration was that used to treat primary human fibroblasts in the experiments reported herein, which minimally affects growth. The second concentration was ten times the first concentration and is lethal in cell culture. 4PBA and TSA significantly decreased HDAC activity when compared to untreated HeLa and human fibroblast lysates (FIG. 6A-B). However, neither concentration of HU nor SFN reduced class I or II HDAC activity in lysates. In FIG. 6, HDAC activity was measured using extracts from two cell lines as shown. (* p≤0.00009; paired t-test; Bars=SEM for n≥3 independent experiments).

A physiological increase in histone acetylation after SFN treatment of whole cells that may reflect a change in gene expression that is not the result of direct biochemical inhibition of HDAC enzymatic activity by SFN was demonstrated [Myzak et al., 2004]. While the inhibition of HDAC activity by 4PBA or TSA treatment may induce the stress proteome, HU and SFN induce the stress proteome independent of direct HDAC inhibition.

k. Beneficial Effects of SFN in Spinal Muscular Atrophy Cells are Dependent on the JNK Pathway, Autophagy, Mitochondrial Biogenesis and SIRT1 Activity To determine which of the drug-induced stress pathways are necessary for the therapeutic effects of these small molecules, their effects in spinal muscular atrophy fibroblasts were examined. Ninety-five percent of spinal muscular atrophy patients have a homozygous deletion of the telomeric SMN1 (chr 5q13) gene or gene conversion at exon 7 or 8 (Lefebvre et al., 1995). However, patients have one or more copies of a centromeric SMN1 pseudogene, SMN2. Compared with SMN1, SMN2 has a C to T transition within an exonic splice enhancer that results in the skipping of exon 7 (SMND7) and an unstable protein that is degraded (Sumner et al., 2003; Lorson et al., 1998). Only 15-30% of SMN2 transcripts include exon 7 and are full length (FL-SMN). Since the clinical severity of spinal muscular atrophy patients inversely correlates with the levels of FL-SMN transcript and SMN protein, therapeutic strategies that increase FL-SMN and SMN protein production offer promise.

If these three small molecules and SFN share a common therapeutic mechanism, SFN treatment should also increase FL-SMN mRNA and SMN protein expression. To determine whether a common effect of treatment with these four small molecules is the induction of the stress proteome, the following were examined: (i) the induction of mitochondrial biogenesis by these four small molecules in spinal muscular atrophy fibroblasts, (ii) the effect of SFN treatment on the expression of FL-SMN mRNA and SMN protein in spinal muscular atrophy, and (iii) the ability of inhibitors of the various stress pathways to block induction of FL-SMN mRNA and SMN protein expression.

Figure 7:
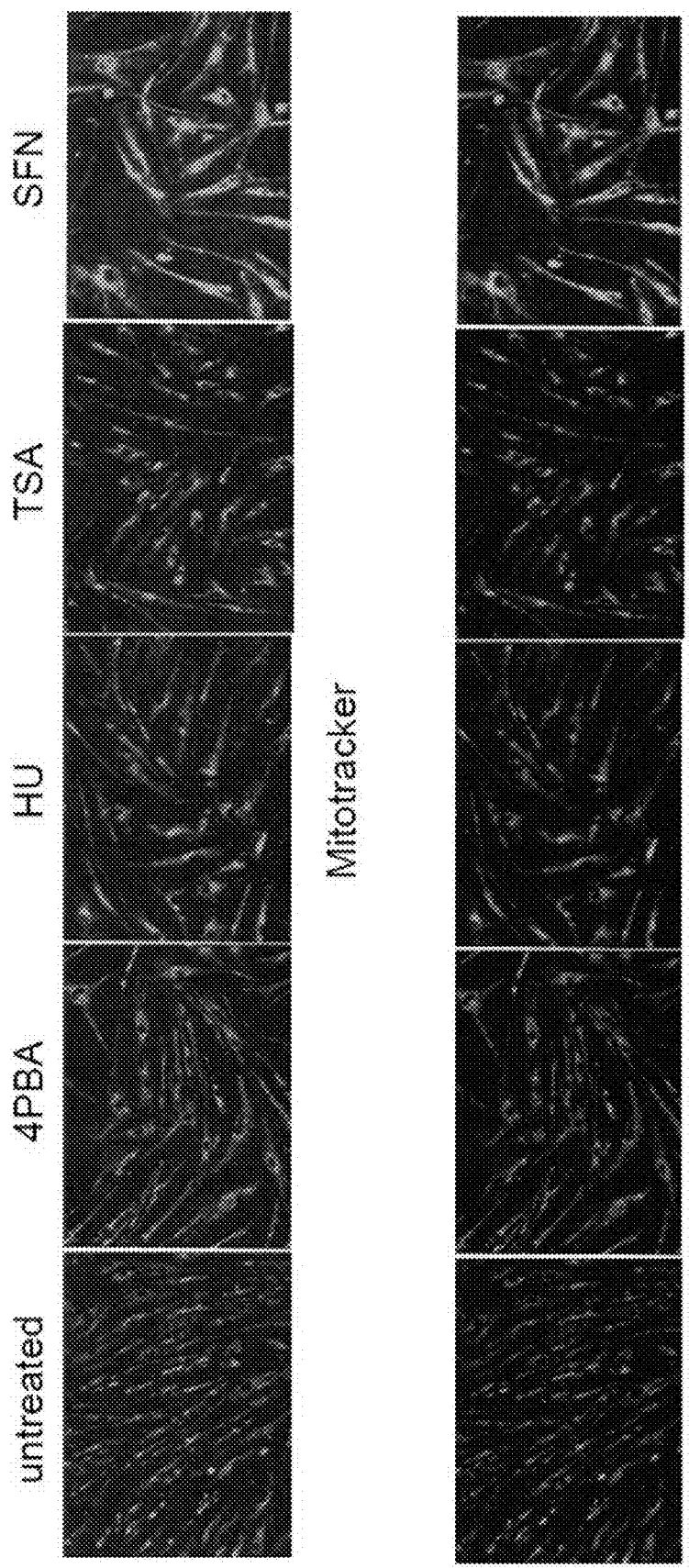
FIG. 7 shows the induction of mitochondrial biogenesis by 4PBA, HU, TSA, and SFN in spinal muscular atrophy fibroblasts.

Similar to treatment of X-linked adrenoleukodystrophy fibroblasts, K562 cells and normal human fibroblasts, treatment of spinal muscular atrophy fibroblasts with each of the four small molecules increased mitochondrial biogenesis as monitored by Mitotracker staining, a cell-permeant mitochondrion-selective dye (FIG. 7). FIG. 7 shows that mitochondrial biogenesis is induced in spinal muscular atrophy fibroblasts by 4PBA, HU, TSA or SFN treatment. Immunofluorescence staining for mitochondria using Mitotracker Red CMXROS. Spinal muscular atrophy fibroblasts were treated with 2.5 mM 4PBA, 300 mM HU, 100 nM TSA or 2.5 mM SFN for 5 days (×80 magnification).

SFN treatment significantly increased FL-SMN mRNA expression compared with total SMN transcription (FL-SMN plus SMND7) in two spinal muscular atrophy type I cell lines (GM09677 two copies SMN2 and GM00232 one copy SMN2) and one spinal muscular atrophy type III cell line (96-2906 four copies SMN2; FIG. 8A) (Sumner et al., 2003). Cell lines with greater numbers of SMN2 gene copies respond better to treatment.

Figure 8:
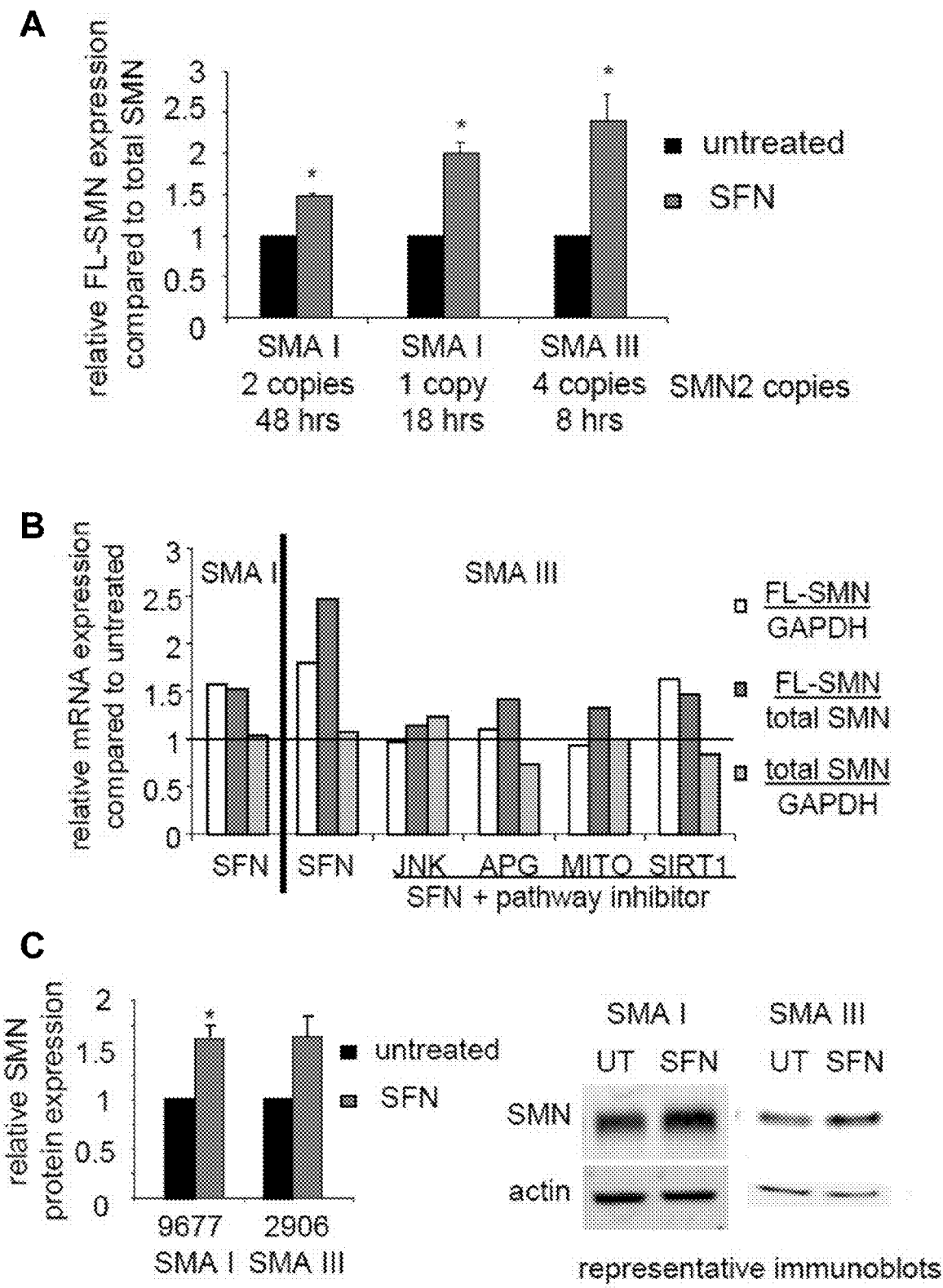
FIG. 8 (A-D) shows the induction of FL-SMN and SMN expression by SFN is dependent upon the JNK pathway, autophagy, mitochondrial biogenesis, and SIRT1 activity.
Figure 8:
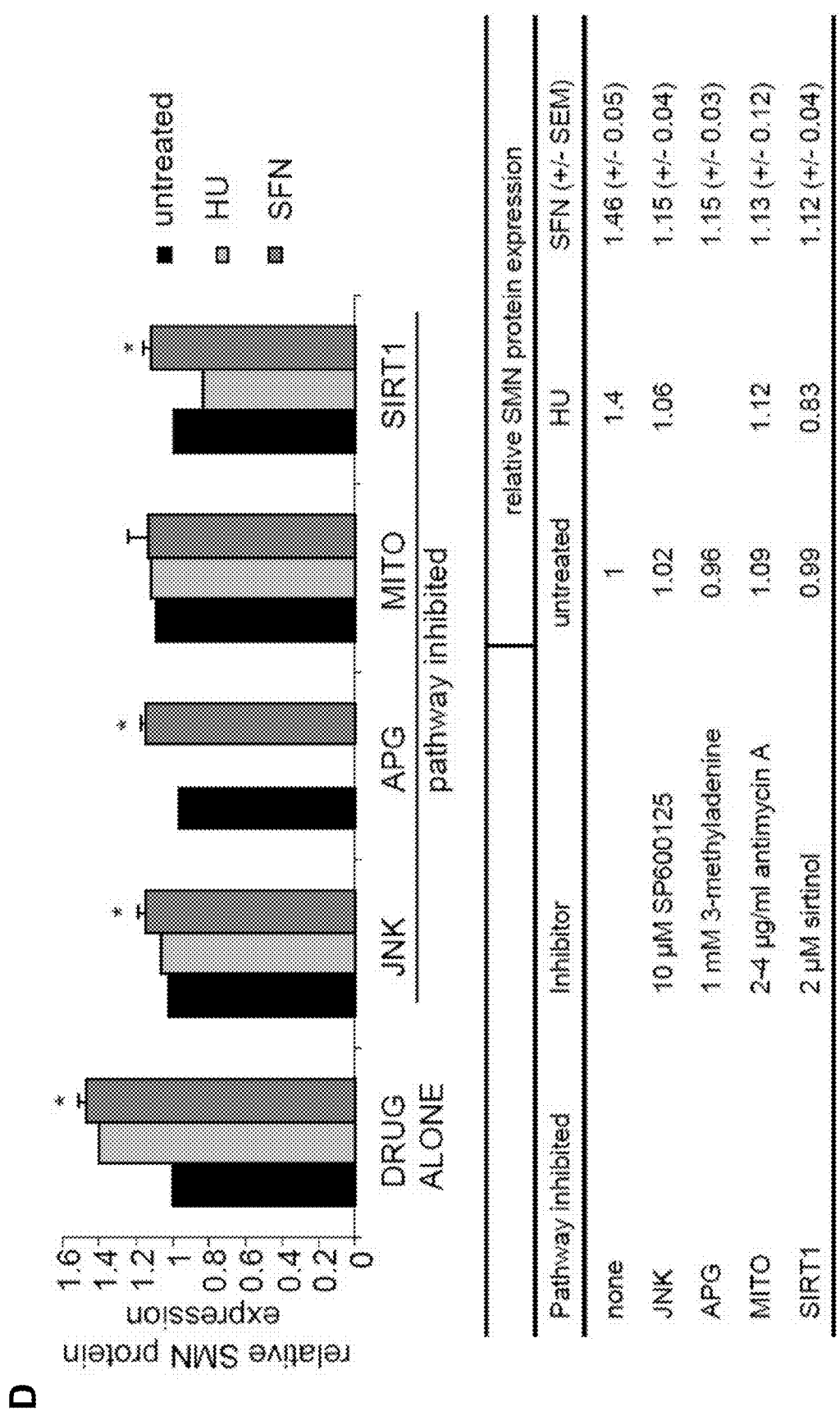

FIG. 8 shows the induction of FL-SMN mRNA expression and SMN protein expression by SFN is dependent on the JNK pathway, autophagy, mitochondrial biogenesis and SIRT1 activity. For example, FIG. 8A shows the RT-PCR analyses of FL-SMN mRNA expression compared with total SMN transcript expression. Type I and type III spinal muscular atrophy (SMA I or SMA III) fibroblasts were treated with SFN for the indicated times. The relative fold increase in the ratio of FL-SMN/total SMN transcripts compared with the untreated cell line (normalized to 1) is plotted. Cell lines from left to right are GM09677, GM00232 and 2906. N≥2 independent experiments.

FIG. 8B shows RT-PCR analyses of FL-SMN and total SMN mRNA expression. Spinal muscular atrophy fibroblasts were treated with 1.5 mM SFN alone for 51 hr. (SMA I, GM09677) or treated with 0.5 mM SFN for 8 hr. (SMA III, 2906) with or without 12.5 mM SP600125 (JNK inhibitor), 2.5 mM 3-methyladenine (autophagy inhibitor, APG), 5 mg/mL antimycin A (mitochondrial inhibitor, MITO) or 3 mM sirtinol (SIRT1 inhibitor). The fold increases in FL-SMN expression compared with either GAPDH or total SMN expression and the fold increase in total SMN expression compared with GAPDH expression after SFN treatment is plotted. Untreated values were normalized to 1 and are indicated by the horizontal line. (n=1 per cell line, performed in duplicate)

FIG. 8C shows immunoblot analyses of SMN protein expression. Spinal muscular atrophy type I (SMA I; GM09677, n=7) or type III (SMA III; 2906, n=2) fibroblasts were treated with either 1.5 mM SFN or 0.5-2 mM SFN, respectively, for 48-72 hr. The average of the relative expression of SMN protein (39 kDa) is plotted. Actin (43 kDa) was used as a loading control.

FIG. 8D shows a summary of the effects of stress pathway inhibitors on SMN protein expression. Spinal muscular atrophy type I (SMA I; GM09677) fibroblasts were treated with either 300 mM HU (n=1) or 1.5 mM SFN (n≥3) in the presence or absence of 10 mM SP600125 (JNK inhibitor), 1 mM 3-methyladenine (APG inhibitor), 2-4 mg/ml antimycin A (MITO inhibitor) or 2 mM sirtinol (SIRT1 inhibitor) for 48 h. SMN protein expression was measured by quantitative immunoblot analyses using actin as a loading control. Fold increases in SMN protein expression are plotted and represented numerically in the table below the graph. Untreated values are normalized to 1. (*P≤0.05; bars=SEM).

After SFN treatment, the relative expression of FL-SMN transcripts increased when normalized to either GAPDH transcript levels or to total SMN transcript levels (FIG. 8B). However, total SMN transcript levels remained unchanged when normalized to GAPDH transcript levels after treatment. Therefore, SFN treatment increases the quantity of FL-SMN transcripts by enhancing the inclusion of exon 7 rather than increasing overall transcriptional expression from the SMN2 gene.

The reduction in very long-chain fatty acid levels in X-linked adrenoleukodystrophy fibroblasts by 4PBA was dependent on the induction of mitochondrial biogenesis and that the induction of HbF production in K562 cells by HU was dependent on the JNK pathway and mitochondrial function (FIGS. 1B and 1D and FIG. 2D). To determine which stress pathways are necessary for the increase in FL-SMN production, spinal muscular atrophy fibroblasts were co-treated with SFN and either SP600125, an inhibitor of the JNK pathway (Bennett et al., 2001), 3-methyladenine, an inhibitor of the autophagy pathway (Seglen et al., 1982), antimycin A, a mitochondrial inhibitor (Ranganathan et al., 2009), or sirtinol, an inhibitor of SIRT1 activity (Grozinger et al., 2001). The concentration of each inhibitor did not affect cell growth or viability. SIRT1, an NAD+-dependent deacetylase, is known to regulate cellular stress responses, cellular metabolism and cellular survival (Salminen et al., 2009). Specifically, SIRT1 inhibition reduces the induction of HSR genes (Westerheide et al., 2009); SIRT1 activity enhances SOD2 expression (Anastasiou et al., 2006); SIRT1 negatively regulates the mammalian target of rapamycin triggering autophagy (Haigis et al., 2010); and SIRT1 activates mitochondrial biogenesis via the stress-responsive transcription factor PGC1a (Yu et al., 2009). The yeast ortholog Sir2 is necessary for the induction of mitochondrial biogenesis by 4PBA or HU in Saccharomyces cerevisiae (Cha 2010). There were no marked changes in SIRT1 protein expression after treatment of normal human fibroblasts with 4PBA, HU, TSA or SFN. However, SIRT1 can be activated by various post-translational changes. Therefore, the potential involvement of SIRT1 in the therapeutic effects of these drugs by inhibition studies was evaluated. Biochemically blocking the JNK pathway, the autophagy pathway, induction of mitochondrial biogenesis and SIRT1 activity prevented the increase in FL-SMN transcript levels in SFN-treated spinal muscular atrophy fibroblasts indicating the necessity and potential concerted action of each of these pathways for the therapeutic response to SFN treatment (FIG. 8B).

Figure 9:
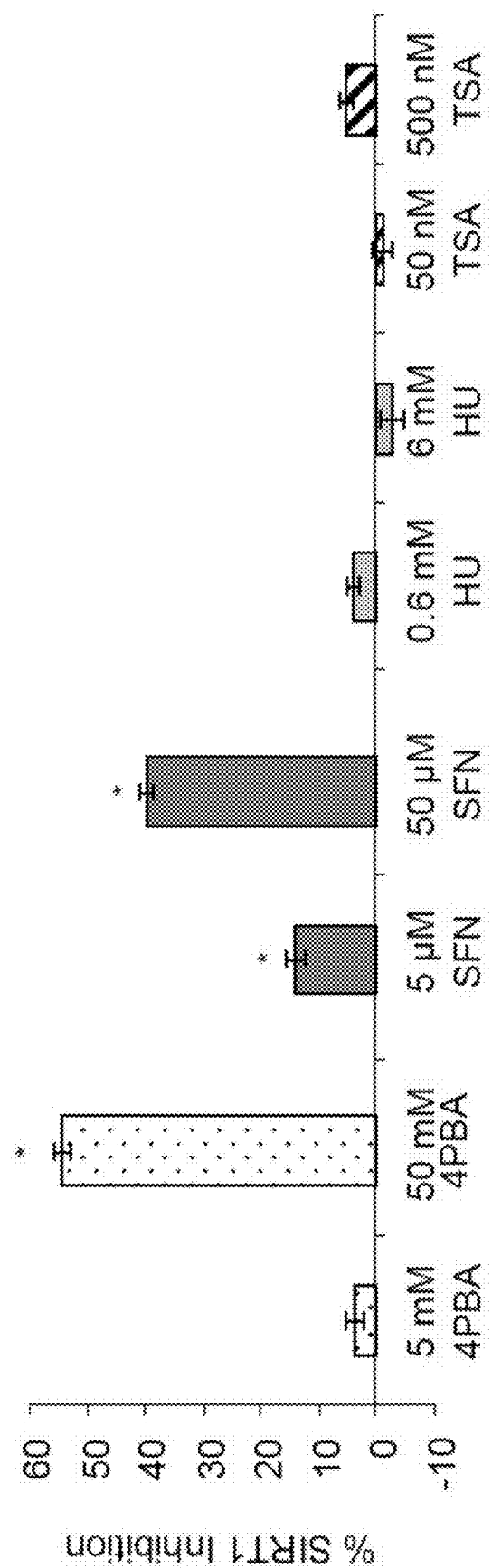
FIG. 9 shows that the biochemical SIRT1 activity is not required for the induction of the stress proteome by 4PBA, HU, TSA, and SFN.

To further demonstrate that induction of these various stress pathways is necessary for the therapeutic effects of the small molecules under study, the expression of total SMN protein expression after either SFN or HU treatment in the presence or absence of the stress pathway inhibitors was monitored. After 48-72 hr. of treatment, SFN increased SMN protein expression 1.57-fold in spinal muscular atrophy type I fibroblasts and 1.64-fold in spinal muscular atrophy type III fibroblasts (FIG. 8C). In separate experiments, HU or SFN treatment increased SMN protein expression 1.4- and 1.46-fold, respectively (FIG. 8D). The pharmacologically induced increase in SMN protein expression was significantly reduced by the various stress pathway inhibitors, indicating that the increase in SMN protein expression by both HU and SFN was dependent on activation of the JNK pathway, autophagy, mitochondrial biogenesis and SIRT1 (FIG. 8D). At the concentrations used, the stress pathway inhibitors had no effect on basal levels of SMN protein expression. The magnitude of the increases in FL-SMN expression and SMN protein expression in SFN-treated spinal muscular atrophy cells compared with untreated cells is similar to that observed after 4PBA, HU or TSA treatment in SMA fibroblasts (Andreassi et al., 2004; Grzeschik et al., 2005; Avila et al., 2007). Since SFN induction of FL-SMN transcript expression and SMN protein expression is dependent on the JNK pathway, autophagy pathway, mitochondrial biogenesis and SIRT1, the therapeutic potential of the activation of the stress proteome may require the concerted action of each of the individual stress pathways.

l. SIRT1 Activation is not a Common Mechanism of Action of 4PBA, HU, TSA and SFN To determine whether SIRT1 activation was a common biochemical activity of the small molecules under study, a fluorescence-based in vitro SIRT1 activity assay was performed with two concentrations of each drug: that used to treat normal primary human fibroblasts in the experiments reported here (low), and 10 times that concentration, which is lethal in cell culture (high). HU and TSA had no effect on SIRT1 activity, whereas 4PBA (50 mM; high) and SFN (5 and 50 mM) significantly inhibited SIRT1 activity by 54, 14 and 40%, respectively (FIG. 9). This was a non-cell-based assay, and therefore, it is difficult to determine the effects of 4PBA and SFN on SIRT1 activity in vivo. Regardless, while SIRT1 activation may play a role in the induction of cellular stress responses (Anastasiou et al., 2006), direct biochemical activation or inhibition of SIRT1 is not necessary for the common pharmacological induction of the adaptive cell survival response by all four small molecules.

FIG. 9 shows that biochemical SIRT1 activation is not necessary for the induction of the stress proteome by 4PBA, HU, TSA and SFN. SIRT1 activity assay. SIRT1 activity was measured by incubating an acetylated lysine substrate with human recombinant SIRT1, cosubstrate NAD+ and the indicated concentration of each small molecule. The percent inhibition of SIRT1 is plotted. (Bars=SEM for triplicate measurements; *$p \leq 0.05$; paired t-test).

Collectively, the data presented herein demonstrate that pharmacological small molecules or agents without known overlapping molecular functions induce mitochondrial and peroxisomal biogenesis and the transcription and translation of signature components of the adaptive cell survival response (HSR, UPR, autophagy, and antioxidant response). Under adverse cellular conditions, mitochondria induce either the endogenous adaptive cell survival response reestablishing homeostasis (mild stress) or apoptosis (severe stress) (Lee et al., 2005). The small molecules studied herein exhibited a biphasic or hormetic dose response (Calabrese et al., 2010). At the low doses used herein, the four small molecules activated the stress proteome and produced beneficial effects; and at higher doses, the four small molecules were cytotoxic. The pharmacological induction of mitochondrial biogenesis is consistent with the significant increase in energy expenditure required for metabolic adaptation to increased cellular stress.

The results presented herein demonstrate the therapeutic importance of the pharmacological induction of mitochondrial biogenesis in XALD cells and K562 cells, a model of HbF induction. The reduction in VLCFA levels in 4PBA-treated XALD fibroblasts and the increase in HbF-producing cell number in HU-treated K562 cells depended on the stress-activated JNK signaling cascade and the subsequent induction of mitochondrial biogenesis. Since the small molecules have different known functions (Table 2) and different chemical structures, yet elicited similar molecular responses, these data demonstrate generally that small molecules with varying functions can activate the adaptive cell survival response and elicit similar therapeutic responses.

Beneficial therapeutic effects that improve disease pathology and that are independent of altering the specific genetic mutation have been well documented. Examples include TSA treatment of Duchenne's muscular dystrophy models, losartan treatment of Marfan's syndrome patients, and 4PBA, HU, or TSA treatment of spinal muscular atrophy models (Lunn et al., 2008; Minetti et al., 2006; Habashi et al., 2006). Such examples provide an elegant illustration of corrective biological responses from indirect interventions.

A therapeutic role for adaptive survival pathways has been observed in a range of diseases. Overexpression or pharmacological induction of heat shock proteins (i) corrected the defect in Niemann-Pick patient cell lines, a lysosomal storage disorder, (ii) ameliorated the phenotype of spinal bulbar muscular atrophy (SBMA) mouse models, and (iii) reduced protein aggregation in studies of Huntington's disease, a neurological disorder (Evans et al., 2010). Induction of the UPR proteins XBP1 and ATF6 protected against ischemia-reperfusion injury (Toth et al., 2007). Pharmacological induction of autophagy or overexpression of autophagy proteins protected against ischemia-reperfusion injury, improved mutant protein clearance, and reduced protein toxicity in cell and animal models of Huntington's disease, Alzheimer's disease, Parkinson's disease, amyotrophic lateral sclerosis (ALS), spinocerebellar ataxia, and SBMA (Martinet et al., 2009; Madeo et al., 2009). Antioxidant and 4PBA treatment improved insulin sensitivity and glucose homeostasis in diabetic mouse models (Ozcan et al., 2006; Liu et al., 2009). 4PBA-induced mitochondrial biogenesis can help to normalize glucose levels because mitochondrial dysfunction is a key contributor to insulin resistance. 4PBA-induced expression of SOD2 increases neuroprotection in ALS (Petri et al., 2006). Improved mitochondrial membrane potential and increased peroxisome proliferation induced by 4PBA treatment promoted neuronal integrity in Alzheimer's studies (Santos et al., 2005). Although 4PBA, HU, TSA, and SFN treatment induced all four adaptive survival pathways examined, the induction of all pathways may not be necessary for a therapeutic outcome in every responsive disease.

The induction of the adaptive cell survival response and the subsequent reestablishment of cellular homeostasis explain why these diverse pharmacological small molecules or agents produce similar therapeutic effects in such a variety of disease models (Table 1). The diseases responsive to these small molecules have mild cellular abnormalities, i.e., the cells are viable even though their suboptimal function may lead to severe clinical manifestations. The pharmacological enhancement of the adaptive cell survival response and the subsequent reestablishment of cellular homeostasis beneficially alters disease-related metabolic stress, promotes cell viability, and ameliorates some mild cellular genetic abnormalities without directly targeting the disease-causing gene. For example, enhancement of autophagy in the SOD1 transgenic ALS mouse model cleared protein aggregates and significantly increased lifespan (Madeo et al., 2009). Also, TSA treatment of Abcd1−/− fibroblasts normalized β-oxidation levels of VLCFA independent of Abcd1 or Abcd2 expression (McGuiness et al., 2003). This indirect approach to therapy offers the advantage of pharmacologically modulating the adaptive capacity of the endogenous cellular machinery, specifically the stress proteome and mitochondrial function, to compensate for metabolic abnormalities and improve cellular function. This provides a rationale for the treatment of diseases whose specific genetic abnormalities are unknown, including many complex disorders, and may shorten the time to treatment for some currently untreatable diseases.

The four small molecules disclosed herein can activate the stress proteome via their known biochemical activities or via uncharacterized molecular interactions within cells. For example, in K562 cells, the production of ROS increases F-cell production after SB and TSA treatment, but not after HU treatment (Hsiao et al., 2006). This result indicates that F-cell production is stimulated by differing pathways. Identification of the cellular responses necessary for downstream therapeutic effects of interest, i.e., mitochondrial biogenesis, can assist screening for small molecules with optimal clinical effects.

The small molecules investigated here were identified by effects on disease outcomes. Establishment of the therapeutic potential of the adaptive cell survival response by these small molecules provides targets for the identification of more efficacious small molecules with lower toxicity. The exploitation of the innate cellular survival program may ameliorate disease symptoms in a spectrum of disorders with mild cellular phenotypes without targeting a specific molecule or signaling pathway for each individual disease. The amenable disorders not only include those with mitochondrial or peroxisomal defects, increased oxidative stress, or protein conformation or trafficking defects, but also include aging disorders and complex diseases with unknown genetic etiology and mild cellular phenotypes. Therapy that targets homeostatic regulation could have a profound effect on medicine.

iii) Stimulation of HSP by Sulforaphane

Sulforaphane stimulated HSP and mitochondrial biogenesis in several genetic disorders. The data provided herein demonstrated that sulforaphane induces known cellular stress response pathways and heat shock proteins that protect cells from mild metabolic disturbances. The stress proteome response to low doses of sulforaphane includes effects on redox regulation, DNA damage sensing and repair, molecular chaperones, fatty acid and lipid metabolism and energy metabolism.

Sulforaphane and related HDAC and non-HDAC inhibitors are hormetic drugs that induce a general "cell-protective" response, as demonstrated in a number of neurological diseases. The cellular repair effects contrast sharply with the cellular and genetic damage reported to occur following exposure to high doses of the same drugs.

Sulforaphane induces known cellular stress response pathways and heat shock proteins that protect cells from mild metabolic disturbances. The stress proteome response to low doses of sulforaphane includes effects on redox regulation, DNA damage sensing and repair, molecular chaperones, fatty acid and lipid metabolism and energy metabolism (Keefer et al., 2006). The data presented herein shows the effects of sulforaphane on the heat shock response. mRNA expression of heat-shock proteins genes was markedly increased (3-7-fold) in normal human fibroblasts following exposure to 5 micromolar (µM) sulforaphane. The heat shock proteins affected are: HSP40, USP70, and USP90.

Heat shock proteins and ubiquitin/26 S proteasome subunits were induced in the liver of mice at time points that were 3- and 12-hours after treatment with a single dose of sulforaphane (90 mg/kg) by gavage (Hu et al., 2005). In HeLa cells and COS1 cells, sulforaphane enhanced proteasomal activity. Sulforaphane also increased the gene expression of Hsp27 by activating heat shock factor 1 (HSF1), which is the major transcription factor that regulates the expression of heat shock proteins (Gan et al., 2010, which is incorporated herein in its entirety by reference). In HeLa cells, sulforaphane treatment caused dissociation of HSF1 from its negative regulators Hsp90 and Hsp70, followed by nuclear translocation of the transcription factor. In a luciferase reporter system, sulforaphane activated HSF1 mediated transcription of the reporter, and the expression of the endogenous HSF1-target genes Hsp70 and Hsp27.

The mechanism of HSF1 activation by sulforaphane is presently unknown. However, HSF1 is activated by electrophiles, such as the quinone methide celastrol, hydrogen peroxide, menadione, arsenic trioxide, 15-deoxy-PGJ2, and 4-hydroxynonenal. It is possible that sulforaphane modifies directly specific cysteine residues of HSF1 thus altering the binding of HSF1 to its negative regulators Hsp90 and Hsp70 and/or the ability of the transcription factor to trimerize and bind to DNA. Another interesting possibility is that sulforaphane, through its ability to inhibit the activity of the cytoplasmic non-histone protein deacetylase HDAC6, and consequently enhance Hsp90 acetylation (Gibbs et al., 2009), may inhibit its association with HSF1.

iv) In Vitro Sulforaphane Studies

As described herein, in vitro studies demonstrated that sulforaphane (SF) stimulated the metabolic pathways that comprise the adaptive cellular stress response. Mitochondrial and peroxisomal biogenesis were increased 2- to 3-fold as compared to untreated cells. In addition, the JNK pathway was activated and the concentration of mitochondrial transcription factors was increased 2- to 4-fold.

Heat Shock Response (HSR) induction is a hallmark of the adaptive cell survival response. Sulforaphane (SF) increased the transcription of HSP70 by 7-fold and increased the transcription of both HSP40 and HSP 90 by 3-fold. SF increased the total HSP70 and HSP90 protein levels by 3 to 4-fold. The pharmacological induction of HSR mRNA and protein expression was similar to that caused by mild heat shock. Sulforaphane treatment activated the pro-survival capabilities of all three branches of the UPR at the transcriptional, post-transcriptional, translational, and post-translational levels. The central UPR regulator glucose regulated protein 78 (BIP) was increased 2-3 fold at the transcriptional and translational levels. SF treatment also increased ATF4 and CHOP mRNA expression 4-5 fold, modestly increased eIF2a phosphorylation, and increased the total amount of XBP1 protein and the amount of spliced XBP1 protein 3-4.

The expression of three classical autophagy markers, beclin-1 (BCN1), autophagy protein 5 (ATG5), and microtubule-associated protein 1 light chain 3 (LC3 or APG8), was examined after SF treatment. BCN1 and ATG5 mRNA levels increased 5-fold and 3-fold, respectively, and the proportion of LC3-II to LC3-I, a hallmark of autophagy activation, was significantly increased. The cellular antioxidant defense mechanisms were induced at the transcriptional and translational levels. The expression of three key components was also increased: nuclear factor erythroid 2-like 2 (NFE2L2) by 3-fold, hemeoxygenase 1 (HMOX1) by 6-fold, and superoxide dismutase 2 (SOD2) by 4-fold. NFE2L2, a transcription factor that binds the antioxidant response element, is known to be involved in the chemoprotective response provided by sulforaphane.

v) Effect of Fever, Cellular Stress, and Hydroxyurea in Autism

Autism is a clinically heterogeneous disorder, which results from a variety of nonlethal genetic disorders and epigenetic effects that affect related metabolic pathways. Some of these pathways respond to pharmacological stimulation of cellular stress responses. The genetic and environmental factors underlying its various forms are the focus of intense research. While the underlying cellular mechanisms are heterogeneous and can be considered marginal with respect to toxicity and disturbed homeostasis, the combined effects of these mechanisms, especially over, generate severe clinical results. For example, the rapid onset and transient behavioral improvements that occur during fever in ~38% of children with autism may be explained by underlying changes in gene expression, cellular physiology, neural transmission, or signal processing.

Furthermore, data indicate that due to chronic hypoxia, sickle cell disease (SCD) may be protective against the development of autism during infancy (i.e., SCD is negatively correlated with autism). Both fever and SCD may activate stress responses that improve cell survival by enhancing cellular metabolic pathways involved in homeostasis. Induction of the stress proteome involves several interconnected pathways that maintain molecular integrity.

To this end, hydroxyurea (HU) is an antineoplastic agent that significantly improves the quality of life of children and adults with sickle cell disease (SCD). HU has been reported also to improve cognitive function in children with SCD. (Puffer et al., 2007). HU has been tested for toxicity in children ranging in age from infancy to adolescence and is FDA-approved for use in adults with SCD. Moreover, HU has been effective in the treatment of SCD due to the increased expression of fetal hemoglobin. Specifically, it decreases the incidence of strokes, improves cognitive function and is now undergoing clinical trials in infants with SCD.

HU is a ribonucleotide reductase and non-histone deacetylase (HDAC) inhibitor that crosses the blood-brain barrier. HU has a hormetic effect: although toxic at high doses, at low doses, HU stimulates expression of the general cellular stress response and gene expression (e.g. the stress proteome). Data shown herein demonstrate that HU induced the known cellular stress pathways that protect cells from mild metabolic disturbances. The stress proteome response to low doses of HU includes effects on redox regulation, DNA damage sensing and repair, molecular chaperones, fatty acid and lipid metabolism and energy metabolism. (Keefer et al., 2006). HU and related HDAC and non-HDAC inhibitors are hormetic drugs that induce a general "cell-protective" response, as demonstrated in SCD as well as X-linked adrenoleukodystrophy (ALD) (Wei et al., 2000; McGuinness et al., 2001), fragile X syndrome, and spinal muscular atrophy (SMA) (Liang et al., 2006). The cellular repair effects contrast sharply with the cellular and genetic damage reported to occur following exposure to high doses of the same drugs.

Thus, HU is likely to compensate for several abnormal cellular functions in autism, e.g., mitochondrial dysfunction (Weissman et al., 2008), oxidative stress (James et al., 2009) and neuroimmune pathology (Vargas et al., 2005). Stimulation of the stress proteome by HU at low doses is likely to lead to improved clinical function in adolescents and adults with well-characterized autism.

Administration of hydroxyurea (HU) in adolescents and adults with autism is evaluated in a study designed to ensure safety and obtain efficacy data. HU is chosen based on its effects on the stress proteome in vitro and based on clinical observations of improvements (e.g., social responsiveness) in persons with autism during fever. (Curran et al., 2007).

The hybrid design of the study incorporates double masking, placebo control, and randomization to enhance the robustness of early outcome data. The objects of the experiment are as follows: (1) determine whether treatment with HU administered within a specified dose range is safe (i.e., toxicity); (2) determine whether treatment with HU administered within a specified dose range is well tolerated by autistic male adolescents and adults (i.e., side effects and adverse events); (3) determine whether there is evidence of measurable effects on behavioral symptoms; (4) determine whether there is evidence that treatment within the specified range has observable activity affecting social responsiveness, the most disabling core trait of autism; and (5) determine the proposed mechanism is supported by key cellular biomarkers (i.e., proof of principle).

Forty-five male adolescents (13-18 years) and adults (19-30 years) are randomly assigned to receive either HU (n=30, at 2 month escalating intervals: 10, 15 and 20 mg/kg/day) or placebo (n=15). Quantitative autism traits are assessed using the ADI-R, Social Responsiveness Scale (child and adult forms), Clinical Global Impression Scale (CGI) and Autism Behavior Checklist (ABC). Prior to each dose escalation and at the end of the study, the ADI-Current State Algorithm, SRS, CGI, and ABC are performed. Medical exams and laboratory monitoring are performed at regular intervals to observe for unanticipated signs of toxicity, and stopping rules applied by safety monitors. Statistical analyses of data are used to describe the study sample, using individual trends for each subject. As the placebo effect in drug studies of autism is frequently marked, the duration of treatment and rigorous blinding of the present study is sufficient to overcome this effect.

Data demonstrate that HU and related drugs activate cellular repair in cultures from a variety of genetic disorders, such as fragile X syndrome, ALD and SMA, as well as SCD, which are etiologically and clinically diverse.

vi) Effect of Hydroxyurea on Nitric Oxide in Autism

Autism is a clinically heterogeneous disorder and the genetic and environmental factors underlying its various forms are the focus of intense research. While the underlying cellular mechanisms are heterogeneous and can be considered marginal with respect to toxicity and disturbed homeostasis, the combined effects of these mechanisms, especially over, generate severe clinical results.

Hydroxyurea (HU), an antineoplastic agent that significantly improves the quality of life of children and adults with sickle cell disease (SCD), has been reported also to improve cognitive function in children with SCD. (Puffer et al., 2007). HU has been tested for toxicity in children ranging in age from infancy to adolescence and is FDA-approved for use in adults with SCD. HU is a ribonucleotide reductase and non-histone deacetylase (HDAC) inhibitor that crosses the blood-brain barrier. HU has a hormetic effect: although toxic at high doses, at low doses it stimulates expression of the general cellular stress response and gene expression (e.g., the production of fetal hemoglobin in SCD).

In autism, both enhancement of under-expressed genes and nitric oxide (NO) availability to the brain occur in response to treatment with HU. HU stimulates NO production (Lou et al., 2009) and has roles in neurodevelopment in ensuring synaptic plasticity and metasynaptic columnar organization (Gustafsson et al., 2004; Guix et al., 2005. HU simulates the effects of fever in autism at the cellular level by stimulating mild cellular stress.

Hydroxyurea is a ribonucleotide reductase and non-histone deacetylase (HDAC) inhibitor that crosses the blood-brain barrier. HU has a hormetic effect: although toxic at high doses, at low doses it stimulates gene expression (e.g., the production of fetal hemoglobin in SCD). The stress proteome response to low doses of HU includes effects on redox regulation, DNA damage and sensing and repair, molecular chaperones, fatty acid and lipid metabolism and energy metabolism. (Keefer et al., 2006). HU and related HDAC and non-HDAC inhibitors are hormetic drugs that induce a general cell protective response, as demonstrated in SCD as well X-linked adrenoleukodystrophy. (Wei et al., 2000; McGuinness et al., 2001). The cellular repair effects contrast sharply with the cellular and genetic damage reported to occur following exposure to high doses of the same drugs.

The effect of HU in autism is evaluated to ensure safety and efficacy (Piantadosi et al., 2005). The hybrid study design incorporates double masking, placebo control, and randomization to enhance the robustness of early outcome data. The objectives of the study are as follows: (1) whether HU treatment administered within a specified dose range is safe (i.e., toxicity); (2) whether HU treatment administered within a specified dose range is well tolerated by autistic male adolescents and adults (i.e., side effects and adverse events); (3) whether there is evidence of measurable effects on behavioral symptoms; (4) whether there is evidence that treatment within the specified range has observable activity affecting social responsiveness, which is a core trait of autism, and (5) whether the levels of cellular biomarkers support the proposed mechanism (i.e., proof of principle).

Male adolescent (n=15, ages 13-18 years) and adults (n=30, ages 19-30) are randomly assigned to receive either HU (at 2 month escalating intervals: 10, 15 and 30 mg/day) or placebo. Quantitative autism traits are assessed using the ADI-R, Social Responsiveness Scale (child and adult forms) (Constantino et al., 2005), Clinical Global Impressions Scale (CGI), and Autism Behavior Checklist (ABC). Prior to each dose escalation and at the end of the study, the ADI-Current State Algorithm, SRS, CGI, and ABC are performed. Medical exams and laboratory monitoring are performed at regular intervals to observe for signs of toxicity, and stoppage rules applied by safety monitors. Statistical analyses of data are used to describe the study sample, using individual trends for each subject. As the placebo effect in drug studies of autism is frequently marked, the duration of treatment and rigorous blinding of the present study is sufficient to overcome this effect.

Stimulation of the stress proteome and increased NO production by HU at low doses lead to improved clinical function in adolescents and adults with well characterized autism. HU compensates for several abnormal cellular functions in autism, e.g., mitochondrial dysfunction (Weissman et al., 2008), oxidative stress (James et al., 2009), and neuroimmune pathology (Vargas et al., 2005).

The data demonstrate that HU and related drugs activate cellular repair in cultures from a variety of rare genetic disorders and SCD, which are etiologically and clinically diverse.

G. References

Akerfelt M, et al. 2010. Heat shock factors: integrators of cell stress, development and lifespan. Nat Rev Mol Cell Biol. 11(8): 545-555.

Aman et al. 1985. Improvements on the Aberrant Behavior Checklist. Am J Ment Def. 89: 485-491.

Baird L, et al. 2011. The cytoprotective role of the Keap1-Nrf2 pathway. Arch Toxicol. 85:241-272.

Bennett B L, et al. 2001. SP600125, an anthrapyrazolone inhibitor of Jun N-terminal kinase. Proc Natl Acad Sci USA. 98: 13681-13686.

Bergen A W, et al. 1999. An Asian-Native American paternal lineage identified by RPS4Y resequencing and by microsatellite haplotyping. Ann Hum Genet. 63: 63-80.

Calabrese V, et al. 2010. Cellular stress responses, the hormesis paradigm, and vitagenes: novel targets for therapeutic intervention in neurodegenerative disorders. Antioxid Redox Signal. 13: 1763-1811.

Chiurazzi P, et al. 1999. Synergistic effect of histone hyperacetylation and DNA demethylation in the reactivation of the FMR1 gene. Hum Mol. Genet. 8: 2317-2323.

Choo-Kang L R, et al. 2001. Induction of HSP70 promotes DeltaF508 CFTR trafficking. Am J Physiol Lung Cell Mol. Physiol. 281: L58-68.

Clark M S, et al. 2009. Triggers of the HSP70 stress response: environmental responses and laboratory manipulation in an Antarctic marine invertebrate (Nacella concinna). Cell Stress Chaperones. 14: 649-660.

Clarke J D, et al. 2011. Metabolism and Tissue Distribution of Sulforaphane in Nrf2 Knockout and Wild-Type Mice. Pharm Res.

Curran L K, et al. 2007. Behaviors associated with fever in children with autism spectrum disorders. Pediatrics. 120 (6): e1386-1392.

Durieux J, et al. 2011. The cell-non-autonomous nature of electron transport chain-mediated longevity. Cell. 144: 79-91.

Evans C G, et al. 2010. Heat shock protein 70 (hsp70) as an emerging drug target. J Med. Chem. 53: 4585-4602.

Fedoroff N. 2006. Redox regulatory mechanisms in cellular stress responses. Ann Bot. 98: 289-300.

Gan N, et al. 2010. Sulforaphane activates heat shock response and enhances proteasome activity through up-regulation of Hsp27. J Biol. Chem. 285(46): 35528-35536.

Gardian G, et al. 2005. Neuroprotective effects of phenylbutyrate in the N171-82Q transgenic mouse model of Huntington's disease. J Biol. Chem. 280: 556-563.

Gibbs A, et al. 2009. Sulforaphane destabilizes the androgen receptor in prostate cancer cells by inactivating histone deacetylase 6. Proc Natl Acad Sci USA. 106(39): 16663-16668.

Gorski G, et al. 1985. Increased expression of fragile site Xq by hydroxyurea. Preliminary communication. Acta Anthropogenet. 9: 71-76.

Habashi J P, et al. 2006. Losartan, an AT1 antagonist, prevents aortic aneurysm in a mouse model of Marfan syndrome. Science. 312: 117-121.

Heinzer A K, et al. 2003. Mouse models and genetic modifiers in X-linked adrenoleukodystrophy. Adv Exp Med. Biol. 544: 75-93.

Horowitz M, et al. 2007. Heat shock proteins and the heat shock response during hyperthermia and its modulation by altered physiological conditions. Prog Brain Res. 162: 433-446.

Hsiao C H, et al. 2006. Fetal hemoglobin induction by histone deacetylase inhibitors involves generation of reactive oxygen species. Exp Hematol. 34: 264-273.

Hu R, et al. 2006. Gene expression profiles induced by cancer chemopreventive isothiocyanate sulforaphane in the liver of C57BL/6J mice and C57BL/6J/Nrf2 (−/−) mice. Cancer Lett. 243(2): 170-192.

Hutt D M, et al. 2010. Reduced histone deacetylase 7 activity restores function to misfolded CFTR in cystic fibrosis. Nat Chem. Biol. 6: 25-33.

James S J, et al. 2009. Cellular and mitochondrial glutathione redox imbalance in lymphoblastoid cells derived from children with autism. FASEB J. 23(8): 2374-2383.

Jung M. 2001. Inhibitors of histone deacetylase as new anti-cancer agents. Curr Med. Chem. 8: 1505-1511.

Keefer J R, et al. 2006. Role of cyclic nucleotides in fetal hemoglobin induction in cultured CD34+ cells. Exp Hematol. 34: 1151-1161.

Kemp S, et al. 1998. Gene redundancy and pharmacological gene therapy: implications for X-linked adrenoleukodystrophy. Nat. Med. 4: 1261-1268.

Kultz D. 2003. Evolution of the cellular stress proteome: from monophyletic origin to ubiquitous function. J Exp Biol. 206: 3119-3124.

Kultz D. 2005. Molecular and evolutionary basis of the cellular stress response. Annu Rev Physiol. 67: 225-257.

Lallemand D, et al. 1998. Stress-activated protein kinases are negatively regulated by cell density. EMBO J. 17: 5615-5626.

Lee H C, et al. 2005. Mitochondrial biogenesis and mitochondrial DNA maintenance of mammalian cells under oxidative stress. Int J Biochem Cell Biol. 37: 822-834.

Li X, et al. 2002. PEX11alpha is required for peroxisome proliferation in response to 4-phenylbutyrate but is dispensable for peroxisome proliferator-activated receptor alpha-mediated peroxisome proliferation. Mol Cell Biol. 22: 8226-8240.

Liu J, et al. 2009. Targeting mitochondrial biogenesis for preventing and treating insulin resistance in diabetes and obesity: Hope from natural mitochondrial nutrients. Adv Drug Deliv Rev. 61: 1343-1352.

Lunn M R, et al. 2008. Spinal muscular atrophy. Lancet. 371: 2120-2133.

Madeo F, et al. 2009. Autophagy for the avoidance of neurodegeneration. Genes Dev. 23: 2253-2259.

Martinet W, et al. 2009. Autophagy in disease: a double-edged sword with therapeutic potential. Clin Sci (Lond). 116: 697-712.

McGuinness M C, et al. 2003. Role of ALDP (ABCD1) and mitochondria in X-linked adrenoleukodystrophy. Mol Cell Biol 23: 744-753.

McGuinness M C, et al. 2001. Evaluation of pharmacological induction of fatty acid beta-oxidation in X-linked adrenoleukodystrophy. Mol Genet Metab. 74(1-2): 256-263.

Mehler M F, et al. 2009. Autism, fever, epigenetics and the locus coeruleus. Brain Res Rev. 59(2): 388-392.

Miles J H. Unpublished observations. Paper presented at: Simons Foundation Workshop on Fever and Autism; Feb. 5, 2010.

Minetti G C, et al. 2006. Functional and morphological recovery of dystrophic muscles in mice treated with deacetylase inhibitors. Nat. Med. 12: 1147-1150.

Myzak M C, et al. 2004. A novel mechanism of chemoprotection by sulforaphane: inhibition of histone deacetylase. Cancer Res. 64: 5767-5774.

Oliveira J M, et al. 2006. Mitochondrial-dependent Ca2+ handling in Huntington's disease striatal cells: effect of histone deacetylase inhibitors. J. Neurosci. 26: 11174-11186.

Ong D S, et al. 2011. Chemical and/or biological therapeutic strategies to ameliorate protein misfolding diseases. Curr Opin Cell Biol. 23(2):231-238.

Ozcan U, et al. 2006. Chemical chaperones reduce ER stress and restore glucose homeostasis in a mouse model of type 2 diabetes. Science. 313: 1137-1140.

Park H M, et al. 2009. Protection against amyloid beta cytotoxicity by sulforaphane: role of the proteasome. Arch Pharm Res. 32: 109-115.

Perrine S P. 2008. Fetal globin stimulant therapies in the beta-hemoglobinopathies: principles and current potential. Pediatr Ann. 37: 339-346.

Petri S, et al. 2006. Additive neuroprotective effects of a histone deacetylase inhibitor and a catalytic antioxidant in a transgenic mouse model of amyotrophic lateral sclerosis. Neurobiol Dis. 22: 40-49.

Powers E T, et al. 2009. Biological and chemical approaches to diseases of proteostasis deficiency. Annu Rev Biochem. 78: 959-991.

Qi X, et al. 2004. Sodium 4-phenylbutyrate protects against cerebral ischemic injury. Mol. Pharmacol. 66: 899-908.

Ranganathan S, et al. 2009. Mitochondrial abnormalities in spinal and bulbar muscular atrophy. Hum Mol. Genet. 18: 27-42.

Ricobaraza A, et al. 2009. Phenylbutyrate ameliorates cognitive deficit and reduces tau pathology in an Alzheimer's disease mouse model. Neuropsychopharmacology 34: 1721-1732.

Santos M J, et al. 2005. Peroxisomal proliferation protects from beta-amyloid neurodegeneration. J Biol. Chem. 280: 41057-41068.

Schrader M, et al. 1998. Expression of PEX11beta mediates peroxisome proliferation in the absence of extracellular stimuli. J Biol. Chem. 273: 29607-29614.

Stetler R A, et al. 2010. Heat shock proteins: cellular and molecular mechanisms in the central nervous system. Prog Neurobiol. 92(2): 184-211.

Sun C, et al. Transduction through the repression of HDAC2. Biochem Pharmacol. 76: 120-127.

Toth A, et al. 2007. Endoplasmic reticulum stress as a novel therapeutic target in heart diseases. Cardiovasc Hematol Disord Drug Targets. 7: 205-218.

Vandesompele J, et al. 2002. Accurate normalization of real-time quantitative RT-PCR data by geometric averaging of multiple internal control genes. Genome Biol. 3: RESEARCH0034.

Vargas D L, et al. 2005. Neuroglial activation and neuroinflammation in the brain of patients with autism. Ann Neurol. 57(1): 67-81.

Watkins P A, et al. 1995. Altered expression of ALDP in X-linked adrenoleukodystrophy. Am J Hum Genet. 57: 292-301.

Wei H, et al. 2000. Pharmacological induction of peroxisomes in peroxisome biogenesis disorders. Ann Neurol. 47: 286-296.

Weissman J R, et al. 2008. Mitochondrial disease in autism spectrum disorder patients: a cohort analysis. PLoS One. 3(11): e3815.

Weng S J, et al. 2010. Alterations of resting state functional connectivity in the default network in adolescents with autism spectrum disorders. Brain Res. 1313: 202-214.

Westerheide S D, et al. 2009. Stress-inducible regulation of heat shock factor 1 by the deacetylase SIRT1. Science. 323: 1063-1066.

Wiggins J L, et al. 2011. Using a self-organizing map algorithm to detect age-related changes in functional connectivity during rest in autism spectrum disorders. Brain Res. 1380: 187-197.

Xue M, et al. 2008. Activation of NF-E2-related factor-2 reverses biochemical dysfunction of endothelial cells induced by hyperglycemia linked to vascular disease. Diabetes. 57: 2809-2817.

Yang J, et al. 2003. Protein kinases and their involvement in the cellular responses to genotoxic stress. Mutat Res. 543: 31-58.

Yoon H Y, et al. 2008. Sulforaphane protects kidneys against ischemia-reperfusion injury through induction of the Nrf2-dependent phase 2 enzyme. Biochem Pharmacol. 75: 2214-2223.

Zhao J, et al. 2005. Sulforaphane enhances aquaporin-4 expression and decreases cerebral edema following traumatic brain injury. J Neurosci Res. 82(4): 499-506.

---

What is claimed is:

1. A method of treating autism or one or more autism spectrum disorders, comprising,
   administering to a subject diagnosed with autism or one or more autism spectrum disorders an effective amount of a composition comprising a sulforaphane, a sulforaphane dithiocarbamate, or combination thereof.

2. The method of claim 1, wherein in at least one cell of the subject, a stress proteome is stimulated.

3. The method of claim 1, wherein in at least one cell of the subject, increased nitrous oxide production is detected.

4. The method of claim 1, wherein in at least one cell of the subject stress-sensing organelles are increased from an amount prior to the administration of the composition.

5. The method of claim 4, wherein the stress-sensing organelle is a mitochondrion.

6. The method of claim 4, wherein the stress-sensing organelle is a peroxisome.

7. The method of claim 1, wherein the administering induces, in at least one cell of the subject, a general cellular stress response comprising at least one of mitochondrial biogenesis, peroxisome proliferation, activation of a stress proteome, transcription and/or translation of genes and proteins encoded by genes comprising heat shock and unfolded protein, genes for autophagic responses, genes for antioxidant responses, and genes for a c-jun-N-terminal kinase pathway.

8. The method of claim 7, wherein genes for heat shock proteins comprise heat shock protein 40, 70, and/or 90 family members; unfolded protein genes comprise glucose regulated protein 78 (BIP), PERK, inositol requiring 1 (IRE1) and activating transcription factor 6; autophagic response genes comprise beclin-1 (BCN1), autophagy protein 5 (ATG5) and microtubule-associated protein 1 light chain 3 (LC3 or APG8); and antioxidant response genes comprises expression of nuclear factor erythroid 2-like 2 (NFE2L2), heme oxygenase 1 (HMOX1) and superoxide dismutase 2 (SOD2).

9. The method of claim 7, wherein the at least one cell of the subject is located in the brain of the subject.

10. The method of claim 7, wherein the at least one cell of the subject is not located in the brain of the subject.

11. The method of claim 1, wherein the composition is a pharmaceutical composition, a medical food, a food, a drink, or a dietary supplement.

12. A method of treating autism or one or more autism spectrum disorders, comprising, administering to a subject diagnosed with autism or one or more autism spectrum disorders an effective amount of a pharmaceutical composition comprising a sulforaphane, a sulforaphane dithiocarbamate, or combination thereof.

13. The method of claim 12, wherein in at least one cell of the subject, a stress proteome is stimulated.

14. The method of claim 12, wherein in at least one cell of the subject, increased nitrous oxide production is detected.

15. The method of claim 12, wherein in at least one cell of the subject stress-sensing organelles are increased from an amount prior to the administration of the composition.

16. The method of claim 15, wherein the stress-sensing organelle is a mitochondrion.

17. The method of claim 15, wherein the stress-sensing organelle is a peroxisome.

18. The method of claim 12, wherein the administering induces, in at least one cell of the subject, a general cellular stress response comprising at least one of mitochondrial biogenesis, peroxisome proliferation, activation of a stress proteome, transcription and/or translation of genes and proteins encoded by genes comprising heat shock and unfolded protein, genes for autophagic responses, genes for antioxidant responses, and genes for a c-jun-N-terminal kinase pathway.

19. The method of claim 18, wherein genes for heat shock proteins comprise heat shock protein 40, 70, and/or 90 family members; unfolded protein genes comprise glucose regulated protein 78 (BIP), PERK, inositol requiring 1 (IRE1) and activating transcription factor 6; autophagic response genes comprise beclin-1 (BCN1), autophagy protein 5 (ATG5) and microtubule-associated protein 1 light chain 3 (LC3 or APG8); and antioxidant response genes comprises expression of nuclear factor erythroid 2-like 2 (NFE2L2), heme oxygenase 1 (HMOX1) and superoxide dismutase 2 (SOD2).

20. The method of claim 18, wherein the at least one cell of the subject is located in the brain of the subject.

21. The method of claim 18, wherein the at least one cell of the subject is not located in the brain of the subject.

* * * * *

SEQUENCE LISTING

```
<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 1
cccagaaact tggactggaa                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 2
cccagcgcta agagtaaacg                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 3
caggtggcac agcttaaaca                                                 20
```

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 4
tgagttggca cccactgtta                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 5
agctgctgaa gaggcaagag                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 6
ctccaggaaa agcaaagctg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 7
tgaagccatg gattttgaca                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 8
tattggaagg gccttgtctg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 9
tatcagacag cgcagtcacc                                              20

<210> SEQ ID NO 10
```

```
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 10
caatgtcacc acctccacag                                            20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 11
ggcagctggt tttattggaa                                            20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 12
acagtttcac gtccccactc                                            20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 13
gcacaggaaa ccagttagg                                             19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 14
atctgggttt tccaaagcaa                                            20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 15
agatgacctg gaaaccatgc                                            20

<210> SEQ ID NO 16
<211> LENGTH: 20
```

```
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 16
gtgtcatcca acgtggtcag                                             20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 17
actgcctgga ggatagcaga                                             20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 18
accttggact gctggatgtc                                             20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 19
aatgaccaga atcgcctgac                                             20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 20
cgctccttga gcttttttgtc                                            20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 21
ccgctccaca gagatacaca                                             20

<210> SEQ ID NO 22
<211> LENGTH: 20
<212> TYPE: DNA
```

```
<213> ORGANISM: Artificial Sequence
<220> FEATURE:
<223> OTHER INFORMATION: Description of Artificial Sequence: note =
      synthetic construct

<400> SEQUENCE: 22
gtcttgtccg tccatccact                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 23
gcagaacctc agccactttc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 24
accgaggaga cgagactgaa                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 25
ggcagaggct gataagaacg                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 26
agacaggagc gcagtttcat                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 27
ccgagaagga cgagtttgag                                              20

<210> SEQ ID NO 28
<211> LENGTH: 20
<212> TYPE: DNA
<213> ORGANISM: Artificial Sequence
```

```
<220> FEATURE:
<223> OTHER INFORMATION: Description of Artificial Sequence: note =
      synthetic construct

<400> SEQUENCE: 28
ctggtacagt ccgctgatga                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 29
gatattttgc ccagcaggaa                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 30
tttgtctccc gttttggaac                                                 20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 31
acacggtcca cagctcatc                                                  19

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 32
tcttgcctcc aaagtatgtc aa                                              22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 33
tccgatgggt ccttacactc                                                 20

<210> SEQ ID NO 34
<211> LENGTH: 20
<212> TYPE: DNA
<213> ORGANISM: Artificial Sequence
<220> FEATURE:
```

```
<223> OTHER INFORMATION: Description of Artificial Sequence: note =
      synthetic construct

<400> SEQUENCE: 34
taaggaagcc agccaagaga                                                    20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 35
ccctggaacc tcacatcaac                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 36
cgttagggct gaggtttgtc                                                    20

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 37
acgttgctat ccaggctgtg ctat                                               24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 38
cggtgaggat cttcatgagg tagt                                               24

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 39
ttgccgccag aacacag                                                       17

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: note =
``` synthetic construct

<400> SEQUENCE: 40
acttgcccga atctacgtgt                                          20

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 41
tgctgtctcc atgtttgatg tatct                                    25

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 42
tctctgctcc ccacctctaa gt                                       22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 43
ggagctggaa gcctggtatg                                          20

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 44
gctctgggag gtgcttgt                                            18

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 45
caagatcctg gaccgtgtca                                          20

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: note =
      synthetic construct -continued

<400> SEQUENCE: 46
tggccatttc tgtggacatc a                                                    21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 47
tgcagaagaa aatggatttc g                                                    21

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 48
actgtccatc tgcagccac                                                       19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 49
gcgatgattc tgacatttgg                                                      20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 50
aatgaagcca cagctttatc a                                                    21

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 51
ataattcccc caccacctc                                                       19

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: note =
      synthetic construct

```
<400> SEQUENCE: 52
caccttcctt ctttttgatt ttgtc                                          25
```